US012091457B2

(12) United States Patent
Kim et al.

(10) Patent No.: US 12,091,457 B2
(45) **Date of Patent: *Sep. 17, 2024**

(54) USE FOR PREVENTING AND TREATING MYELOID-DERIVED SUPPRESSOR CELL-RELATED DISEASES

(71) Applicant: Kumho HT, Inc., Gwangju (KR)

(72) Inventors: Soseul Kim, Seoul (KR); Jeong Won Hong, Seoul (KR); Gil Yong Ji, Seoul (KR); Sangsoon Yoon, Seoul (KR); Hyung-Geun Song, Cheongju-si (KR)

(73) Assignee: KUMHO HT, INC., Gwangju (KR)

( * ) Notice: Subject to any disclaimer, the term of this patent is extended or adjusted under 35 U.S.C. 154(b) by 896 days.

This patent is subject to a terminal disclaimer.

(21) Appl. No.: 17/052,591

(22) PCT Filed: May 14, 2019

(86) PCT No.: PCT/KR2019/006007

§ 371 (c)(1),
(2) Date: Nov. 3, 2020

(87) PCT Pub. No.: WO2019/221574

PCT Pub. Date: Nov. 21, 2019

(65) Prior Publication Data

US 2022/0119518 A1 Apr. 21, 2022

(30) Foreign Application Priority Data

May 14, 2018 (KR) ........................ 10-2018-0054977
May 13, 2019 (KR) ........................ 10-2019-0055950

(51) Int. Cl.
*A61P 37/00* (2006.01)
*A61P 35/00* (2006.01)
*C07K 16/28* (2006.01)
*A61K 39/00* (2006.01)

(52) U.S. Cl.
CPC .......... *C07K 16/2803* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | | |
|---|---|---|---|---|
| 9,176,131 | B2 * | 11/2015 | Barnich | A61P 43/00 |
| 11,220,543 | B2 * | 1/2022 | Yoon | A61K 45/06 |
| 2011/0212095 | A1 | 9/2011 | Song et al. | |
| 2017/0267757 | A1 | 9/2017 | Hong et al. | |

FOREIGN PATENT DOCUMENTS

| | | |
|---|---|---|
| CN | 107743495 | 2/2018 |
| JP | 2007-530679 | 11/2007 |
| JP | 2016-520548 | 7/2016 |
| JP | 2018-502114 | 1/2018 |
| JP | 2018-510636 | 4/2018 |
| KR | 10-2009-0051598 | 5/2009 |
| KR | 10-2011-0098593 | 9/2011 |
| KR | 10-2017-0107325 | 9/2017 |
| KR | 10-2017-0128567 | 11/2017 |
| KR | 10-2018-0054492 | 5/2018 |
| WO | 2012-019127 | 2/2012 |
| WO | 2016150899 | 9/2016 |
| WO | 2018-067825 | 4/2018 |
| WO | 2018070936 | 4/2018 |

OTHER PUBLICATIONS

Joerg Willuda et al, "Abstract 1771: BAY 1834942 is an immunotherapeutic antibody blocking the novel immune checkpoint regulator CEACAM6 (CD66c)", AACR Annual Meeting 2018, Chicago, IL, Cancer Research, doi:10.1158/1538-7445.AM2018-1771, (Apr. 14, 2018).
C. J. Riley et al, "Design and Activity of a Murine and Humanized Anti-CEACAM6 Single-Chain Variable Fragment in the Treatment of Pancreatic Cancer", Cancer Research, US, (Feb. 10, 2009), vol. 69, No. 5, doi:10.1158/0008-5472.CAN-08-2707, ISSN 0008-5472, pp. 1933-1940, XP055271546.
EPO, Search Report of EP 19802548.8 dated Jan. 28, 2022.
KIPO, PCT Search Report & Written Opinion of PCT/KR2019/006007 dated Aug. 20, 2019.
Benny Johnson et al., "Emerging Role and Targeting of Carcinoembryonic Antigen-related Cell Adhesion Molecule 6 (CEACAM6) in Human Malignancies", Clinical Cancer Drugs, 2015, 2, 100-111.
Gabrilovich DI, et al., "Coordinated regulation of myeloid cells by tumors", Nat Rev Immunol. 12(4):253-268 (2012). doi:10.1038/nri3175.
Garbrilovich DI, et al., "Myeloid-derived suppressor cells as regulators of the immune system" , Nat Rev Immunol. Mar. 2009 ; 9(3): 162-174. doi:10.1038/nri2506.
Sherie L. Morrison et al., "Chimeric human antibody molecules: Mouse antigen-binding domains with human constant region domains", Proc. Natl. Acad. ScL USA, 81:6851-6855(1984).
Sherie L. Morrison et al., "Genetically Engineered Antibody Molecules", Adv. Immunol., 44:65-92 (1988).
Martine Verhoeyen et al., "Reshaping Human Antibodies: Grafting an Antilysozyme Activity", Science, 239:1534-1536 (1988).

(Continued)

*Primary Examiner* — Agnieszka Boesen
(74) *Attorney, Agent, or Firm* — LEX IP MEISTER, PLLC

(57) ABSTRACT

The present invention relates to an antibody or an antigen-binding fragment thereof specifically binding to CD66c which is expressed in myeloid-derived suppressor cell (MDSC) and a use thereof, and specifically to an antibody or an antigen-binding fragment thereof specifically binding to CD66c, a pharmaceutical composition or a diagnosing composition including the same. The anti-CD66c antibody of the present invention can be used usefully for the treatment of various diseases by targeting MDSC which can induce the immunosuppression.

22 Claims, 21 Drawing Sheets

Specification includes a Sequence Listing.

(56) References Cited

OTHER PUBLICATIONS

Eduardo A. Padlan, "A Possible Procedure for Reducing the Immunogenicity of Antibody Variable Domains While Preserving Their Ligand-Binding Properties", Immun., 28:489-498 (1991).
Eduardo A. Padlan, "Anatomy of the Antibody Molecule", Molec. Immun., 31(3):169-217 (1994).
George A. Dominguez et al., "Selective targeting of myeloid-derived suppressor cells in cancer patients using DS-8273a, an agonistic TRAIL-R2 antibody", Clin Cancer Res. Jun. 15, 2017; 23(12): 2942-2950. doi:10.1158/1078-0432.CCR-16-1784.
Suen Brandau et al., "Myeloid-derived suppressor cells in the peripheral blood of cancer patients contain a subset of immature neutrophils with impaired migratory properties", Journal of Leukocyte Biology. vol. 89, Feb. 2011. DOI: 10.1189/jlb.0310162.
KIPO, PCT Search Report & Written Opinion of PCT/KR2018/005743 dated May 8, 2019.
Xu Min et al., "Research Progress of Myeloid-derived Suppressor Cells Involved in Tumor Immune Escape", Medical Recapitulate, Mar. 2015, vol. 21, No. 6, pp. 1003-1005, Mar. 2015.
SIPO, Office Action of the corresponding Chinese Patent Application No. 201980031966.2.,dated Oct. 30, 2023.
JPO, Office Action of JP 2020-564084 dated Dec. 7, 2021.

* cited by examiner

【FIG. 1】
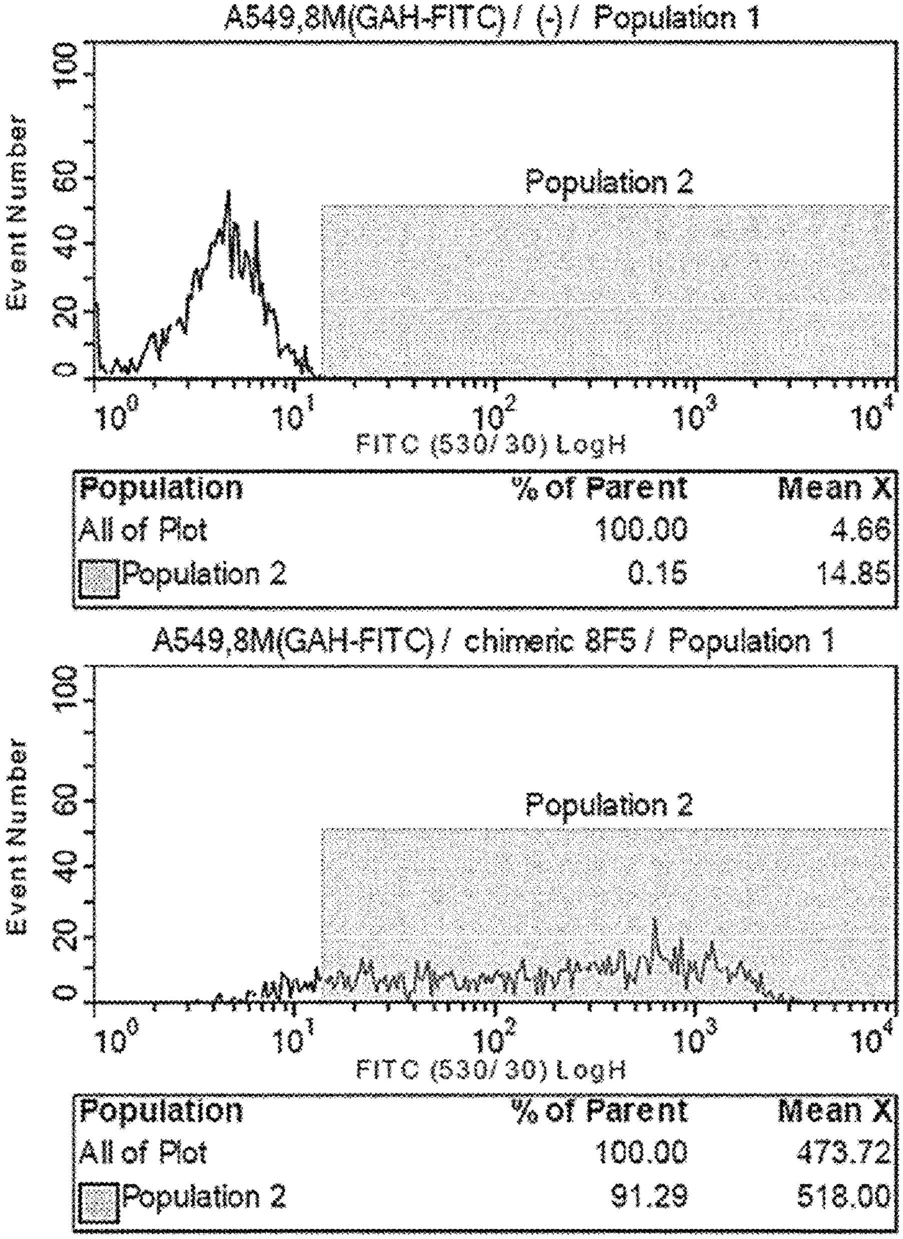

【FIG. 2a】
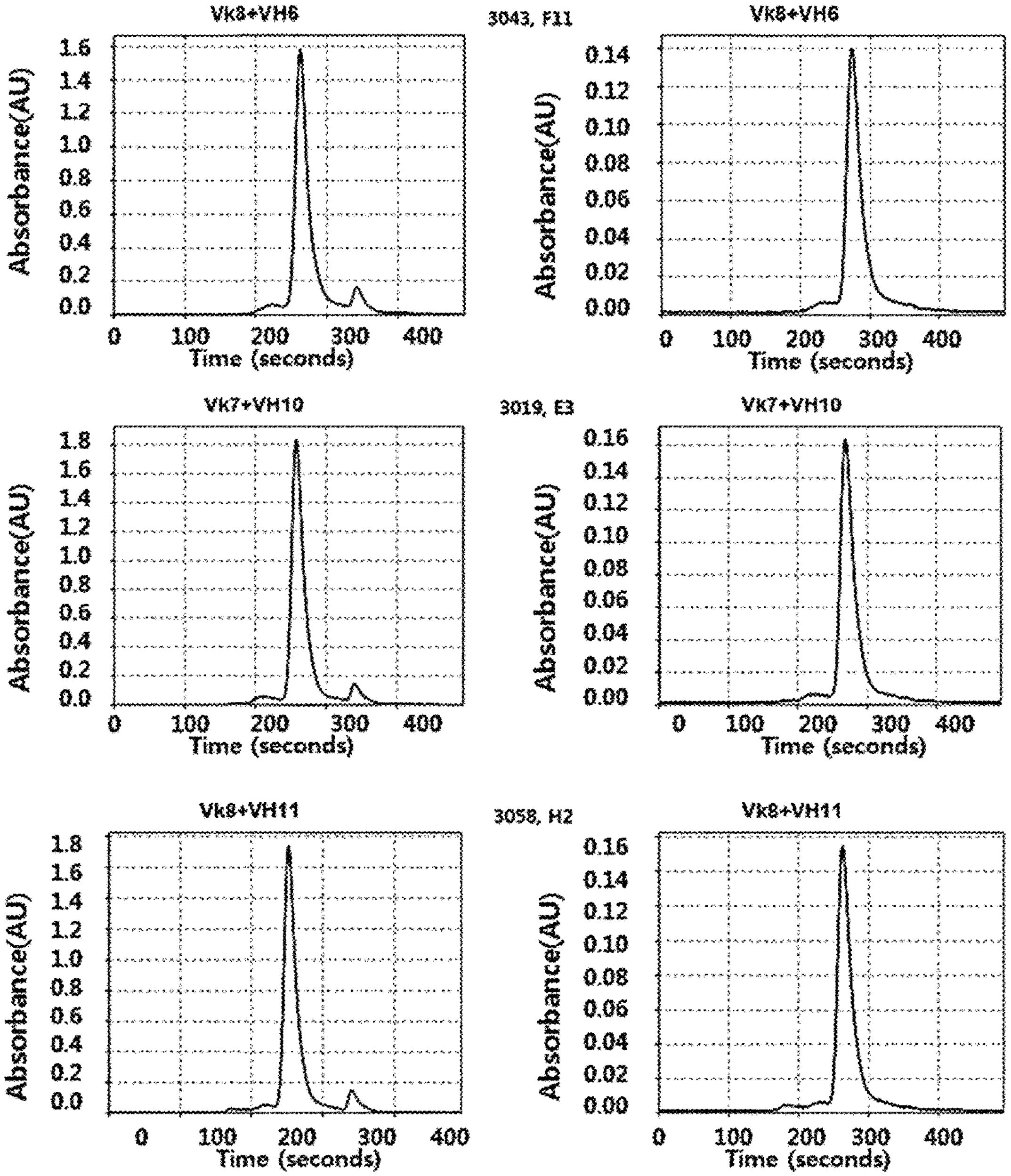

【FIG. 2b】
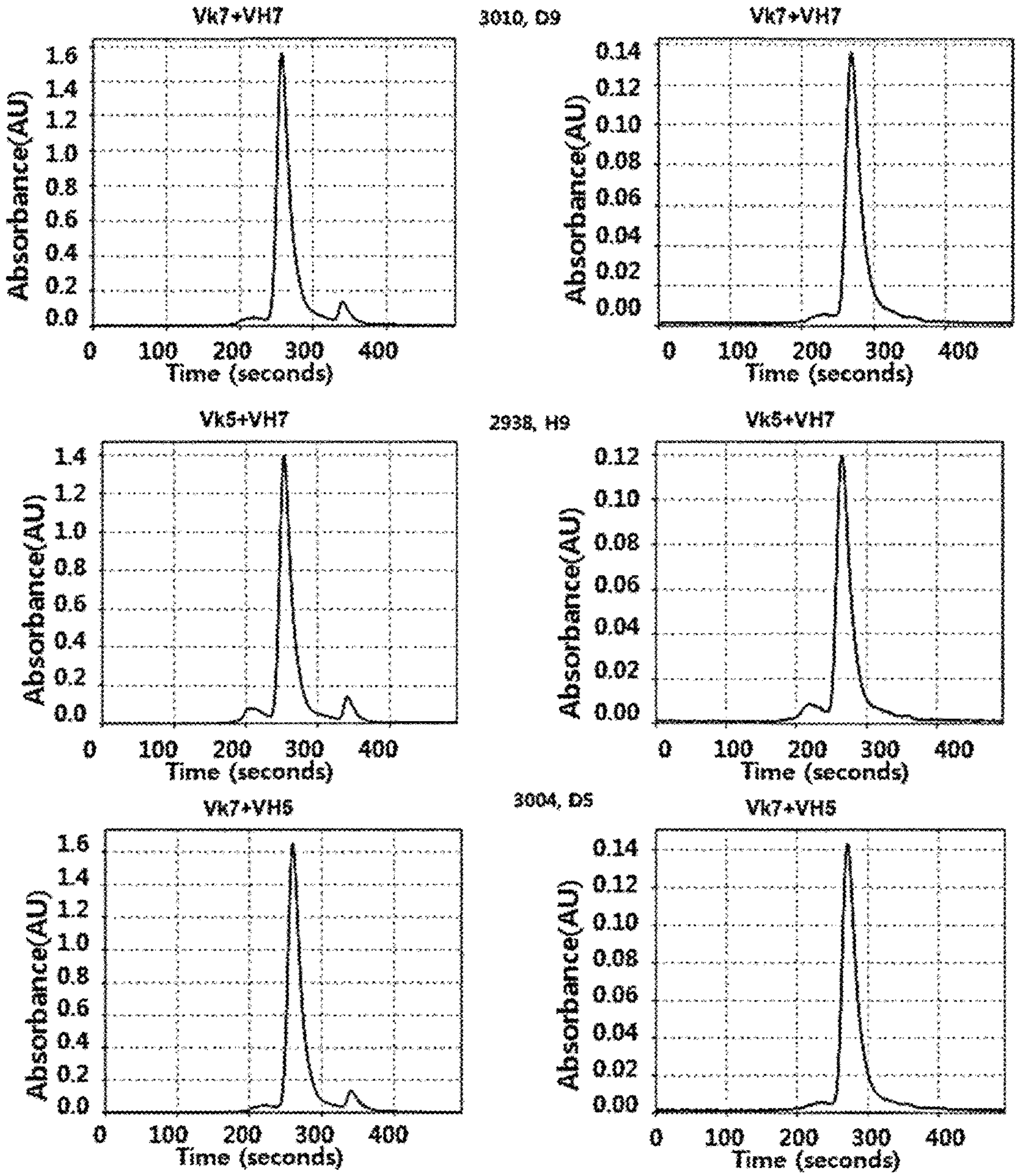

【FIG. 2c】
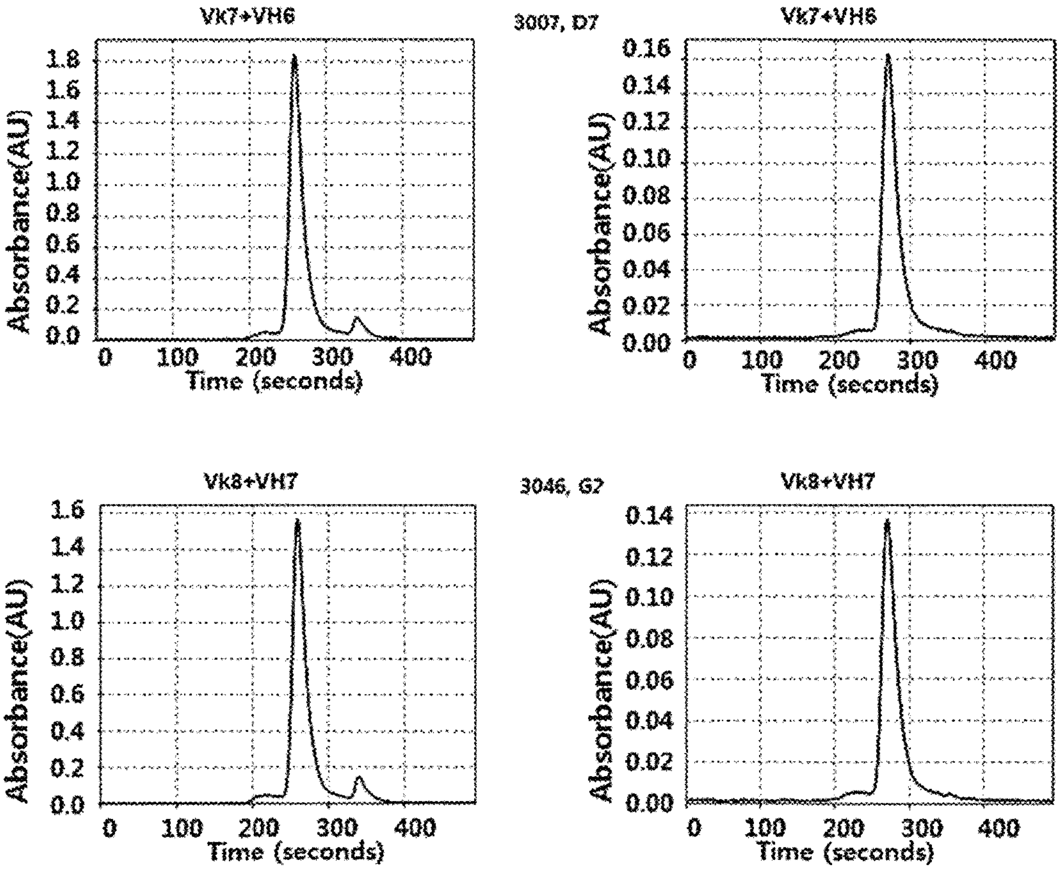

【FIG. 3a】
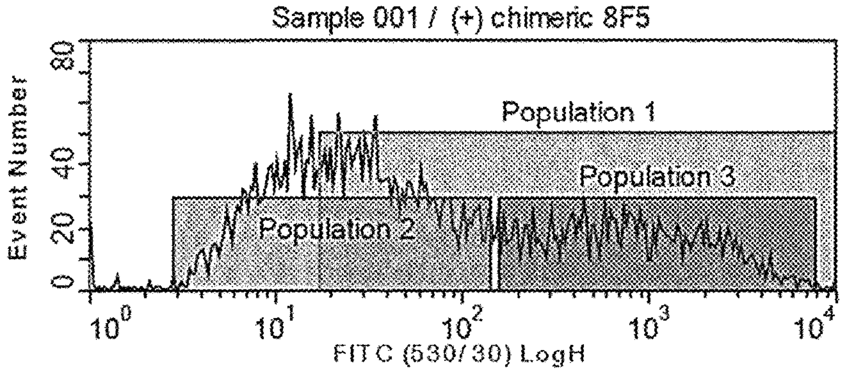
| Population | % of Par... | Mean X | Med X |
|---|---|---|---|
| All of Plot | 100.00 | 455.64 | 48.74 |
| Population 1 | 73.10 | 619.74 | 120.16 |
| Population 2 | 64.42 | 34.31 | 22.39 |
| Population 3 | 33.48 | 1256.91 | 752.11 |
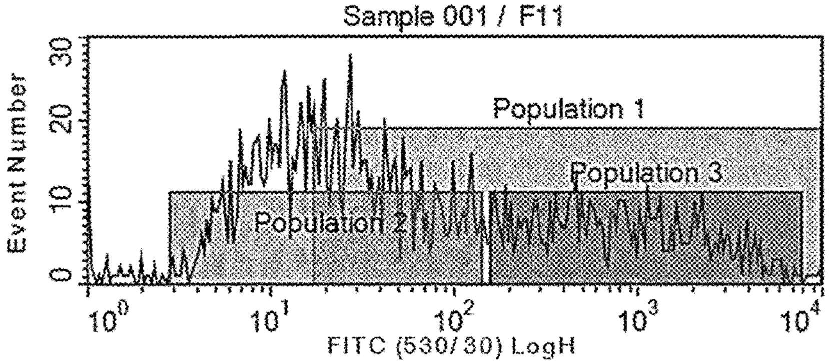
| Population | % of Par... | Mean X | Med X |
|---|---|---|---|
| All of Plot | 100.00 | 481.96 | 43.95 |
| Population 1 | 69.80 | 686.41 | 140.91 |
| Population 2 | 63.30 | 32.46 | 19.69 |
| Population 3 | 33.65 | 1272.50 | 747.37 |

【FIG. 3b】
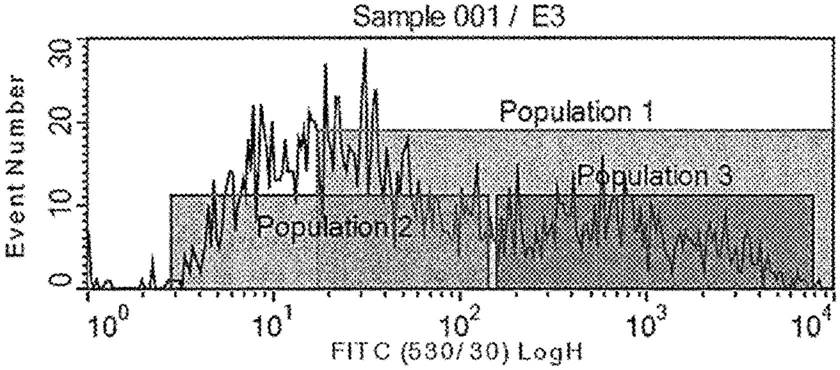
| Population | % of Par... | Mean X | Med X |
|---|---|---|---|
| All of Plot | 100.00 | 400.68 | 40.58 |
| Population 1 | 70.80 | 561.98 | 113.44 |
| Population 2 | 66.15 | 32.18 | 21.12 |
| Population 3 | 32.10 | 1164.73 | 690.03 |
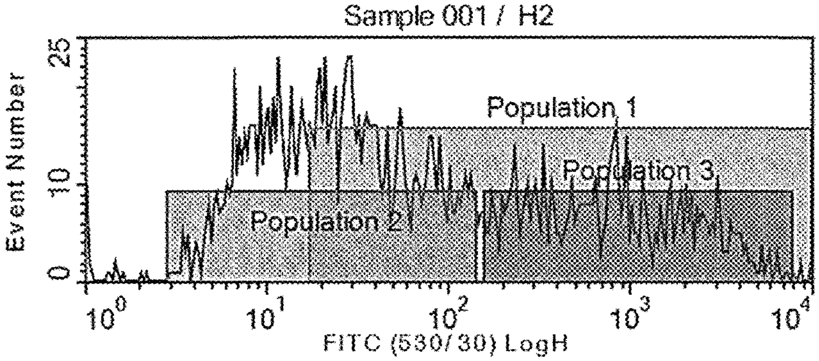
| Population | % of Par... | Mean X | Med X |
|---|---|---|---|
| All of Plot | 100.00 | 471.78 | 46.89 |
| Population 1 | 72.65 | 645.83 | 125.53 |
| Population 2 | 64.15 | 34.17 | 21.73 |
| Population 3 | 33.55 | 1269.36 | 787.37 |

【FIG. 3c】
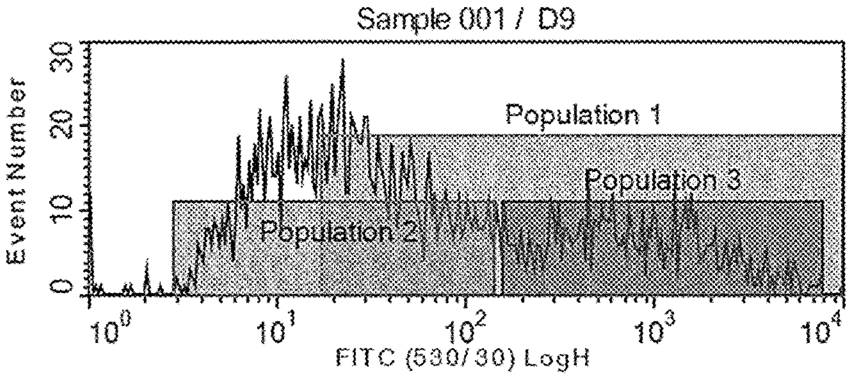
| Population | % of Par... | Mean X | Med X |
|---|---|---|---|
| All of Plot | 100.00 | 393.87 | 39.86 |
| Population 1 | 70.55 | 554.33 | 103.74 |
| Population 2 | 67.25 | 32.63 | 20.98 |
| Population 3 | 30.45 | 1198.89 | 733.32 |
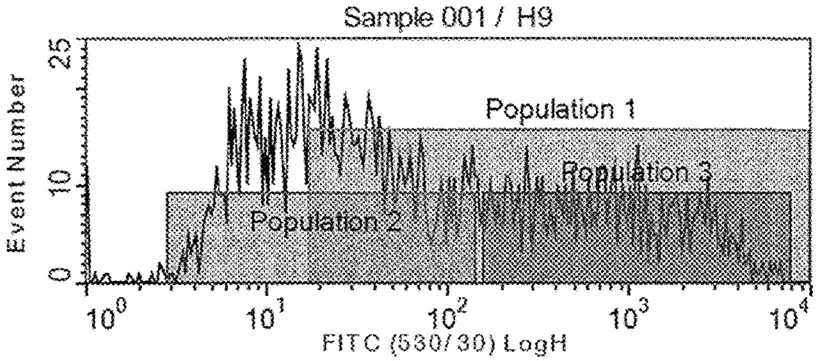
| Population | % of Par... | Mean X | Med X |
|---|---|---|---|
| All of Plot | 100.00 | 439.73 | 47.18 |
| Population 1 | 71.45 | 611.67 | 138.96 |
| Population 2 | 63.65 | 33.50 | 20.44 |
| Population 3 | 34.15 | 1220.18 | 731.98 |

【FIG. 3d】
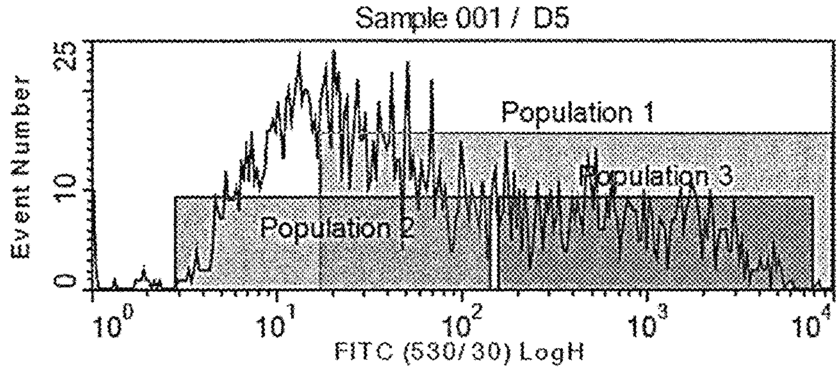
| Population | % of Par... | Mean X | Med X |
|---|---|---|---|
| All of Plot | 100.00 | 388.43 | 44.83 |
| Population 1 | 71.20 | 541.61 | 115.45 |
| Population 2 | 65.40 | 33.00 | 20.80 |
| Population 3 | 32.15 | 1122.02 | 666.86 |
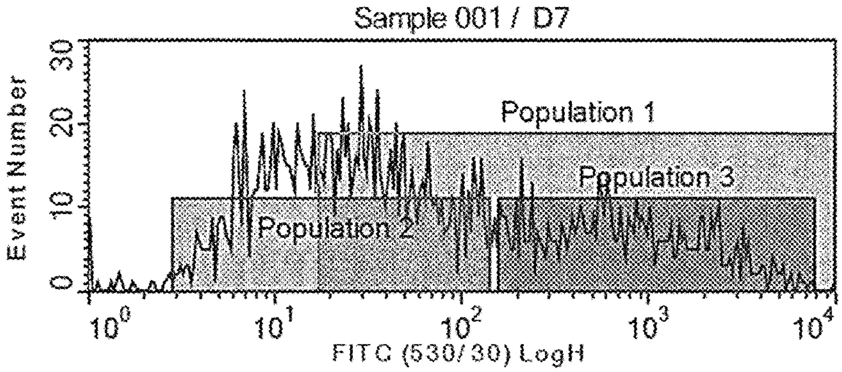
| Population | % of Par... | Mean X | Med X |
|---|---|---|---|
| All of Plot | 100.00 | 407.53 | 44.69 |
| Population 1 | 71.55 | 565.88 | 116.80 |
| Population 2 | 66.10 | 34.35 | 22.60 |
| Population 3 | 31.90 | 1186.45 | 707.71 |

【FIG. 3e】
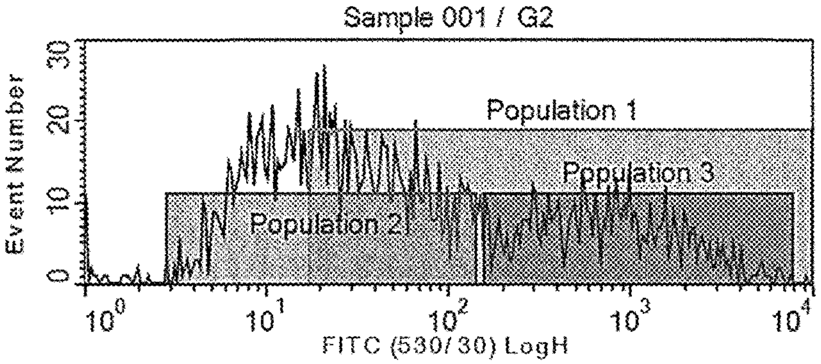
| Population | % of Par... | Mean X | Med X |
|---|---|---|---|
| All of Plot | 100.00 | 375.04 | 43.92 |
| Population 1 | 71.10 | 523.64 | 110.33 |
| Population 2 | 66.70 | 34.37 | 21.21 |
| Population 3 | 30.90 | 1119.24 | 730.14 |

【FIG. 4a】
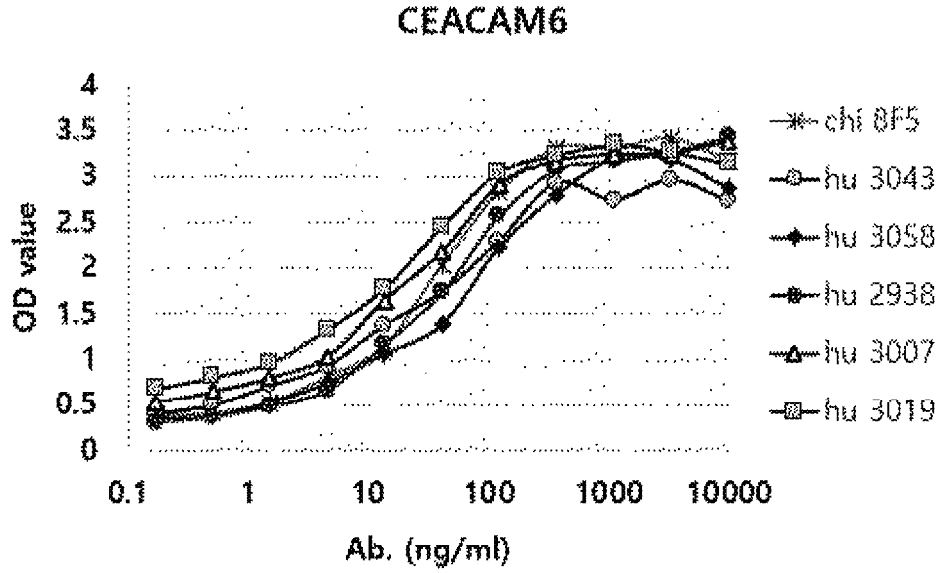
【FIG. 4b】
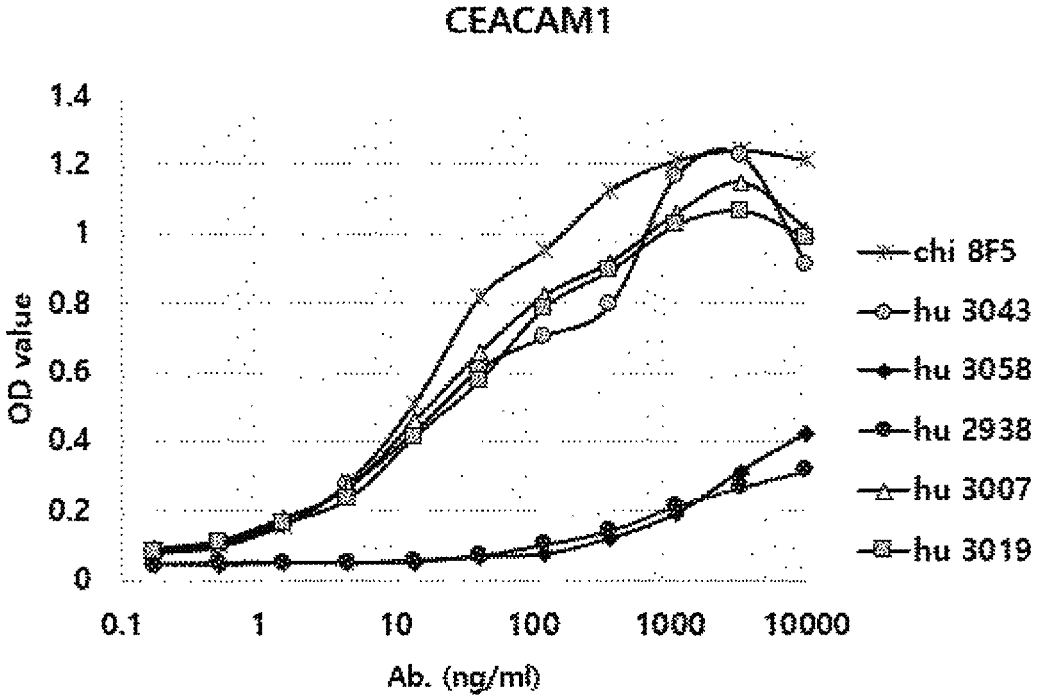

【FIG. 5a】
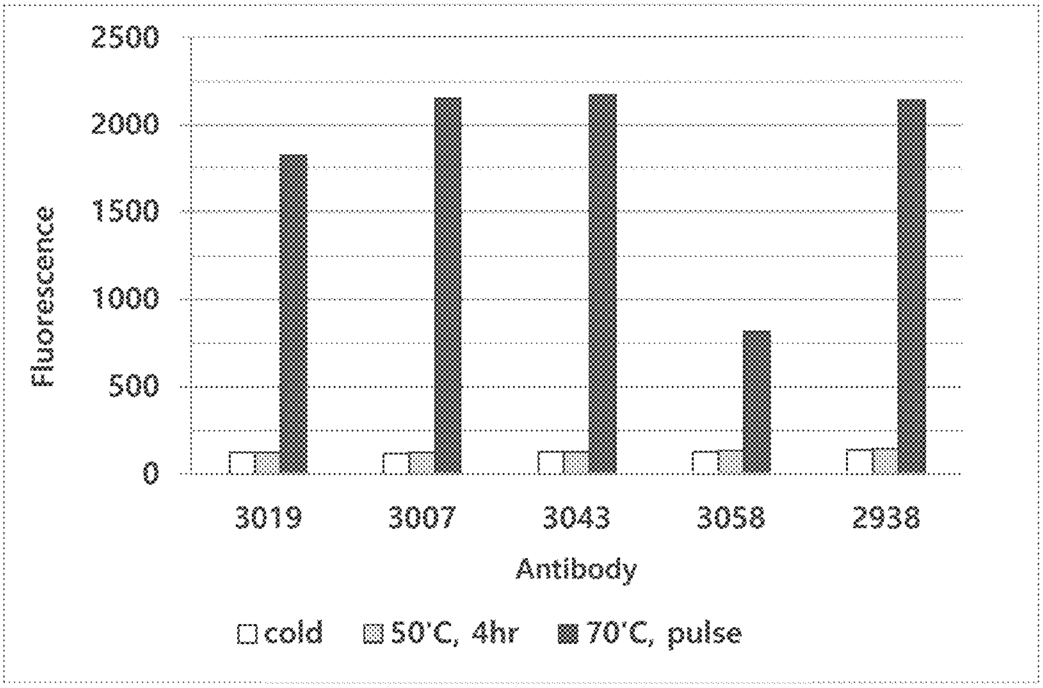
【FIG. 5b】
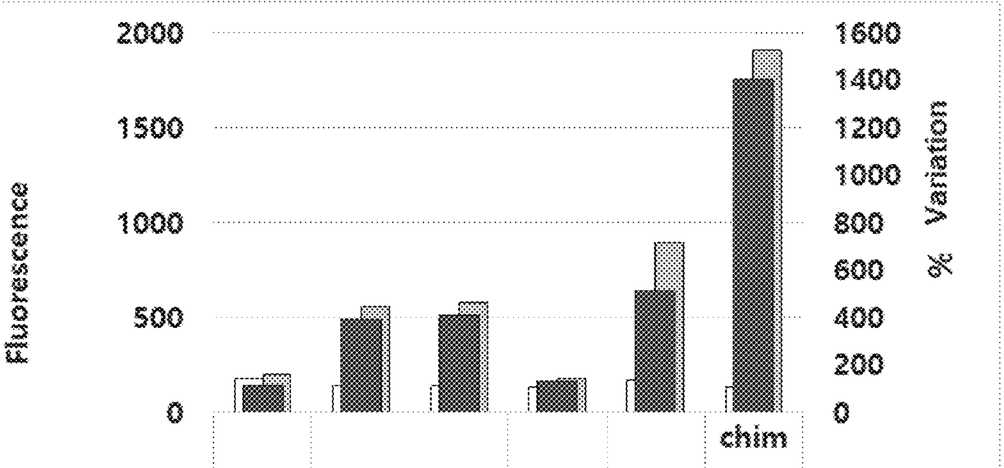
| | 3019 | 3007 | 3043 | 3058 | 2938 | chimeric 8F5 |
|---|---|---|---|---|---|---|
| □ Cooled condition | 175 | 142 | 141 | 133 | 173 | 136 |
| ▨ 62℃ (4hour) | 199 | 561 | 582 | 177 | 892 | 1912 |
| ■ Variation(%) | 114 | 395 | 413 | 133 | 516 | 1406 |

【FIG. 6a】
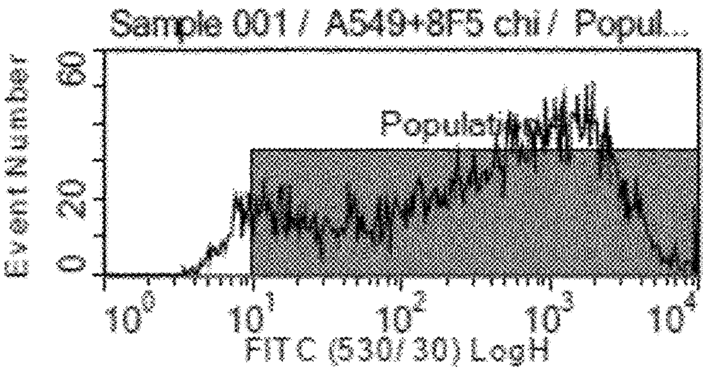
Tube name: A549+8F5 chi
Total Events: 4387
| Population | % of Par... | Mean X |
|---|---|---|
| All of Plot | 100.00 | 1003.20 |
| Population 4 | 95.03 | 1055.29 |
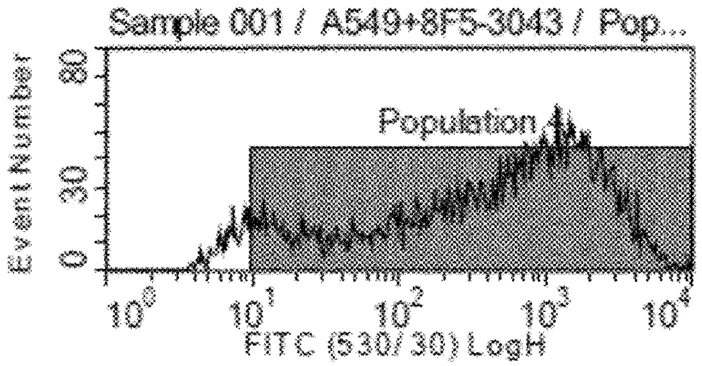
Tube name: A549+8F5-3043
Total Events: 4606
| Population | % of Par... | Mean X |
|---|---|---|
| All of Plot | 100.00 | 1010.37 |
| Population 4 | 94.49 | 1068.94 |

【FIG. 6b】
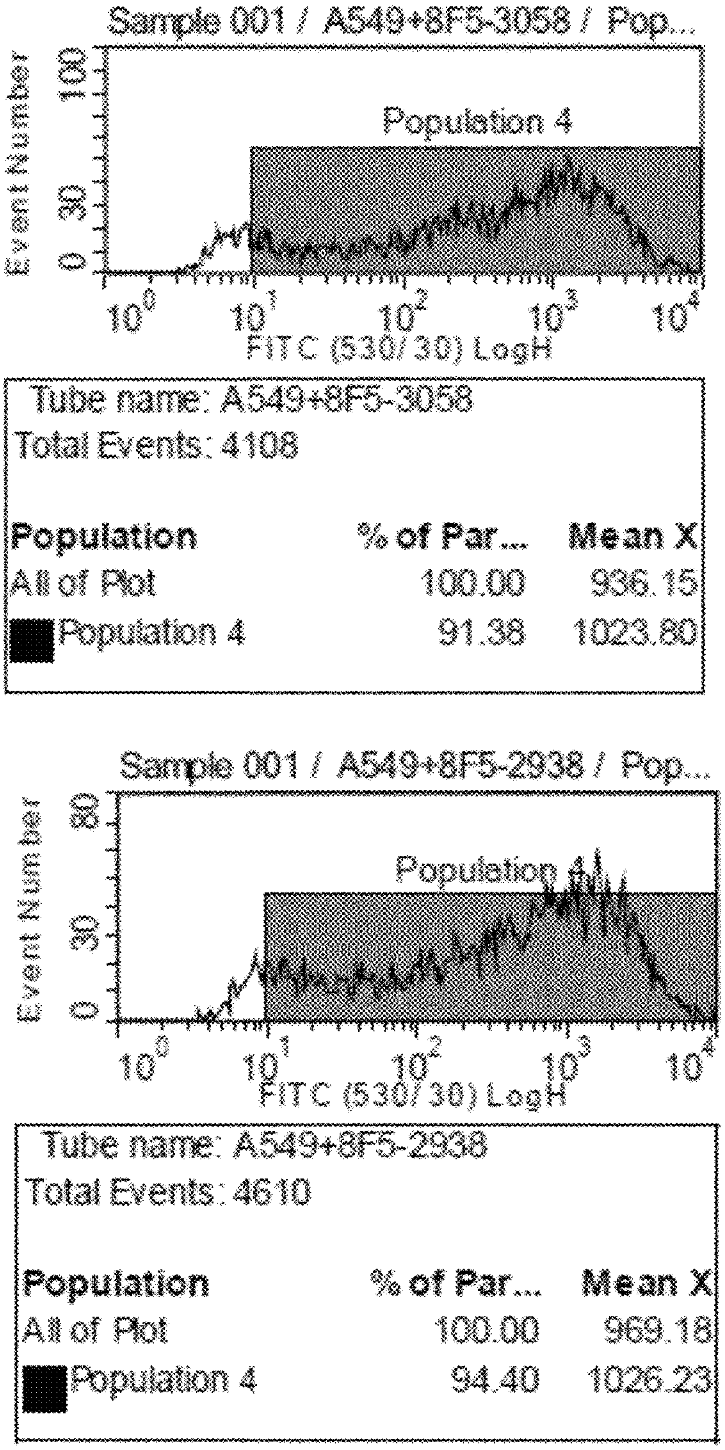

【FIG. 6c】
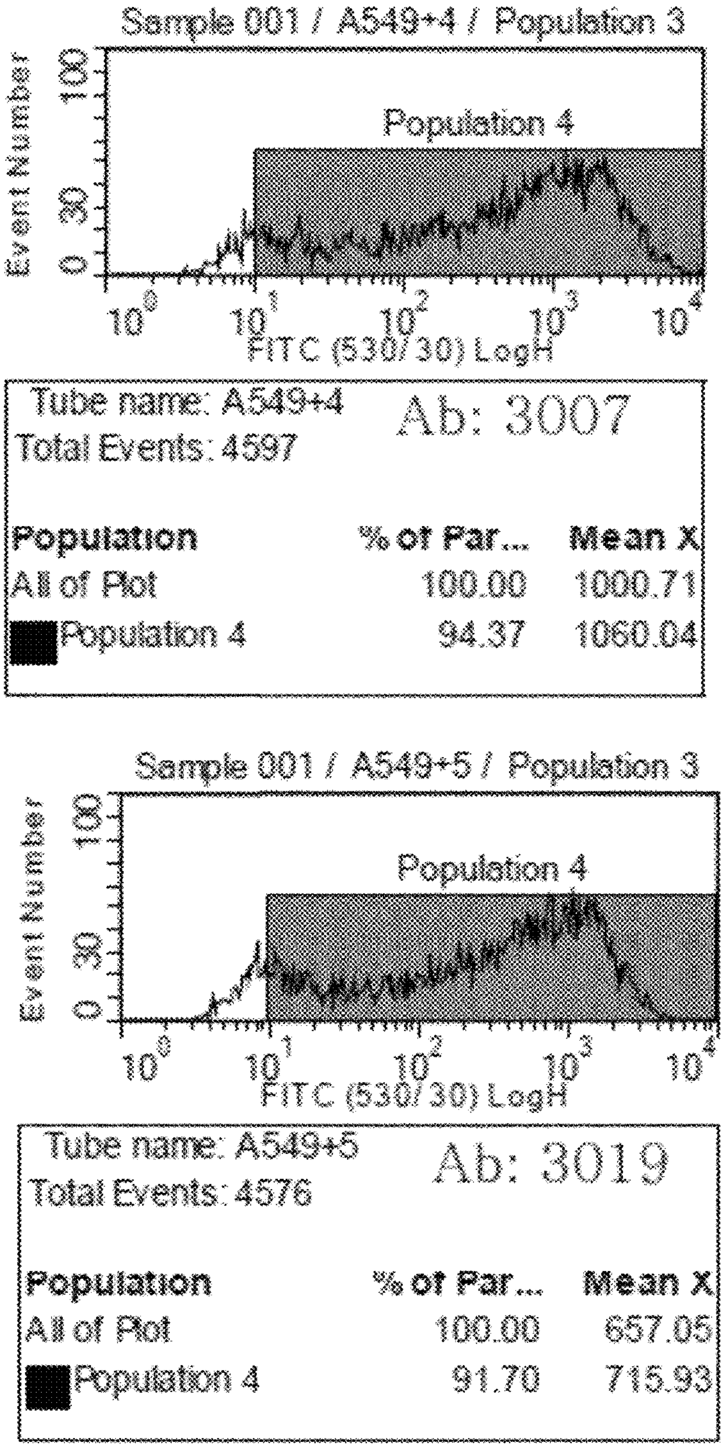

【FIG. 6d】
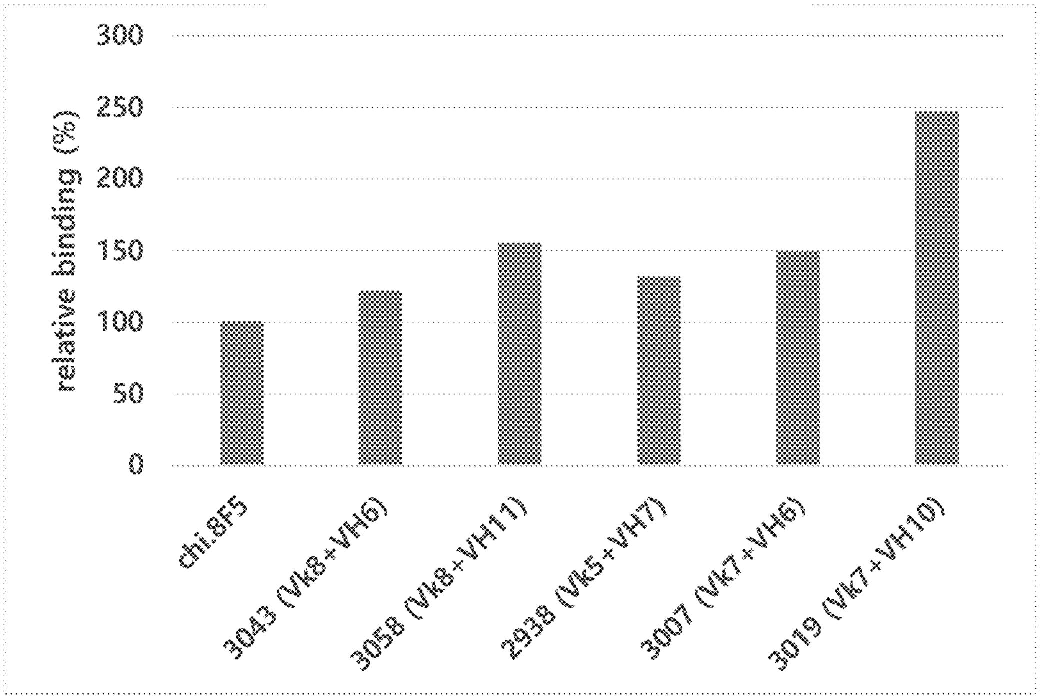

【FIG. 7】
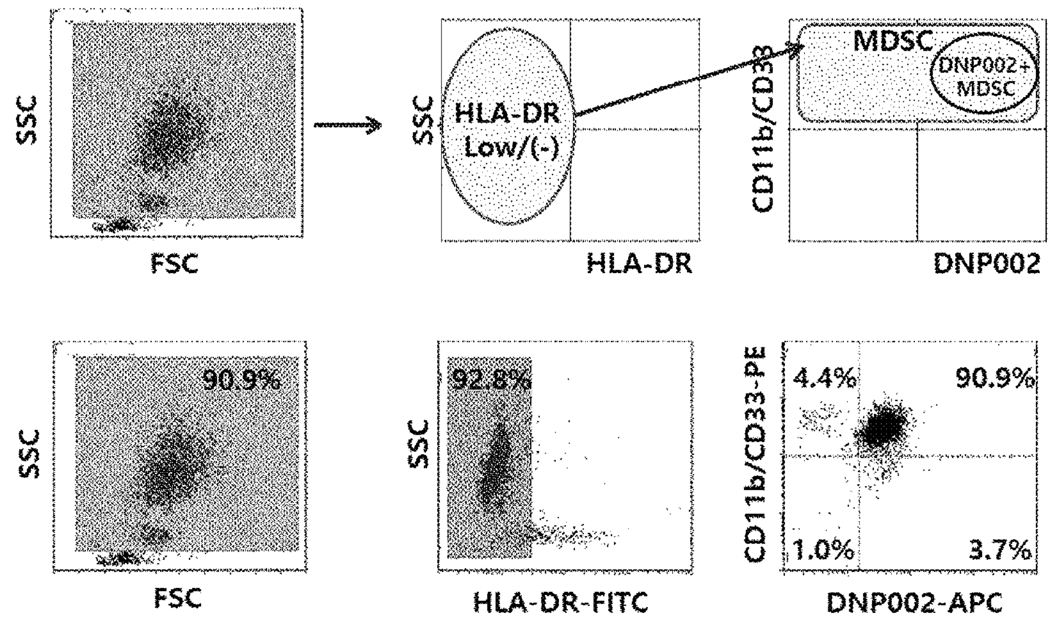
【FIG. 8】
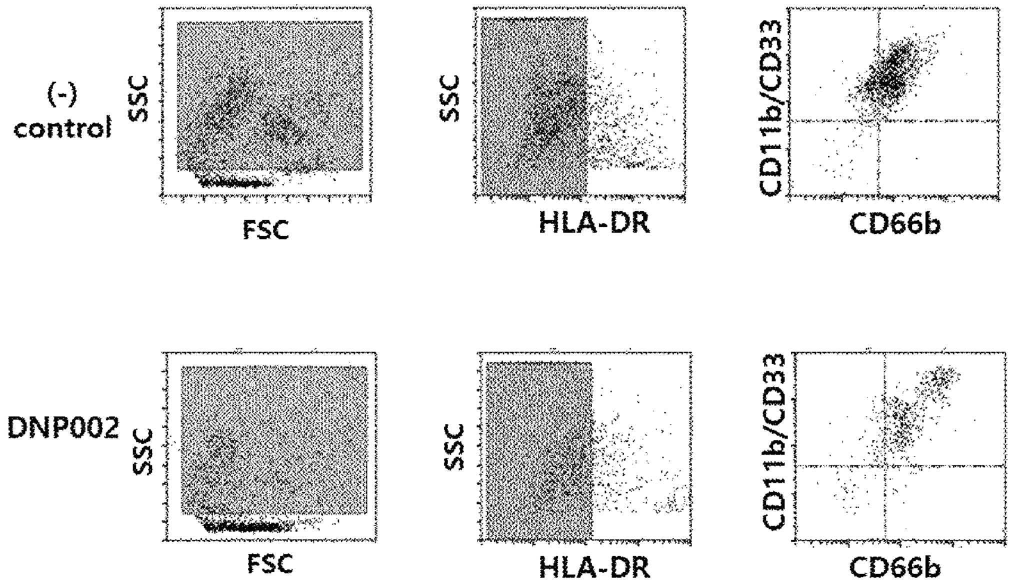

【FIG. 9】
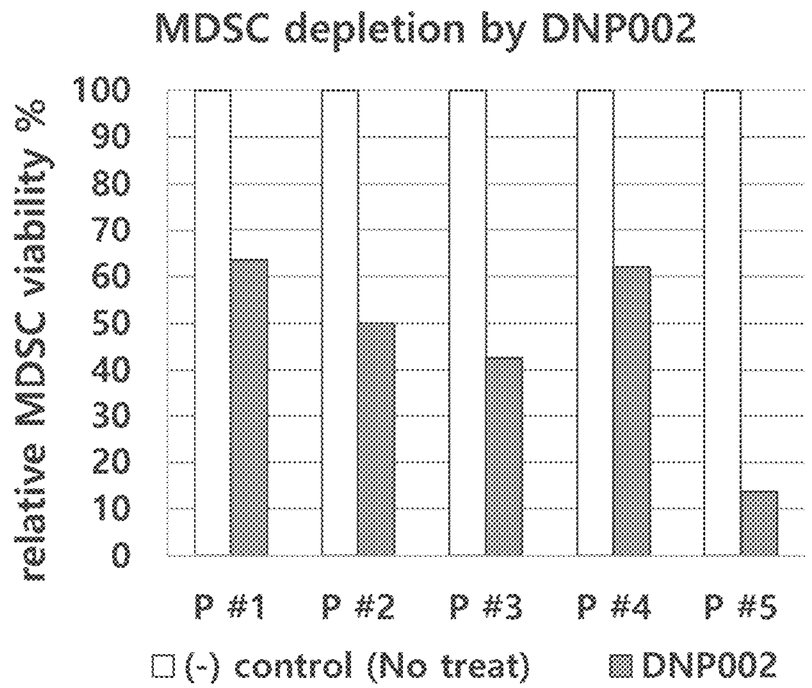
【FIG. 10】
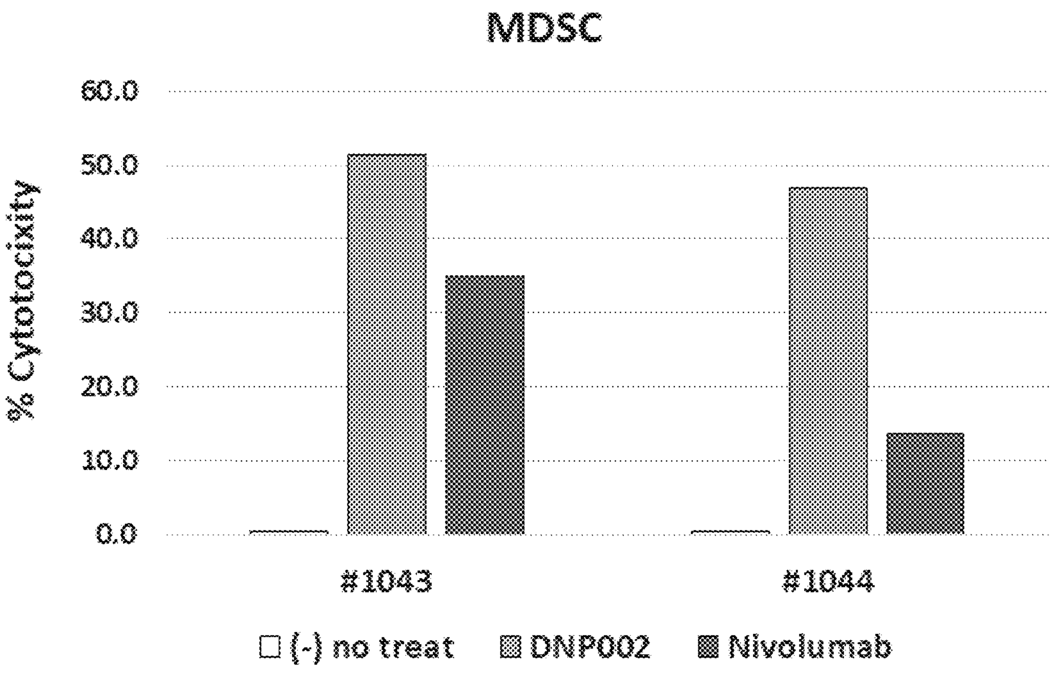

【FIG. 11a】
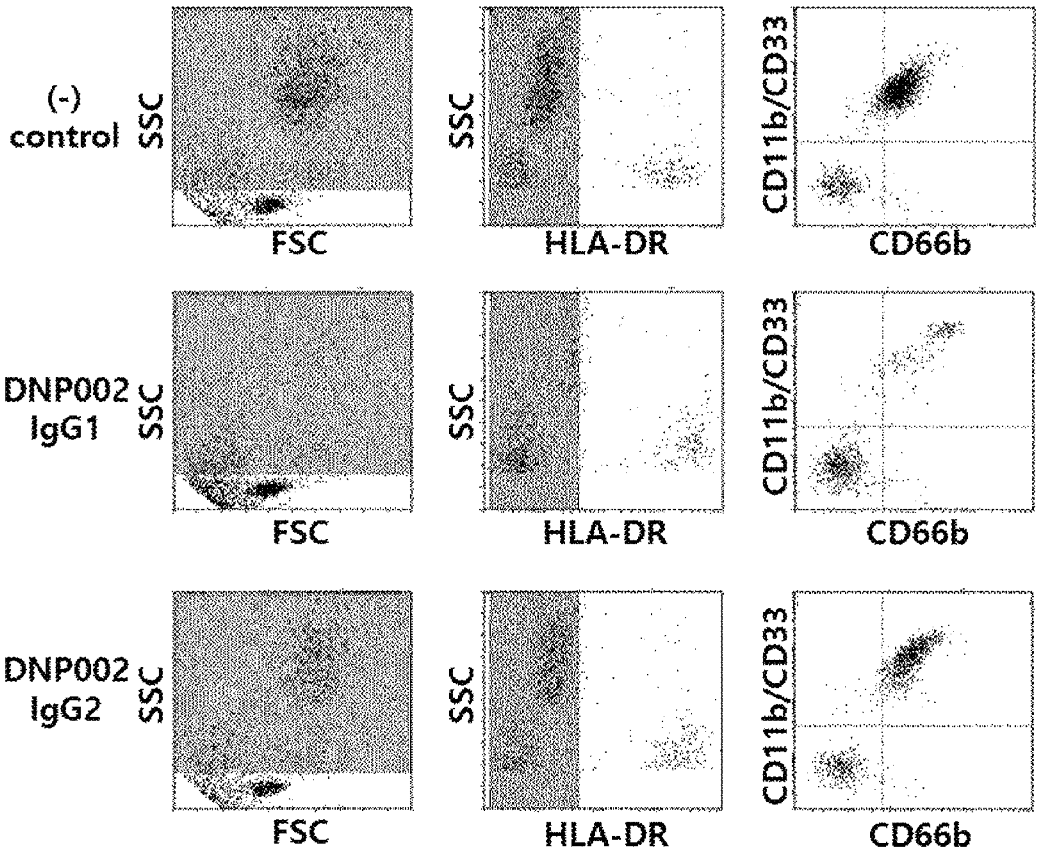

【FIG. 11b】
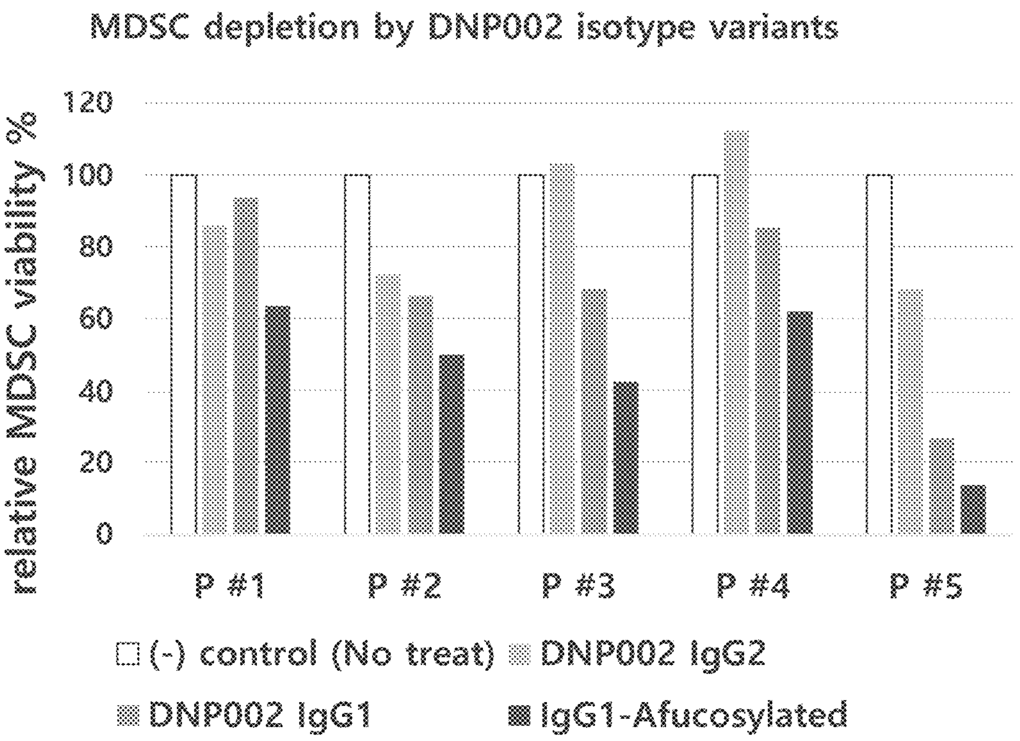
【FIG. 12a】
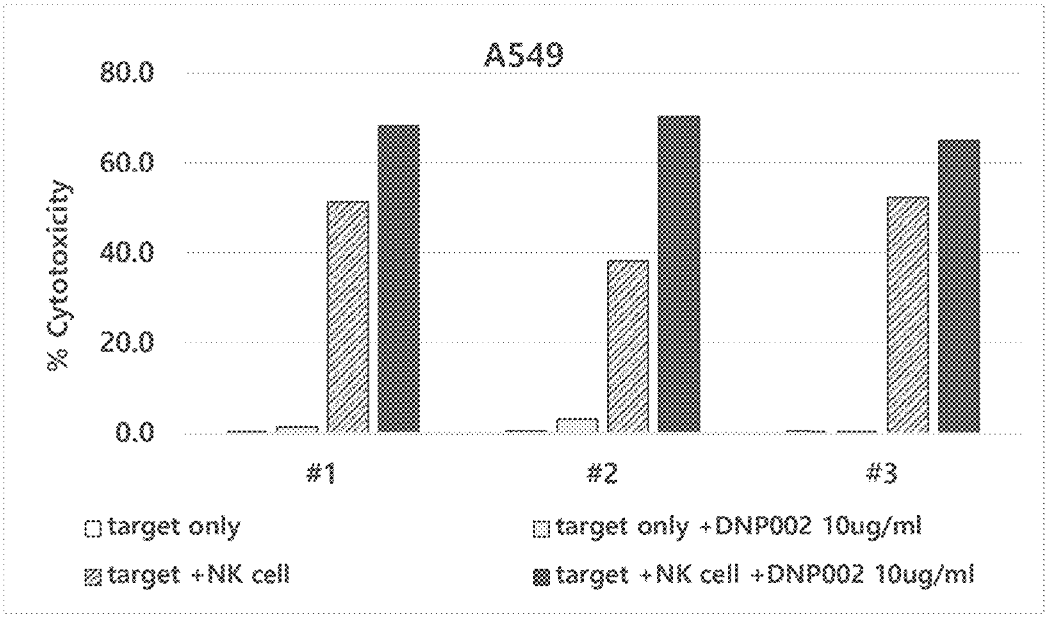

【FIG. 12b】
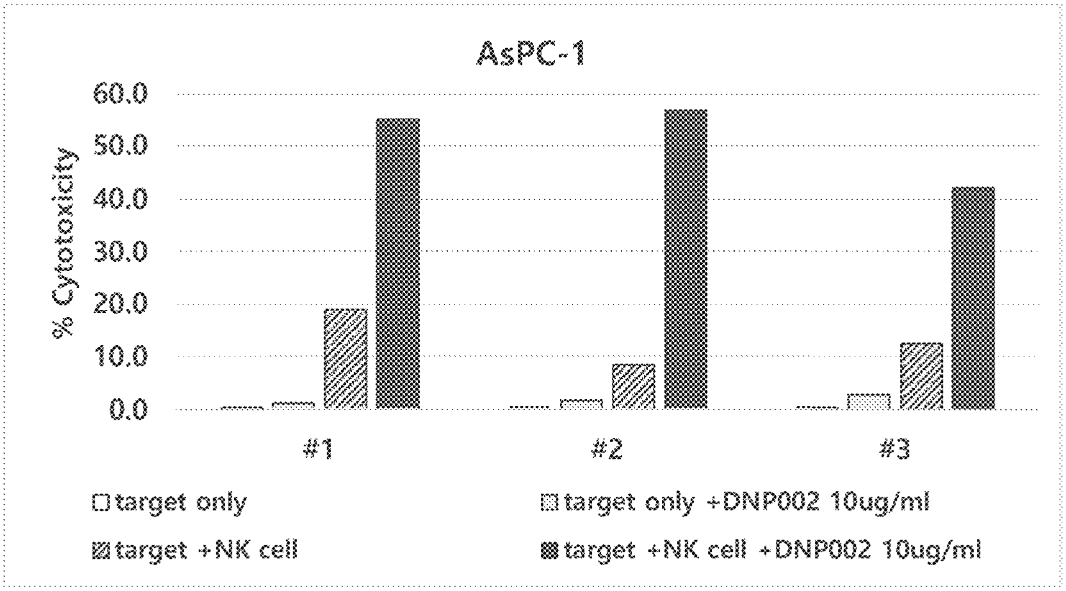

【FIG. 13】
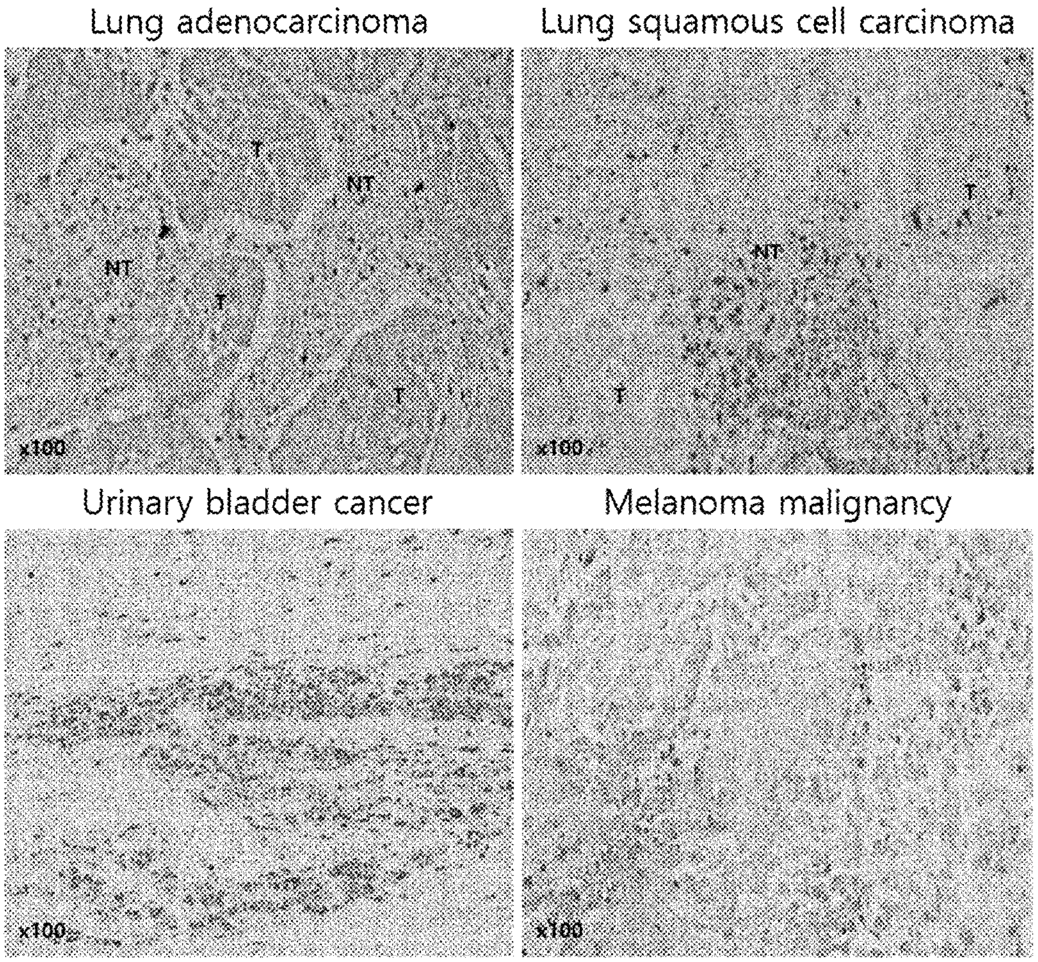
* T : tumor region, NT : no tumor region.

USE FOR PREVENTING AND TREATING MYELOID-DERIVED SUPPRESSOR CELL-RELATED DISEASES

TECHNICAL FIELD

The present invention relates to an immune-enhancing agent comprising an antibody or an antigen-binding fragment thereof specifically binding to CD66c which is expressed in myeloid-derived suppressor cell (MDSC), and a use of prevention, improvement or treatment for MDSC-related diseases using the immune-enhancing agent. Specifically, the present invention provides a use of prevention, improvement or treatment, or a use of diagnosis for MDSC-related diseases, by regulating production, death, or activity with a monoclonal antibody, so as to reduce an immunosuppressive activity of MDSC.

RELATED ART

The studies on immunotherapy using antibodies or immune cell vaccines have been actively conducted in the treatment of cancer recently. However, the immune evasion and suppression action of cancer cells inhibit the therapeutic effects. Cancer cells reduce the activity of various immune cells for the purpose of preventing an immune response to themselves, and induce cells with immune suppression functions such as inactive dendritic cells, regulatory T cells (Treg), and Tumor-associated macrophages (TAM). As one of the immunosuppressive cells, the role of myeloid-derived suppressor cells (MDSCs) has been recently gained great attention.

MDSC is defined as a collection of bone marrow-derived immature bone marrow cells with immunosuppressive function. It is reported that they are accumulated in peripheral blood, lymphatic organs, spleen, and cancer tissues in pathological conditions such as chronic/acute infections and cancer, although the number of MDSC is limited in healthy individuals.

MDSC can also promote the growth of cancer cells, and induce remote metastasis of cancer cells, by inhibiting the immune response of T cells and NK cells and inducing the generation of Treg cells which are immunosuppressive cells.

The immunosuppression mechanisms of MDSC known so far can be divided into four major types. The first is to be deficient in nutrients required by lymphocytes. The second is to generate oxidative stress, which inhibits various steps such as of proliferation to function of T cell by making active oxygen or active nitrogen. The third is to affect the trafficking and survival of lymphocytes. Specifically, the mechanisms such as inhibiting the recirculation process of T cells to lymph nodes, preventing the movement of T cells to the center of a tumor, and inducing T cell death are known. Fourth, it is known to proliferate antigen-specific natural Treg cells and promote the process of converting naïve CD4+ T cells to Tregs.

One of the greatest features of MDSC is its diversity in form, phenotype, and function. As the markers for MDSC, Lineage(−), HLA-DRLOW/(−), CD11b(+), and CD33(+) are known. Since these markers are commonly expressed in several different types of myeloid cells such as dendritic cells, macrophages, and precursor cells of granular leukocytes, MDSC has been defined as a group of myeloid-derived cells with immune suppression functions. This diversity of MDSC has led to different analyzes in studying the origins and characteristics of MDSCs, thereby causing great confusion of the study. Accordingly, a study has been conducted to clarify the subgroups of MDSC, to currently find that MDSC consists of 80% of granulocytic MDSCs and 20% of monocytic MDSCs. These two cell types differ not only in shape and phenotype, but also in the mechanism of suppressing immunity. The granulocytic MDSC induces antigen-specific immunosuppression through contact between T cells via active oxygen. The monocytic MDSC exhibits immunosuppressive function mainly by using high expression of arginase and various immunosuppressive cytokines.

Recent studies have reported that the accumulation of MDSC is involved in the immunosuppressive environment occurred in cancer patients, which is common in almost all cancer types. It is supported by many studies that the degree of increase in MDSC becomes higher as the stage of cancer progresses. Accordingly, studies to use the increase degree of MDSC as a prognostic marker for the low survival rate and treatment response rate of cancer patients are actively underway. It seems clear that MDSC plays an important role in the pathophysiology of cancer.

DISCLOSURE

Technical Problem

An embodiment of the present invention is an immune-enhancing agent, and immune-activating agent, or a composition for reducing or eliminating an immunosuppressive activity of MDSC, comprising an antibody or an antigen-binding fragment thereof specifically binding to CD66c which is expressed in myeloid-derived suppressor cell (MDSC).

An embodiment of the present invention is a pharmaceutical composition or a use for prevention, improvement or treatment of MDSC-related diseases comprising an antibody or an antigen-binding fragment thereof specifically binding to CD66c which is expressed in MDSC.

An embodiment of the present invention is a method of enhancing or activating an immune response of a subject, comprising administering an antibody or an antigen-binding fragment thereof specifically binding to CD66c which is expressed in MDSC, to the subject in need of.

An additional embodiment of the present invention is a method of inhibiting an activity of MDSC, comprising contacting MDSC with an antibody or an antigen-binding fragment thereof specifically binding to CD66c which is expressed in MDSC.

In addition, an embodiment of the present invention is a method of prevention, improvement or treatment of MDSC-related diseases, comprising administering an immune-enhancing agent, and immune-activating agent comprising an antibody or an antigen-binding fragment thereof specifically binding to CD66c which is expressed in myeloid-derived suppressor cell, to a subject with MDSC-related diseases.

The antibody or antigen-binding fragment thereof specifically binding to CD66c which is expressed in myeloid-derived suppressor cell in accordance with the present invention, eliminates or reduces an immunosuppressive activity of MDSC, decreases the number of MDSC, regulates an activity, production or cell death of MDSC, or induces the cell death.

Technical Solution

The present invention relates a use of immune-enhancement, immune-activation, or reduction or elimination of an immunosuppressive activity of MDSC, comprising an antibody or an antigen-binding fragment thereof specifically binding to CD66c which is expressed in MDSC.

An further embodiment of the present invention relates to a use of prevention, improvement or treatment of MDSC-related diseases, for examples cancers, infective diseases, and the like, comprising an antibody or an antigen-binding fragment thereof specifically binding to CD66c which is expressed in MDSC.

Specifically, the present invention relates a use of prevention, treatment or diagnosis of MDSC-related diseases, by inducing the reduction of immunosuppressive activity of MDSC.

The antibody may be a monoclonal antibody or a monoclonal antibody, and may be a mouse antibody, chimeric antibody, or humanized antibody.

Another embodiment provides a nucleic acid molecule encoding the anti-CD66c antibody or antigen-binding fragment thereof.

Another embodiment provides a recombinant vector comprising the nucleic acid molecule. The recombinant vector may be used as an expression vector for expressing the nucleic acid molecule in a host cell.

Further embodiment provides a recombinant cell comprising the nucleic acid molecule or the recombinant vector. The recombinant cell may be obtained by transforming the nucleic acid molecule or the recombinant vector into a host cell.

Another embodiment provides a method of preparing the anti-CD66c antibody or antigen-binding fragment thereof. The preparing method may include a step of expressing the nucleic acid molecule in a host cell. The step of expressing may include culturing the recombinant cells, and optionally, may further include separating and/or purifying the antibody from the obtained cell culture. The method may include the following steps:

(a) preparing a recombinant cell transformed with the nucleic acid molecule or the recombinant vector;

(b) culturing the recombinant cell under conditions and/or a period for sufficient expression of the nucleic acid molecule; and (c) separating and/or purifying the anti-CD66c antibody or antigen-binding fragment thereof from the culture obtained in step (c).

Hereinafter, the present invention will be described in more detail.

In one embodiment, the preparing method relates to a composition for reducing or eliminating an immune-suppressing ability of MDSC, an immune-enhancing agent, or an immune activating agent, including an antibody or antigen-binding fragment thereof that binds to CD66c expressed in MDSC.

MDSC promotes the growth of cancer cells, and can also induce remote metastasis of cancer cells by inhibiting the immune response of T cells and NK cells, and inducing the generation of Treg cells, which are immunosuppressive cells. The immunosuppression mechanisms of MDSC known so far are to deficient nutrients required by lymphocytes, to affect the trafficking and survival of lymphocytes, to generate oxidative stress, which inhibits various steps such as of proliferation to function of T cell by making active oxygen or active nitrogen, and to induce the cell death of T cells. In addition, MDSC has been known to proliferate antigen-specific natural Treg cells and promote the process of converting naïve CD4+ T cells to Tregs.

MDSC is defined as a collection of bone marrow-derived immature bone marrow cells with immunosuppressive function. Although the number is limited in healthy individuals, it is accumulated in peripheral blood, lymphatic organs, spleen, and cancer tissues in pathological conditions such as chronic/acute infections and cancer. MDSC accumulation and immunosuppressive function in carcinoma have been reported in colon cancer, fibrosarcoma, thymoma, lung cancer, mesothelioma, lymphoma, prostate cancer, head and neck cancer, melanoma and the like (Gabrilovich D I, et al., Coordinated regulation of myeloid cells by tumors, Nat Rev Immunol. 12(4):253-68 (2012)). Besides the cancers, MDSC accumulation has been known to induce immunosuppression in infections such as *Trypanosoma cruzi, Listeria monocytogenes, Leishmania major*, helminths, *Candida albicans, Porphyromonas gingivalis*, and the like, or diseases of toxoplasmosis and polymicrobic sepsis (Garbrilovich D I, et al. al., Myeloid-derived suppressor cells as regulators of the immune systems. Nat Rev Immunol. 9(3): 162-74 (2009)).

In the present disclosure, MDSC which is a phenotype of a non-lymphatic HLA-DRLow/(−), CD11b+, and CD33+, and expresses CD66c, can be a target of the anti-CD66c antibody or antigen-binding fragment thereof according to the present invention. Particularly, the present invention can target for the accumulation of CD66c positive MDSCs among MDSCs which is a phenotype of a non-lymphatic HLA-DRLow/(−), CD11b+ and CD33+, and thus present a plan for improvement or treatment of immunity deficiency, immunity decrease, immunity damage caused by MDSC. For example, MDSC can be designated by designating monocytic region and granulocytic regions in reference to the cell size in dot plot, except lymphocyte, selecting groups of no or lower expression level of HLA-DR, and selecting groups of CD11b and CD33 positive.

The present invention can provide a pharmaceutical composition or a use thereof for prevention, improvement or treatment of MDSC-related diseases, using an antibody or an antigen-binding fragment thereof specifically binding to CD66c which is expressed in MDSC.

The lysis effect of MDSC by the anti-CD66c antibody according to the present invention can induce a decreased number of MDSC cells or apoptosis in CEACAM6-positive cells in both whole blood and PMBC. Preferably, the anti-CD66c antibody can induce a decreased number or cell death in a ADCC manner. In whole blood, neutrophils positive for CEACAM6 target antigen and MDSC are mixed, and thus it is difficult to say that only MDSCs are selectively lysed. However, it is possible to perform selective lysis of MDSC by using anti-CD66c antibody, in peripheral blood mononuclear cells (PBMC) obtained after removing the neutrophil.

The MDSC-related diseases is a disease that exhibits immunosuppressive activity by MDSC, and is a disease in which the level of CD66c-positive MDSCs are increased compared to those of normal cells, which is a criterion used for determining the disease. For example, the number or the activity of CD66c-positive MDSCs in a subject with a specific disease is about 200% or more, about 300% or more, about 500% or more, about 700% or more, about 1,000% or more, or about 1,500% or more, for example, about 200 to 5,000%, or 200% to 3,000%, 200 to 1,500%, and the like, based on 100% of the number or activity of CD66c-positive MDSCs per unit volume of the corresponding normal subject sample. For example, the increase in the number of MDSCs can be determined by taking samples, such as bloods from a subject suspected of having MDSC-related diseases and a normal subject, analyzing the number of MSDCs in sample with a flow cytometer, and comparing the number of MDSCs of the subject suspected of having MDSC-related diseases, with that of normal subject. Specifically, in the subject having MDSC-related diseases, the number of MSDCs per unit volume of a sample (e.g. blood) may be increased compared to that of a normal subject, and for example, it may be about 200% or more, about 300% or more, about 500% or more, about 700% or more, about 1,000% or more, about 1,500% or more, for example, about 200 to 5,000%, or 200% to 3,000%, 200 to 1,500%, and the like, based on 100% of the number or activity of MDSCs per unit volume of the sample of corresponding normal subject.

Specifically, the MDSC-related diseases are for example, diseases which are accumulated MDSCs showing the phenotype of non-lymphatic HLA-DRLow/(−), CD11b+, and CD33+, and expressing CD66c among MDSCs, and the increased number of the MDSC compared to that of normal cells. The examples of MDSC-related diseases include chronic/acute infections, cancers and the like, specifically chronic/acute infections, cancers and the like which shows the immunosuppressive activity of MDSC. For example, the diseases may be chronic/acute infections, cancers and the like in which CD66c-positive MDSC among the MDSCs showing the phenotype of non-lymphatic HLA-DRLow/(−), CD11b+, and CD33+ are accumulated.

The MDSC-related infective diseases may be infections such as *Trypanosoma cruzi, Listeria monocytogenes, Leishmania major*, helminths, *Candida albicans*, or *Porphyromonas gingivalis*, or diseases of toxoplasmosis or polymicrobic sepsis.

For example, the MDSC-related cancer may be a cancer with increased CD66c-positive MDSC, and includes solid cancer and hematologic cancer. The examples of the solid cancer include colon cancer, fibrosarcoma, thymoma, lung cancer, mesothelioma, lymphoma, prostate cancer, head and neck cancer, melanoma, stomach cancer, liver cancer, or breast cancer, or preferably colon cancer, stomach cancer, or liver cancer. The use of the prevention, inhibition, or treatment of cancer and cancer metastasis can, for example, inhibit cancer cell growth. Example of the hematopoietic malignancy includes acute myeloid leukemia, acute lymphoblastic leukemia, acute monocytic leukemia, Hodgkin's lymphoma, and non-Hodgkin's lymphoma.

The present invention relates to an antibody or antigen-binding fragment thereof that binds to CD66c expressed in MDSC. CD66c (Cluster of Differentiation 66c) is also known as CEACAM 6 (carcinoembryonic antigen-related cell adhesion molecule 6) or NCA (non-specific cross—It is a protein also known as reacting glycoprotein antigen)-90, and is known as an important protein associated with cell adhesion. CD66c may preferably be represented by the amino acid sequence of SEQ ID NO: 1 (Genbank Protein No. AAH05008), but is not limited thereto.

As used herein, the term, "antibody" means a substance produced by stimulation of an antigen in the immune system, and the kind thereof is not particularly limited. The antibody may be generated in a non-natural manner, for example, recombinantly or synthetically generated. The antibody may be an animal antibody (e.g., mouse antibody, etc.), a chimeric antibody, a humanized antibody or a human antibody. The antibody may be a monoclonal antibody or a polyclonal antibody.

The anti-CD66c antibody or antigen-binding fragment specifically binds to a specific epitope of CD66c described above, and can be selected from the group consisting of animal antibodies (e.g., mouse antibodies), chimeric antibodies, humanized antibodies, and antigen-binding fragments thereof. The animal antibody may be derived from an animal species other than human, for example, rat, mouse, goat, guinea pig, donkey, rabbit, horse, llama, camel, bird (e.g., chicken, duck, etc.), but not limited thereto. Techniques for producing chimeric antibodies and/or humanized antibodies from such animal antibodies are well known in the art. The humanized antibody may be any suitable isotype such as IgG (IgG1, IgG2, IgG3, IgG4), IgM, IgA, IgD, IgE or any subclass, preferably IgG1 or IgG2 isotype, or more preferably de-fucosylated IgG1 or IgG2 isotype.

In addition, herein, an antibody can be understood to include an antigen-binding fragment of an antibody having antigen-binding ability, unless otherwise specified. In the present specification, the term, "complementarity determining regions (CDR)" refers to a region of antibody that imparts the binding specificity of antibody to an antigen among variable regions of the antibody. The antigen-binding fragment of the antibody described above may be an antibody fragment comprising at least one of the complementarity determining regions. The term, "CDR (complementarity determining region)" means an amino acid sequence of the hypervariable region of the heavy chain sand light chain of an immunoglobulin. Each of the heavy chain and light chain may comprise three CDRs (CDRH1, CDRH2, CDRH3 and CDRL1, CDRL2, CDRL3). The CDRs can provide key contact residues for the antibody to bind to an antigen or epitope. On the other hand, in the present disclosure, the terms "specifically bind" or "specifically recognize" means the same as those commonly known to those skilled in the art.

The term "antigen-binding fragment" refers to a fragment thereof for the entire structure of an immunoglobulin, and refers to a portion of a polypeptide including a portion to which an antigen can bind. For examples, the fragments may be scFv, (scFv)2, scFv-Fc, Fab, Fab' or F(ab')2, but not limited thereto.

The anti-CD66c antibody according to the present invention specifically recognizes and/or binds to CD66c, and the antibody includes a mouse antibody, chimeric antibody or humanized antibody. The chimeric antibody in the present invention is an antibody that the sequence of the variable region is derived from one species and the sequence of the constant region is derived from other species, for example, that the variable region is derived from mouse and the constant region is derived from human. The humanized antibody in the present invention is an antibody which has a low immunogenicity in human and an activity of non-human antibody. For example, it can be prepared by keeping non-human CDR region and substituting the rest of the region with human counterparts. For example, the literature is referenced: Morrison et al, Proc. Natl. Acad. ScL USA, 81:6851-6855(1984); Morrison and Oi, Adv. Immunol., 44:65-92 (1988); Verhoeyen et al, Science, 239:1534-1536 (1988); Padlan, Molec. Immun., 28:489-498 (1991); Padlan, Molec. Immun., 31(3):169-217 (1994).

The antibody fragment in the present invention is not limited, as long as it recognizes specifically CD66c epitope and includes variable region of a light chain ($V_L$) and variable region of a heavy chain ($V_H$). It can be selected from a group consisting of Fab, Fab', F(ab')2, scFv, dsFv and CDR. Especially, scFv is an antibody fragment prepared as a single chain by connecting the variable region of a heavy chain ($V_H$) and variable region of a light chain ($V_L$) with a linker polypeptide.

The term "hinge region" is a region included in the heavy chain of an antibody, exists between the CH1 and CH2 regions, and refers to a region to provide flexibility of the antigen binding site in the antibody. For example, the hinge may be derived from a human antibody, and specifically, may be derived from IgA, IgE, or IgG, such as IgG1, IgG2, IgG3, or IgG4.

The anti-CD66c antibody may be a monoclonal antibody or a polyclonal antibody, such as a monoclonal antibody. Monoclonal antibodies can be prepared according to methods well known in the art. For example, it can be manufactured using a phage display technique.

Unlike mouse antibodies or chimeric antibodies, the humanized antibodies showed 10 times higher stability than chimeric 8F5 antibodies in terms of stability in addition to the different characteristic that significantly reduces the cause of immunogenicity when administered to humans. Specifically, at a high temperature, for example, 62° C., the antibody has a high stability because the fluorescence variability against the ANS reagent was less than 200%.

The chimeric 8F5 and the humanized antibody increase the activation of T cells, which is also shown in increased activity of T cell caused by T cell activator and T cell activity conditions due to mixing of allogeneic dendritic cells and T cells of different people. This induction of T cell activation induces the death of cancer cells when co-cultured with cancer cells, and T cell activation under co-culture conditions with various cancer cells.

The antibody or fragment thereof according to the present invention has a tumor regression activity and a direct inhibitory effect on tumor cell lines. In the present disclosure, the tumor regression includes inducing or promoting a decrease in the size of a tumor and/or inhibiting, stopping or reducing the growth of tumor cells. For example, the reduction in tumor size means that the tumor size obtained by administering the composition comprising the antibody or fragment thereof is 97% or less, 95% or less, 90% or less, 85% or less, 80% or less, and 75% or less, based on 100% before treatment of the composition comprising the antibody or fragment thereof of the present invention.

The antibody according to the present invention has antibody-dependent cell-mediated cytotoxicity (ADCC) and complement-dependent cytotoxicity (CDC), and preferably ADCC characteristics.

The antibody or antigen-binding fragment thereof according to the present invention can improve or treat MDSC-related diseases by using a combination of natural killer cell or NK cell-derived cell therapy.

Specifically, the anti-CD66c antibody according to the present invention increases cancer cell killing ability by combination with natural killer cells, and thus, has an excellent effect of NK cells or NK cell therapeutic agents for effective removal of not only CEACAM6-positive cancer cells, but also CEACAM6-positive MDSCs.

In a specific experiment, as a result of measuring cell viability using the EZ-cytox enhanced cell viability kit (Daeil Lab), it was confirmed that the apoptosis effect by the combination of natural killer cells was higher in two types of cancer cell lines compared to the case of single treatment. It was confirmed (FIGS. 12*a* and 12*b*). According to the comparison of the selective lysis of MDSC by the anti-CD66c antibody of the present invention with those of combined anti-CD66c antibody and NK cells or NK cells, the combination therapy removed two types of cell lines including CEACAM6-positive cancer cell lines and CEACAM6-positive MDSCs.

By using the selective lysis of MDSC by the anti-CD66c antibody according to the present invention and the combined effect of NK cells or NK cell therapeutic agents, both CEACAM6-positive cancer cells and CEACAM6-positive MDSCs can be targeted and eliminated. The anti-CD66c antibody according to the present invention shows ADCC against different target cells, such as MDSC and cancer cells, respectively. In the case of cancer patients in which two types of cells are actually increased together, the anti-CD66c antibody of the present invention can remove the two types of targets together, and shows increased efficacy of simultaneous removal of cancer cells and MDSC targets, in combination with NK cell therapeutics.

The antibody according to the present invention may remove partially or completely fucose as a sugar residue bound to the antibody. The fucose-removing antibody of the present invention has an apoptosis activity of MDSC, and in one embodiment, the antibody of the present invention has an apoptosis activity of MDSC as a low fucose form or afucose form compared to a fucose form of antibody, so as to have high immunity enhancement. As used herein, "normal fucose" or "normal fucose content" refers to an antibody having a fucose content of at least 90% typically. The low fucose or afucose form of the antibody according to the present invention may be an antibody having a fucose content of about 10% or less, about 7% or less, or about 5% or less, for example, 0 to about 10%, 0 To about 7%, or 0 to about 5%.

Specifically, the antibody of the present invention can comprises the following complementarity determining regions (CDRs):

CDR-H1 comprising an amino acid sequence of SEQ ID NO: 1 or SEQ ID NO: 9,

CDR-H2 comprising an amino acid sequence of SEQ ID NO: 2 or SEQ ID NO: 10,

CDR-H3 comprising an amino acid sequence of SEQ ID NO: 3,

CDR-L1 comprising an amino acid sequence of SEQ ID NO: 4, SEQ ID NO: 11 or SEQ ID NO: 12, CDR-L2 comprising an amino acid sequence of SEQ ID NO: 5 and CDR-L3 comprising an amino acid sequence of SEQ ID NO: 6 or SEQ ID NO: 13.

The heavy chain variable region of the antibody comprises at least one selected from the group consisting of framework sequence (V-FR1) including the amino acid sequence of SEQ ID NOs: 22, 23, 24, 25, 26 or 27, framework sequence (V-FR2) including the amino acid sequence of SEQ ID NOs: 32, 33, 34, 35, 36 or 37, framework sequence (V-FR3) including the amino acid sequence of SEQ ID NOs: 42, 43, 44, 45, 46 or 47, and framework sequence (V-FR4) including the amino acid sequence of SEQ ID NOs: 52, 53, 54, 55, 56 or 57.

The light chain variable region of the antibody comprises at least one selected from the group consisting of framework sequence (L-FR1) including the amino acid sequence of SEQ ID NOs: 28, 29, 30 or 31, framework sequence (L-FR2) including the amino acid sequence of SEQ ID NOs: 38, 39, 40 or 41, framework sequence (L-FR3) including the amino acid sequence of SEQ ID NOs: 48, 49, 50, or 51, and framework sequence (L-FR1) including the amino acid sequence of SEQ ID NOs: 58, 59, 60 or 61.

The antibody comprises a heavy chain variable region including the amino acid sequence of SEQ ID NOs: 7, 14, 15, 16, 17 or 18, and a light chain variable region including the amino acid sequence of SEQ ID NOs: 8, 19, 20, or 21.

An example of a mouse antibody or a chimeric antibody according to the present invention can be an antibody or antigen-binding fragment thereof including at least one selected from the group consisting of an amino acid sequence of VH CDR comprising the amino acid sequences of SEQ ID NOS: 1 to 3 and an amino acid sequence of VL CDR comprising amino acid sequences of SEQ ID NOs: 4 to 6. The CDRs and the variable regions of an example of the mouse antibody or chimeric antibody are summarized in Table 1 below.

Specifically, an example of the antibody of the present invention may include SEQ ID NO: 1 (CDR1), SEQ ID NO: 2 (CDR2) and SEQ ID NO: 3 (CDR3) as VH CDR and/or SEQ ID NO: 4 (CDR1), SEQ ID NO: 5 (CDR2), and SEQ ID NO: 6 (CDR3) as VL CDR.

The mouse antibody or chimeric antibody may comprise a VH region including the amino acid sequence of SEQ ID NO: 7 and a VL region including the amino acid sequence of SEQ ID NO: 8.

The present invention relates to a pharmaceutical composition, a kit or a method of prevention or treatment of a MDSC-related disease and a symptom thereof, comprising a mouse antibody or chimeric antibody as an active ingredient.

The present invention also relates to a pharmaceutical composition for prevention or treatment of a MDSC-related disease and a symptom thereof, comprising a mouse antibody or chimeric antibody as an active ingredient, for example an anti-CD66c antibody or antigen-binding fragment thereof including CDR-H1, CDR-H2, CDR-H3, CDR-L1, CDR-L2, and CDR-L3 of the antibody produced by a hybridoma cell deposited as an accession number of KCLRF-BP-00230. The hybridoma cell was deposited with the Korean Cell Line Research Foundation (KCLRF) as '8F5' on Feb. 22, 2010 and received an accession number of KCLRF-BP-00230, which has been described in detail in KR 10-1214177.

The present invention can prepare a humanized antibody by using the amino acid sequence of anti-CD66c antibody 8F5 in the mouse antibody or chimeric antibody and the framework sequences of human. From the candidates of recombinant humanized antibodies are selected on the basis of expression degree, aggregation, and degree of cell binding, where the expression occurs normally, the protein aggregation is very little due to the instability of the protein itself is small, and of similar binding ability to the target antigen-positive cell. Specifically, the cell binding profile is similar to that of the chimeric antibody and is obtained by multiplying positive rate of antibody positivity (% gated) with the average fluorescence (mean), then is compared with the chimeric antibody to select the candidate antibodies within the range of ±20% (Example 2). Therefore, when CDR region sequences of the mouse antibody are inserted into the framework region of human antibody at the time of preparing the humanized antibody, the binding ability of prepared antibody is rapidly decreased due to the change of the original protein structure. In consideration of the decrease of the binding ability of prepared antibody, the selected humanized antibodies of the present invention are very excellent antibody.

Preferably, five types of recombinant humanized antibodies exhibiting a high binding affinity based on the cell binding ability as compared to the chimeric antibody are selected and subjected to binding assay for CD66c antigen and similar antigen to CD66 antigen by ELISA.

In addition, the humanized antibody according to the present invention exhibits excellent stability compared to the chimeric antibody, for example, an antibody having stability which is reflected as ANS reactivity variation of less than 200%. The ANS reactivity variation of less than 200% is regarded as a very small variation and the higher variation value than 200% can be interpreted as observing ANS reactivity due to the significant structural change of protein. Accordingly, the humanized antibody according to the present invention has similar antigen binding activity and cell binding ability to the chimeric antibody, and the increased physical stability of the antibody protein itself, which can be very excellent in terms of druggability of the therapeutic antibody.

The fluorescence variation of the antibody against the ANS reagent can be measured by dividing the difference between the fluorescence value measured at low temperature conditions (e.g, 4° C.) and the fluorescence value measured at high temperature conditions (e.g, 62° C.) with the fluorescence value measured at low temperature conditions.

[Mathematic Equation]

Fluorescence variation=(fluorescence value measured at high temperature condition−fluorescence value measured at low temperature condition)/(fluorescence value measured at low temperature condition)

As a method for obtaining a specific fluorescence variation of antibody, the reactivity of ANS reagent was measured by a fluorescent reader after being left for 4 hours at a refrigeration condition (4° C.) and a temperature of 62° C., and expressed as a fluorescence value, and the fluorescence variation can be obtained using the equation.

Examples of the humanized antibody according to the present invention may include one or more amino acid sequences selected from the group consisting of amino acid sequences that determine the CDRs of the heavy chain variable region or light chain variable region comprising the amino acid sequences of SEQ ID NOs: 9 to 13. The examples of mouse antibody and the chimeric antibody ma include one or more amino acid sequences selected from the group consisting of amino acid sequences that determine the CDRs of the heavy chain variable region comprising the amino acid sequences of SEQ ID NOs: 1 to 3 or light chain variable region comprising the amino acid sequences of SEQ ID NOs: 4 to 6.

Specifically, an example of a humanized antibody includes an amino acid sequence determining the CDR1 of the VH region comprising the amino acid sequence of SEQ ID NO: 1 or 9, an amino acid sequence determining the CDR2 of the VH region comprising the amino acid sequence of SEQ ID NO: 2 or 10, and the CDR3 of the VH region comprising the amino acid sequence of SEQ ID NO: 3.

Examples of the humanized antibody include an amino acid sequence determining the CDR1 of the VL region including the amino acid sequence of SEQ ID NO: 4, 11 or 12, an amino acid sequence determining the CDR2 of the VL region including the amino acid sequence of SEQ ID NO: 5, and an amino acid sequence determining the CDR3 of the VL region comprising the amino acid sequence of SEQ ID NO: 6 or 13.

Examples of the humanized antibody include a heavy chain variable region selected from the group consisting of the amino acid sequence of SEQ ID NO: 7 and SEQ ID NOs: 14 to 18 and a light chain variable region selected from the group consisting of the amino acid sequence of SEQ ID NO: 8 and SEQ ID Nos: 19-21, but does not include the antibody comprising SEQ ID NO: 7 and SEQ ID NO: 8.

The CDR sequences and variable region sequences according to an example of the humanized antibody are summarized in Table 1 below.

TABLE 1

| Name | SEQUENCE | SEQ ID NO |
|---|---|---|
| 8F5-chimeric $V_H$-CDR1 | ASGYSFTDYTMN | 1 |
| 8F5-chimeric $V_H$-CDR2 | LINPFHGGTVSNQRFKV | 2 |
| 8F5-chimeric $V_H$-CDR3 | VRGDPVRHYYALAY | 3 |
| 8F5-chimeric $V_L$-CDR1 | GASENVYGTLN | 4 |
| 8F5-chimeric $V_L$-CDR2 | GATNLAD | 5 |
| 8F5-chimeric $V_L$-CDR3 | VATYYCQNVLSAPYT | 6 |
| 8F5-chimeric $V_H$ | EVQLQQSGPELVKPGASMKISCKASGYSFTDYTMNWVKQSHGKNLEWIGLINPFHGGTVSNQRFKVKATLTVDVSSNTAYMELLSLTSDDSAVYYCVRGDPVRHYYALAYWGQGTSVTVSS | 7 |
| 8F5-chimeric $V_L$ | DIQMTQSPASLSASVGETVTITCGASENVYGTLNWYQRKQGKSPQLLIYGATNLADGMSSRFSGSGSGRQYSLKISSLHPDDVATYYCQNVLSAPYTFGGGTKLEII | 8 |
| 8F5-human $V_H$-CDR1 | ASGYSFTDYTMN | 1 |
| 8F5-human $V_H$-CDR1 | ASGYSFTDYTM**H** | 9 |
| 8F5-human $V_H$-CDR2 | INPFHGGTVSNQRFKV | 2 |
| 8F5-human $V_H$-CDR2 | LINPF**G**GST**SYA**Q**K**FK**G** | 10 |
| 8F5-human $V_H$-CDR3 | VRGDPVRHYYALAY | 3 |
| 8F5-human $V_L$-CDR1 | GASENVYGTLN | 4 |
| 8F5-human $V_L$-CDR1 | GASENVYGTL**A** | 11 |
| 8F5-human $V_L$-CDR1 | **R**ASENVYGTLN | 12 |
| 8F5-human $V_L$-CDR2 | GATNLAD | 5 |
| 8F5-human $V_L$-CDR3 | VATYYCQNVLSAPYT | 6 |
| 8F5-human $V_L$-CDR3 | **F**ATYYCQNVLSAPYT | 13 |
| 8F5-human-VH5 | QVQLVQSGAEVKKPGASVKISCKASGYSFTDYTMNWVRQAHGQNLEWIGLINPFHGGTVSNQRFKVKATLTVDVSTNTAYMELSRLRSDDTAVYYCVRGDPVRHYYALAYWGQGTLVTVSS | 14 |
| 8F5-human-VH6 | QVQLVQSGAEVKKPGASMKISCKASGYSFTDYTMNWVKQAPGQNLEWIGLINPFHGGTVSNQRFKVKATLTVDVSTNTAYMELSRLRSDDTAVYYCVRGDPVRHYYALAYWGQGTLVTVSS | 15 |
| 8F5-human-VH7 | QVQLVQSGAEVKKPGASMKISCKASGYSFTDYTMNWVRQAPGQGLEWIGLINPFHGGTVSNQRFKVKATLTVDVSTNTAYMELSRLRSDDTAVYYCVRGDPVRHYYALAYWGQGTLVTVSS | 16 |
| 8F5-human-VH10 | QVQLVQSGAEVKKPGASVKVSCKASGYSFTDYTMNWVKQAPGQNLEWIGLINPFHGGTVSNQRFKVKATMTVDVSTNTAYMELSRLRSDDTAVYYCVRGDPVRHYYALAYWGQGTLVTVSS | 17 |
| 8F5-human-VH11 | QVQLVQSGAEVKKPGASVKISCKASGYSFTDYTMHWVKQAPGQNLEWIGLINPFGGSTSYAQKFKGRVTMTRDTSTNTAYMELSRLRSDDTAVYYCVRGDPVRHYYALAYWGQGTLVTVSS | 18 |

TABLE 1-continued

| Name | SEQUENCE | SEQ ID NO |
|---|---|---|
| 8F5-human-VK5 | DIQMTQSPSTLSASVGDRVTITCGASENV<br>YGTLAWYQRKPGKAPKLLIYGATNLADG<br>VPSRFSGSGSGREYTLTISSLQPDDFATYY<br>CQNVLSAPYTFGGGTKLEIK | 19 |
| 8F5-human-VK7 | DIQMTQSPSTLSASVGDRVTITCGASENV<br>YGTLNWYQRKPGKAPKLLIYGATNLADG<br>VPSRFSGSGSGTEYTLTISSLQPDDFATYY<br>CQNVLSAPYTFGGGTKLEIK | 20 |
| 8F5-human-VK8 | DIQMTQSPSTLSASVGDRVTITCRASENV<br>YGTLNWYQRKPGKAPKLLIYGATNLADG<br>MPSRFSGSGSGTEYTLTISSLQPDDFATYY<br>CQNVLSAPYTFGGGTKLEIK | 21 |

The framework sequences of one example of a humanized antibody according to the present invention are shown in Tables 2 and 3 below, wherein said antibody may include at least one selected from the group consisting of frameworks 1 to 4 of the heavy chain variable region and frameworks 1 to 4 of the light chain variable region And may be an antibody comprising one or more frameworks.

Specifically, the amino acid sequence of framework 1 of in the heavy chain variable region may comprise SEQ ID NOS: 23 to 27, the amino acid sequence of framework 2 may comprise SEQ ID NOS: 32 to 37, and the amino acid sequence of framework 3 43 to 47, and the amino acid sequence of Framework 4 may include SEQ ID NOS: 53 to 57.

In the light chain variable region, the amino acid sequence of Framework 1 may comprise SEQ ID Nos: 29 to 31, the amino acid sequence of Framework 2 may comprise SEQ ID NOs: 39 to 41, and the amino acid sequence of Framework 3 may correspond to the amino acid sequence of SEQ ID NOs: 49-51, and the amino acid sequence of Framework 4 may comprise SEQ ID NOs: 59 to 61. The framework sequences according to examples of the humanized antibody are shown in the following table.

TABLE 2

| Name | FR1 | SEQ ID NO | FR2 | SEQ ID NO |
|---|---|---|---|---|
| $V_H$-Chimeric | EVQLQQSGPELVKPGAS<br>MKISCK | 22 | WVKQSHGKNLE<br>WIG | 32 |
| VH5 | **Q**VQL**V**QSG**A**E**VK**KPGA<br>S**V**KISCK | 23 | WV**R**Q**A**HG**Q**NLE<br>WIG | 33 |
| VH6 | **Q**VQL**V**QSG**A**E**VK**KPGA<br>SMKISCK | 24 | WVKQ**AP**G**Q**NLE<br>WIG | 34 |
| VH7 | **Q**VQL**V**QSG**A**E**VK**KPGA<br>SMKISCK | 25 | WV**R**Q**AP**G**QG**LE<br>WIG | 35 |
| VH10 | **Q**VQL**V**QSG**A**E**VK**KPGA<br>S**V**K**V**SCK | 26 | WVKQ**AP**G**Q**NLE<br>WIG | 36 |
| VH11 | **Q**VQL**V**QSG**A**E**VK**KPGA<br>S**V**KISCK | 27 | WVKQ**AP**G**Q**NLE<br>WIG | 37 |
| $V_L$-Chimeric | DIQMTQSPASLSASVGET<br>VTITC | 28 | WYQRKQGKSPQL<br>LIY | 38 |
| VK5 | DIQMTQSP**ST**LSASVG**D**<br>**R**VTITC | 29 | WYQRK**P**GK**A**P**K**L<br>LIY | 39 |
| VK7 | DIQMTQSP**ST**LSASVG**D**<br>**R**VTITC | 30 | WYQRK**P**GK**A**P**K**L<br>LIY | 40 |
| VK8 | DIQMTQSP**ST**LSASVG**D**<br>**R**VTITC | 31 | WYQRK**P**GK**A**P**K**L<br>LIY | 41 |

TABLE 3

| Name | FR1 | SEQ ID NO | FR2 | SEQ ID NO |
|---|---|---|---|---|
| $V_H$-Chimeric | NQRFKVKATLTVDVSSNTAYMELLSLTSDDSAVYYCVR | 42 | WGQGTSVTVSS | 52 |
| VH5 | NQRFKVKATLTVDVSTNTAYMELSRLRSDDTAVYYCVR | 43 | WGQGTLVTVSS | 23 |
| VH6 | NQRFKVKATLTVDVSTNTAYMELSRLRSDDTAVYYCVR | 44 | WGQGTLVTVSS | 24 |
| VH7 | NQRFKVKATLTVDVSTNTAYMELSRLRSDDTAVYYCVR | 45 | WGQGTLVTVSS | 55 |
| VH10 | NQRFKVKATMTVDVSTNTAYMELSRLRSDDTAVYYCVR | 46 | WGQGTLVTVSS | 56 |
| VH11 | AQKFKGRVTMTRDTSTNTAYMELSRLRSDDTAVYYCVR | 47 | WGQGTLVTVSS | 57 |
| $V_L$-Chimeric | GMSSRFSGSGSGRQYSLMSSLHPDD | 48 | FGGGTKLEII | 58 |
| VK5 | GVPSRFSGSGSGRQYSLMSSLHPDD | 49 | FGGGTKLEIK | 59 |
| VK7 | GVPSRFSGSGSGTEYTLTISSLQPDD | 50 | FGGGTKLEIK | 60 |
| VK8 | GMPSRFSGSGSGTEYTLTISSLQPDD | 51 | FGGGTKLEIK | 61 |

The humanized antibody may comprise a VH region selected from the group consisting of the amino acid sequences of SEQ ID NOs: 14 to 18 and a VL region selected from the group consisting of the amino acid sequences of SEQ ID NOs: 19 to 21. Specifically, the examples of the humanized antibody include an antibody (Vk8+VH6) comprising a VH region including the amino acid sequence of SEQ ID NO: 15 and a VL region comprising the amino acid sequence of SEQ ID NO: 21, an antibody (Vk8+VH11) comprising a VH region including an amino acid sequence of SEQ ID NO: 18 and a VL region comprising the amino acid sequence of SEQ ID NO: 21, an antibody (Vk5+VH7) comprising a VH region including the amino acid sequence of SEQ ID NO: 16, and a VL region comprising the amino acid sequence of SEQ ID NO: 19, an antibody (Vk7+VH6) comprising a VH region including the amino acid sequence of SEQ ID NO: 17 and a VL region comprising the amino acid sequence of SEQ ID NO: 20, an antibody (Vk7+VH10) comprising a VH region including the amino acid sequence of SEQ ID NO: 15, and a VL region comprising the amino acid sequence of SEQ ID NO: 20, an antibody (Vk7+VH7) comprising a VH region comprising the amino acid sequence of SEQ ID NO: 16 and a VL region comprising the amino acid sequence of SEQ ID NO: 20, an antibody (Vk7+VH5) comprising a VH region comprising the amino acid sequence of SEQ ID NO: 14 and a VL region comprising the amino acid sequence of SEQ ID NO: 20, and an antibody (Vk8+VH7) comprising a VH region comprising the amino acid sequence of SEQ ID NO: 16 and a VL region comprising the amino acid sequence of SEQ ID NO: 21. Specific combinations and amino acid sequences of the antibodies are shown in Table 6 below. The preferred examples of antibody include an antibody (Vk8+VH6) comprising a VH region including the amino acid sequence of SEQ ID NO: 15 and a VL region comprising the amino acid sequence of SEQ ID NO: 21, an antibody (Vk8+VH11) comprising a VH region including an amino acid sequence of SEQ ID NO: 18 and a VL region comprising the amino acid sequence of SEQ ID NO: 21, an antibody (Vk5+VH7) comprising a VH region including the amino acid sequence of SEQ ID NO: 16, and a VL region comprising the amino acid sequence of SEQ ID NO: 19, an antibody (Vk7+VH6) comprising a VH region including the amino acid sequence of SEQ ID NO: 17 and a VL region comprising the amino acid sequence of SEQ ID NO: 20, and an antibody (Vk7+VH10) comprising a VH region including the amino acid sequence of SEQ ID NO: 15, and a VL region comprising the amino acid sequence of SEQ ID NO: 20.

The anti-CD66c antibody or fragment thereof may be coupled to various labeling agents, toxins, or anti-tumor drugs. It will be apparent to those skilled in the art that the antibody of the invention can be coupled to a labeling agent, a toxin, or an anti-tumor drug by a method well known in the art. Such coupling may be chemically conducted on the site of attachment after expression of the antibody or antigen. Alternatively, the coupling product may be engineered into the antibody or antigen of the invention at the DNA level. Subsequently, the product may be expressed in a suitable host system as described herein below, and the expressed proteins are collected and, if necessary, renatured. The coupling may be performed via a linker that has been known in the art. In particular, various linkers that release a toxin or an anti-tumor drug under acidic or reductive conditions or upon exposure to specific proteases may be used with this technology. In some embodiments, it may be desirable that the linker is attached to the labeling agent, toxin, or anti-tumor drug via spacer arms in various lengths to reduce potential steric hindrance.

An antibody to an antigen-determining region of CD66c or a fragment thereof, may be produced using a typical method with a CD66c protein, an antigen-determining region of CD66c, a portion of CD66c containing an antigen-determining region of CD66c, or a cell expressing an antigen-determining region of CD66c serving as an antigen. For example, a method for producing an anti-CD66c antibody can be achieved through a method for producing a cell line producing an anti-CD66c antibody, comprising (a) injecting and immunizing an animal with a CD66c protein, an antigen-determining region of CD66c, a portion of CD66c containing an antigen-determining region of CD66c, or a cell expressing an antigen-determining region of CD66c, (b) obtaining splenocytes producing an antibody specific for CD66c, and (c) fusing the splenocytes with myeloma cells to give hybridoma cells and selecting a hybridoma cell producing an antibody to CD66c. The antibody can be isolated by culturing the cell line in vitro or by introducing the cell line in vivo. For example, the cell line may be intraperitoneally injected into mice, followed by isolating and purifying the antibody from the ascites. Isolation and purification of monoclonal antibodies may be achieved by subjecting the culture supernatant and ascites to ion exchange chromatography (DEAE or DE52) or affinity chromatography using an anti-immunoglobulin column or protein A column.

The antigen-determining region to which the antibody of the present invention binds exhibits MDSC-specific expression. Hence, the anti-CD66c antibody can not only be effectively used to detect MDSC, but can also exert cytotoxicity only on tumor cells when it carries a toxic substance.

Another embodiment provides a use of the anti-CD66c antibody according to the present invention as a marker for detection of MDSC, or specifically a use of detecting MDSC, diagnosing MDSC-related diseases, or providing information on diagnosis of MDSC-related diseases, using the antibody or antigen-binding fragment thereof against CD66c.

For example, it provides a composition for detection of MDSC containing a substance that interacts with the antigen-determining region of the antibody by using the antibody or antigen-binding fragment thereof against CD66c. The interacting substance includes all substances being capable of interact with the antigen-determining region CD66c, and can be at least one selected from small molecular chemicals, antibodies, antigen-binding fragments of antibodies, aptamers, and the like.

The diagnostic composition of the present invention is useful in the detection of undesired expression or over-expression of CD66c in various cells, tissues or another suitable sample, by contacting a sample with an antibody of the present invention and determining the presence of a CD66c in the sample. Accordingly, the diagnostic composition of the invention may be available for assessing the onset or status of disease, as defined herein below. In particular, MDSC being capable of expressing CD66c can be targeted with the antibody of the present invention, or a fragment or derivative thereof. The cells which have bound the antibody of the present invention might be attacked by immune system functions such as the complement system or by cell-mediated cytotoxicity, and thus reduces the number of or completely eradicating the cells showing undesired expression or over-expression of CD66c.

As a specific example, a method or a composition for diagnosis MDSC-related diseases using the antibody or antigen-binding fragment for CD66c according to the present invention is provided.

In the case of diagnosing MDSC-related diseases, for example cancer, the antibody against CD66c or antigen-binding fragment thereof according to the present invention can be used for diagnosis and treatment by targeting MDSC infiltrated around cancer tissues regardless of the expression of CEACAM 6 antigen in cancer tissues or cancer cells. The antibody against CD66c according to the present invention not only binds to CD66c expressed in solid cancer cells, but also binds to CD66c expressed in MDSC, and thus, can detect the cancer by targeting the increased state of MDSC caused by cancer, even in cancers that do not express CD66c in solid cancer cells. Specifically, in cancer tissues of lung adenocarcinoma which is CEACAM6 positive in cancer cells, and lung squamous cell carcinoma, urinary bladder cancer, and melanoma malignancy which are CEACAM6 negative in cancer cells, the result of staining the cancer tissue confirmed that CEACAM 6-positive MDSC were in the non-tumor site of the cancer tissue (FIG. 13).

Accordingly, the patients with cancer show the increased level of MDSCs regardless of the CEACAM 6 positivity in the surface of cancer cells, and thus, as shown in the result of Example 8, MDSC infiltrated into the cancer microenvironment can be detected and confirmed. When considered together with the results of Example 5.2 showing that MDSC can be selectively dissolved, this indicates that MDSC can be used as a target for diagnosis and treatment purposes regardless of the CEACAM6 positivity on cancer cells. Although the presence or absence of CEACAM6 expression on the surface of cancer cells may vary depending on the cancer type, MDSCs are increased in most cancer types regardless of CEACAM6 expression. Thus, the anti-CD66c antibody according to the present invention can target MDSC and can be used for diagnostic and therapeutic purpose in various applications.

In another embodiment, the antibody of the present invention, or a fragment or derivative thereof is coupled to a labeling agent. Such antibodies are particularly suitable for diagnostic applications.

The composition of the invention can be administered as an active agent alone or in combination with other agents.

A still further embodiment of the present invention relates to a method for detecting MDSC, which comprises (a) reacting the anti-CD66c antibody with a sample including MDSC, and (b) determining that the sample is MDSC if the sample is positive to the antibody. The sample may include, but is not limited to, lymphoid fluid, bone marrow, blood, and blood corpuscles. When used for screening MDSC, the anti-CD66c antibody may be conjugated with a label capable of indicating antigen-antibody reactivity. The label useful for this purpose may include a radioisotope, a fluorescent, a luminescent, a chromogen, and a dye.

Also, the anti-CD66c antibody of the present invention may be provided for a kit for diagnosing MDSC-related diseases. The diagnostic kit may comprise a means for detecting an antigen-antibody reaction in addition to the anti-CD66c antibody. The detecting means may be an agent useful for performing a technique selected from the group consisting of flow cytometry, immunohistochemical staining, enzyme-linked immunosorbent assay (ELISA), radioimmunoassay (RIA), enzyme immunoassay (EIA), fluorescence immunoassay (FIA), and luminescence immunoassay (LIA).

The therapeutic effect of the solid cancer are the effects of suppressing the cancer exacerbation including not only the growth inhibition (quantitative reduction) and apoptosis effect of cancer cells (especially cancer stem cells) or cancer tissues including the same, as well as migration, invasion, metastasis, etc. In order to maximize the effect of the antibody according to the present invention, the antibody can be treated in combination with STING agonist or 5-Fu, which can be expected to obtain a higher effect in combination treatment.

As used herein the term “subject” or “patient” refers to a mammal, including a primate such as a human, a monkey, etc., and a rodent such as a mouse, a rat, etc., that is afflicted with, or has the potential to be afflicted with MDSC-related diseases or symptom and thus which is in need of alleviation, prevention, and/or treatment of the MDSC.

The administration of the antibody or its fragment according to the present invention may be conducted in any acceptable manner. For example, a therapeutic agent including the anti-CD66c antibody as an active ingredient is administered orally or parenterally, and preferably parenterally, to a subject, e.g., a human or an animal that has MDSC-related diseases. The therapeutic agent may include a pharmaceutically acceptable excipient, and the dose of the therapeutic agent may vary depending on the condition of the patient, and may range from, for example, 3 mg to 6,000 mg per day. The therapeutic agent may take such forms as liquids, powders, emulsions, suspensions or injections, but is not limited thereto.

Further, the present invention provides a method for treating MDSC-related diseases, using at least one selected from among an antibody to an antigen-determining region of CD66c, a fragment of the antibody (F(ab')2, Fab, Fv, etc.), and a ligand to an antigen-determining region of CD66c. An antibody or a fragment thereof may be monoclonal or polyclonal, and may be derived from humans or animals. The anti-CD66c antibody or its fragment may further comprise the toxin described above. The toxin may be fused, coupled, conjugated or linked to the antibody using a well-known technique.

The pharmaceutical composition of the present invention may be administered as a single active agent or in combination with any other agents that are preferable for the treatment of the disease of interest. In addition, the antibody of the present invention may be used in conjunction with other anticancer therapies, such as chemotherapy, radiotherapy, cytotherapy, etc. The well-known various anticancer agents may be used in chemotherapy or cytotherapy.

Effect of Invention

The present invention provides to an immune-enhancing agent comprising an antibody specifically binding to CD66c which is expressed in myeloid-derived suppressor cell (MDSC) or an antigen-binding fragment thereof, and a use of the immune-enhancing agent for prevention, improvement or treatment of MDSC-related diseases.

BRIEF DESCRIPTION OF DRAWINGS

FIG. 1 shows the result of cloning a gene of antibody from mouse 8F5 antibody and expressing it as a chimeric recombinant antibody and binding to the surface of CD66c antigen-positive A549 cells.

FIGS. 2A to 2C show the results of HPLC analysis of eight kinds of recombinant humanized antibodies selected first among 96 kinds of recombinant humanized antibodies. The results are shown as left measured at OD 220 nm and right measured at OD 280 nm for each antibody. The result represent whether the aggregation of antibodies and the impurities derived from antibody such as fragments are or not.

FIGS. 3*a* to 3*e* show similar degree of cell surface binding of recombinant humanized antibodies as compared to chimeric antibodies, as a result of confirming CD66c antigen positive cell surface binding of eight recombinant humanized antibodies firstly selected among 96 recombinant humanized antibodies FIGS. 4*a* and 4*b* show results of ELISA analysis for the binding ability of the five recombinant humanized antibodies selected from 96 recombinant humanized antibodies to the CD66c antigen. FIG. 4*a* shows the results for the CECACAM6 (CD66c) as an antigen and FIG. 4*b* shows the result for the CEACAM1 (CD66a) antigen.

FIGS. 5*a* and 5*b* show results of evaluating the antibody stability at a severe temperature condition for five recombinant humanized antibodies selected from among 96 recombinant humanized antibodies.

FIGS. 6*a* to 6*d* show the cell surface binding of CD66c antigen positive cell A549 of recombinant humanized antibodies expressed in CHO cell.

FIG. 7 is a schematic diagram for helping understanding of the MDSC analysis method and specifically a schematic diagram of the specific dot plot obtaining by designating only the monocyte and granulocyte regions excluding lymphocytes according to the size of the cells in dot-plot, selecting the groups with no or low expression of HLA-DR, and determining the group that is positive for CD11b and CD33 among the groups as MDSCs in the upper part, and the result of the positivity rate of DNP002 among the determined MDSC group in the lower part.

FIG. 8 is a representative result of analyzing the MDSC killing effect after treatment with DNP002, showing that MDSCs was significantly reduced by afucoslyated DNP002. CD66b is expressed in granulocytic MDSC, but not monocytic MDSC, and is used for MDSC subtype classification. Most of MDSCs designated in FIG. 8 were CD66b-positive and could be classified as granulocytic MDSCs. Thus, the granulocytic MDSCs were significantly reduced by treatment with DNP002.

FIG. 9 is a result of analyzing the MDSC killing effect after treatment with DNP002 by showing a result of comparing the percentage of the decreased number of MDSCs due to the DNP002 treatment in all five patients compared to the control group, where P #1 on the horizontal axis in the graph means patient’s whole blood #1, and the vertical axis represents a change in the relative MDSC viability % change.

FIG. 10 shows a result of analyzing the MDSC killing effect using a flow cytometer after treating PBMCs isolated from blood of stomach cancer patient with DNP002 antibody.

FIG. 11*a* is a result of comparing the MDSC killing effect according to the isotype of DNP002, confirming that DNP002 in afucosylated IgG1 type induces MDSC killing in the blood most effectively.

FIG. 11*b* is a result of comparing the MDSC killing effect in five stomach patients according to the isotype of DNP002, by showing that DNP002 in afucosylated IgG1 type provides highest MDSC killing effect in the blood of five stomach patients from the result of comparing the percentage of the MDSC killing effect where P #1 on the horizontal axis in the graph means patient's whole blood #1, and the vertical axis represents a change in the relative MDSC viability % change.

A3600), sequenced to confirm the DNA sequence, and the mouse antibody gene was identified through the IMGT site (www.imgt.org). The heavy chain variable region sequences and light chain variable region sequences of the analyzed 8F5 antibody are as follows.

TABLE 4

| Name | sequence | SEQ ID NO |
|---|---|---|
| 8F5-chimeric $V_H$-CDR1 | ASGYSFTDYTMN | 1 |
| 8F5-chimeric $V_H$-CDR2 | LINPFHGGTVSNQRFKV | 2 |
| 8F5-chimeric $V_H$-CDR3 | VRGDPVRHYYALAY | 3 |
| 8F5-chimeric $V_L$-CDR1 | GASENVYGTLN | 4 |
| 8F5-chimeric $V_L$-CDR2 | GATNLAD | 5 |
| 8F5-chimeric $V_L$-CDR3 | VATYYCQNVLSAPYT | 6 |
| 8F5-chimeric $V_H$ | EVQLQQSGPELVKPGASMKISCKASGYSFTDYTMNWVKQS<br>HGKNLEWIGLINPFHGGTVSNQRFKVKATLTVDVSSNTAY<br>MELLSLTSDDSAVYYCVRGDPVRHYYALAYWGQGTSVTVS<br>S | 7 |
| 8F5-chimeric $V_L$ | DIQMTQSPASLSASVGETVTITCGASENVYGTLNWYQRKQG<br>KSPQLLIYGATNLADGMSSRFSGSGSGRQYSLKISSLHPDDV<br>ATYYCQNVLSAPYTFGGGTKLEII | 8 |
| 8F5-chimeric $V_H$ | Gaggtccagctgcaacagtctggacctgaactggtgaagcctggagcttcaatgaagatatcc<br>tgcaaggcttctggttactcattcactgactacaccatgaactgggtgaagcagagccatggaa<br>agaaccttgagtggattggacttattaatcctttccatggtggtactgtctccaaccagaggttcaa<br>ggtcaaggccacattaactgtagacaagtcatccaacacagcctacatggagctcctcagtctg<br>acatctgacgactctgcggtctattactgtgtaagaggtgacccggtccgccattactatgattg<br>gcctactggggtcagggaacctcagtcaccgtctcctca | 62 |
| 8F5-chimeric $V_L$ | gacatccagatgactcagtctccagcttcactgtctgcatctgtgggagaaactgtcaccatcac<br>atgtggagcaagtgagaatgtttacggtactttaaattggtatcagcggaaacagggaaaatctc<br>ctcagctcctgatctatggtgcaaccaacttggcagatggcatgtcatcgaggttcagtggcagt<br>ggttctggtagacagtattctc | 63 |

FIG. 12*a* and FIG. 12*b* are the results of the apoptosis effect analyzed under the conditions of DNP002 antibody alone, NK cells alone, and combination of DNP002 antibody and NK cells on stomach cancer cell line A549 and pancreatic cancer cell line AsPC-1 which are positive for CEACAM6 as a target antigen.

FIG. 13 is a picture showing the presence of CEACAM6-positive MDSCs in non-tumor site of the cancer tissue by performing CEACAM6 immunostaining of cancer tissues of lung adenocarcinoma in which CEACAM6 is positive in cancer cells, and lung squamous cell carcinoma, urinary bladder cancer and skin cancer (Melanoma malignancy) in which CEACAM6 is negative in cancer cells themselves.

MODE FOR THE INVENTION

A better understanding of the present invention may be obtained through the following examples which are set forth to illustrate, but are not to be construed as limiting the present invention.

Example 1: Preparation of Anti-CD66c Chimeric Antibody 1.1. Gene Sequence Cloning of Anti-CD66c Antibody The 8F5 antibody gene was cloned using Mouse Ig-Primer Set (Millipore, Cat. #: 69831). The RNA isolated from the 8F5 hybridoma was PCR using the mouse Ig-primer set, inserted into a pGem-T vector (Promega, Cat. #:

1-2. Production of Chimeric Antibody

Based on the amino acid sequence of the constructed anti-CD66c mouse antibody 8F5, an anti-CD66c chimeric antibody was prepared.

1-2-1. Plasmid Production

For expressing the anti-CD66c chimeric antibody, a plasmid for heavy chain and a light chain expression plasmid were respectively prepared. POptiVEC (Invitrogen) vector was used as the light chain expression plasmid, and pcDNA3.3 (Invitrogen) vector was used as the heavy chain expression plasmid.

In order to express the variable region coding cDNA and the constant region coding cDNA of each antibody as a continuous amino acid sequence without additional amino acid insertion, the coding sequence of the cloned variable region and the known human IgG1 constant region (heavy chain) and the kappa constant region (light chain) coding sequences were synthesized (Bioneer). The synthesized heavy gene and light chain gene were cut with restriction enzymes Xho I and Sal I and the light chain gene fragment was ligated to the pOptiVec vector and the heavy chain gene fragment was ligated to the pcDNA3.3 vector, respectively, to construct a complete antibody expression plasmid (pcDNA3.3-anti-CD66c heavy chain expression plasmid and pOptiVEC-anti-CD66c light chain expression plasmid).

1-2-2. Transfection

The prepared pcDNA3.3-anti-CD66c heavy chain expression plasmid and pOptiVEC-anti-CD66c light chain expression plasmid were transfected into CHO cell-derived DG44 cells (Invitrogen).

Three days prior to transfection, DG44 cells in suspension were adapted to MEMS medium containing 5% FBS to convert them into adherent cells and to improve transfection efficiency. Transfection was performed on a 6-well plate using the ViaFect transfection regent (Promega, Cat. #: E4981). On the day before the transfection, DG44 cells adapted to the adhered state were prepared by subculturing at a concentration of $1\times10^5$ cells/well. The amount of DNA used for transfection was determined by using pcDNA3.3-anti-CD66c heavy chain expression plasmid and pOptiVEC-anti-CD66c light chain expression plasmids were used at an amount of 2 ug and 1.5 ug respectively at a ratio of 1.5:1. Transfection was carried out for 48 hours. Flow cytometry was used to analyze the transfected cell population. As shown in FIG. 1, the expression of chimeric antibody was confirmed by A549 non-small cell lung cancer cell line. FIG. 1 shows the result of cloning an antibody gene from mouse 8F5 antibody and expressing it as a recombinant chimeric antibody and binding to the surface of CD66c antigen-positive A549 cells.

Example 2: Preparation of Humanized Anti-CD66c Monoclonal Antibody

2.1 Selection of Recombinant Antibody Sequence by in Silico Humanization

CDRs (CDRH1: ASGYSFTDYTMN) SEQ ID NO: 1, CDRH2: SEQ ID NO: 2 (LINPFHGGTVSNQRFKV); CDRH3: SEQ ID NO: 3 (VRGDPVRHYYALAY); CDRL1: SEQ ID NO: 4 (GASENVYGTL); CDRL2: SEQ ID NO: 5 (GATNLAD); If CDR3: SEQ ID NO: 6 (VATYYCQNVLSAPYT) of the heavy chain of the mouse anti-CD66c antibody, 8F5 (heavy chain amino acid sequence: SEQ ID NO: 7, heavy chain encoding DNA: SEQ ID NO: 62; light chain amino acid sequence: SEQ ID NO: 8; light chain encoding DNA: SEQ ID NO: 63) were maintained as close to the antigen binding affinity as possible, or if the antigen binding affinity is equal or superior, the recombinant humanized antibody sequences based on the sequence of the framework region based on the germline sequence encoding the human antibody gene in silico method. The germline gene of human antibody used as a backbone of the recombinant humanized antibody sequence is most similar to the heavy chain and light chain of the mouse CD66c antibody 8F5, respectively, as shown in Table 5. The amino acid sequence and the nucleic acid sequence of the heavy chain variable region and the light chain variable region of the mouse CD66c antibody and the CDR sequences of the heavy chain variable region and the light chain variable region are shown in Table 6.

TABLE 5

| Human Ab Germline | |
|---|---|
| Heavy chain | Light chain |
| IGHV1-69-2*01 | IGKV1-27*01 |
| IGHV1-2*02 | IGKV1-5*01 Homo sapiens |
| IGHV1-46*01 | IGKV1-39*01 Homo sapiens |

Twelve (12) heavy chain variable regions and eight (8) light chain variable regions were selected as the humanized 8F5 antibody sequence selected using the human antibody germline gene sequence, as shown in Table 3. The amino acid sequences of the heavy chain variable region and the light chain variable region, CDR sequences, and the framework sequences of the selected humanized antibody are shown in Tables 6 to 8. The heavy chain variable region and the light chain variable region of the chimeric antibody and the humanized antibody are shown in Table 1. It is preferable that the mouse antibody and the humanized antibody have the same amino acid sequences of heavy chain CDR3 and light chain CDR2. The bold and underlined parts in Table 6 are the CDR sequences of antibody. The bold and underlined parts in Table 7 indicate the modified amino acid.

TABLE 6

| Antibody number | combination | name | Amino acid sequence |
|---|---|---|---|
| 3043 | Vk8 + VH6 | VH6 | QVQLVQSGAEVKKPGASMKISCK**ASGYSFTDYTMN**WVKQAPGQNLE<br>WIG**LINPFHGGTVSNRFKV**KATLTVDVSTNTAYMELSRLRSDDTAV<br>YYCVR**GDPVRHYYALAY**WGQGTLVTVSS |
| | | Vk8 | DIQMTQSPSTLSASVGDRVTITC**RASENVYGTLN**WYQRKPGKAPKLLI<br>Y**GATNLAD**GMPSRFSGSGSGTEYTLTISSLQPDD**FATYYCQNVLSAPY**<br>**T**FGGGTKLEIK |
| 3058 | Vk8 + VH11 | VH11 | QVQLVQSGAEVKKPGASVKISCK**ASGYSFTDYTMH**WVKQAPGQNLE<br>WIG**LINPFGGSTSYAQKFKG**RVTMTRDTSTNTAYMELSRLRSDDTAV<br>YYCVRG**DPVRHYYALAY**WGQGTLVTVSS |
| | | Vk8 | DIQMTQSPSTLSASVGDRVTITC**RASENVYGTLN**WYQRKPGKAPKLLI<br>YGATNLADGMPSRFSGSGSGTEYTLTISSLQPDD**FATYYCQNVLSAPY**<br>**T**FGGGTKLEIK |
| 2938 | Vk5 + VH7 | VH7 | QVQLVQSGAEVKKPGASMKISCK**ASGYSFTDYTMN**WVRQAPGQGLE<br>WIG**LINPFHGGTVSNQRFKV**KATLTVDVSTNTAYMELSRLRSDDTAV<br>YYCVR**GDPVRHYYALAY**WGQGTLVTVSS |
| | | Vk5 | DIQMTQSPSTLSASVGDRVTITC**GASENVYGTLA**WYQRKPGKAPKLLI<br>YGATNLADGVPSRFSGSGSGREYTLTISSLQPDD**FATYYCQNVLSAPY**<br>**T**FGGGTKLEIK |
| 3007 | Vk7 + VH6 | VH6 | QVQLVQSGAEVKKPGASMKISCK**ASGYSFTDYTMN**WVKQAPGQNLE<br>WIG**LINPFHGGTVSNQRFKV**KATLTVDVSTNTAYMELSRLRSDDTAV<br>YYCVR**GDPVRHYYALAY**WGQGTLVTVSS |
| | | Vk7 | DIQMTQSPSTLSASVGDRVTITC**GASENVYGTLN**WYQRKPGKAPKLLI<br>Y**GATNLAD**GVPSRFSGSGSGTEYTLTISSLQPDD**FATYYCQNVLSAPY**<br>**T**FGGGTKLEIK |

TABLE 6-continued

| Antibody number | comb-ination | name | Amino acid sequence |
|---|---|---|---|
| 3019 | Vk7 + VH10 | VH10 | QVQLVQSGAEVKKPGASVKVSCK**ASGYSFTDYTMN**WVKQAPGQNLE WIG**LINPFHGGTVSNQRFKV**KATMTVDVSTNTAYMELSRLRSDDTAV YYCVR**GDPVRHYYALAY**WGQGTLVTVSS |
| | | Vk7 | DIQMTQSPSTLSASVGDRVTITC**GASENVYGTLN**WYQRKPGKAPKLLI Y**GATNLAD**GVPSRFSGSGSGTEYTLTISSLQPDD**FATYYCQNVLSAPY** **T**FGGGTKLEIK |
| 3010 | Vk7 + VH7 | VH7 | QVQLVQSGAEVKKPGASMKISCK**ASGYSFTDYTMN**WVRQAPGQGLE WIG**LINPFHGGTVSNQRFKV**KATLTVDVSTNTAYMELSRLRSDDTAV YYCVR**GDPVRHYYALAY**WGQGTLVTVSS |
| | | Vk7 | DIQMTQSPSTLSASVGDRVTITC**GASENVYGTLN**WYQRKPGKAPKLLI Y**GATNLAD**GVPSRFSGSGSGTEYTLTISSLQPDD**FATYYCQNVLSAPY** **T**FGGGTKLEIK |
| 3004 | Vk7 + VH5 | VH5 | QVQLVQSGAEVKKPGASVKISCK**ASGYSFTDYTMN**WVRQAHGQNLE WIG**LINPFHGGTVSNQRFKV**KATLTVDVSTNTAYMELSRLRSDDTAV YYCVR**GDPVRHYYALAY**WGQGTLVTVSS |
| | | Vk7 | DIQMTQSPSTLSASVGDRVTITC**GASENVYGTLN**WYQRKPGKAPKLLI Y**GATNLAD**GVPSRFSGSGSGTEYTLTISSLQPDD**FATYYCQNVLSAPY** **T**FGGGTKLEIK |
| 3046 | Vk8 + VH7 | VH7 | QVQLVQSGAEVKKPGASMKISCK**ASGYSFTDYTMN**WVRQAPGQGLE WIG**LINPFHGGTVSNQRFKV**KATLTVDVSTNTAYMELSRLRSDDTAV YYCVR**GDPVRHYYALAY**WGQGTLVTVSS |
| | | Vk8 | DIQMTQSPSTLSASVGDRVTITC**RASENVYGTLN**WYQRKPGKAPKLLI Y**GATNLAD**GMPSRFSGSGSGTEYTLTISSLQPDD**FATYYCQNVLSAPY** **T**FGGGTKLEIK |

TABLE 7

| Name | CDR1 | SEQ ID NO | CDR2 | SEQ ID NO | CDR3 | SEQ ID NO |
|---|---|---|---|---|---|---|
| $V_H$-Chimeric | ASGYSFTDYT MN | 1 | LINPFHGGTVSNQRF KV | 2 | GDPVRHYYALA Y | 3 |
| VH5, 6, 7, 10 | ASGYSFTDYT MN | 1 | LINPFHGGTVSNQRF KV | 2 | GDPVRHYYALA Y | 3 |
| VH11 | ASGYSFTDYT M**H** | 9 | LINPF**G**GST**SYA**Q**K**F K**G** | 10 | GDPVRHYYALA Y | 3 |
| $V_L$-Chimeric | GASENVYGTL N | 4 | GATNLAD | 5 | VATYYCQNVLS APYT | 6 |
| VK5 | GASENVYGTL **A** | 11 | GATNLAD | 5 | **F**ATYYCQNVLS APYT | 13 |
| VK7 | GASENVYGTL N | 4 | GATNLAD | 5 | **F**ATYYCQNVLS APYT | 13 |
| VK8 | **R**ASENVYGTL N | 12 | GATNLAD | 5 | **F**ATYYCQNVLS APYT | 13 |

TABLE 8

| Name | FR1 | SEQ ID NO | FR2 | SEQ ID NO | FR3 | SEQ ID NO | FR4 | SEQ ID NO |
|---|---|---|---|---|---|---|---|---|
| $V_H$-Chimeric | EVQLQQSGPEL VKPGASMKISC K | 22 | WVKQSHG KNLEWIG | 32 | NQRFKVKATLT VDVSSNTAYM ELLSLTSDDSA VYYCVR | 42 | WGQGTSV TVSS | 52 |
| VH5 | **Q**VQL**V**QSG**A**E **VK**KPGAS**V**KIS CK | 23 | WV**R**QAH G**Q**NLEWI G | 33 | NQRFKVKATLT VDVS**T**NTAYM EL**SRLR**SDD**T**A VYYCVR | 43 | WGQGT**L**V TVSS | 53 |

TABLE 8-continued

| Name | FR1 | SEQ ID NO | FR2 | SEQ ID NO | FR3 | SEQ ID NO | FR4 | SEQ ID NO |
|---|---|---|---|---|---|---|---|---|
| VH6 | QVQLVQSGAEVKKPGASMKISCK | 24 | WVKQAPGQNLEWIG | 34 | NQRFKVKATLTVDVSTNTAYMELSRLRSDDTAVYYCVR | 44 | WGQGTLVTVSS | 54 |
| VH7 | QVQLVQSGAEVKKPGASMKISCK | 25 | WVRQAPGQGLEWIG | 35 | NQRFKVKATLTVDVSTNTAYMELSRLRSDDTAVYYCVR | 45 | WGQGTLVTVSS | 55 |
| VH10 | QVQLVQSGAEVKKPGASVKVSCK | 26 | WVKQAPGQNLEWIG | 36 | NQRFKVKATMTVDVSTNTAYMELSRLRSDDTAVYYCVR | 46 | WGQGTLVTVSS | 56 |
| VH11 | QVQLVQSGAEVKKPGASVKISCK | 27 | WVKQAPGQNLEWIG | 37 | AQKFKGRVTMTRDTSTNTAYMELSRLRSDDTAVYYCVR | 47 | WGQGTLVTVSS | 57 |
| $V_L$-Chimeric | DIQMTQSPASLSASVGETVTITC | 28 | WYQRKQGKSPQLLIY | 38 | GMSSRFSGSGSGRQYSLKISSLHPDD | 48 | FGGGTKLEII | 58 |
| VK5 | DIQMTQSPSTLSASVGDRVTITC | 29 | WYQRKPGKAPKLLIY | 39 | GVPSRFSGSGSGRQYSLKISSLHPDD | 49 | FGGGTKLEIK | 59 |
| VK7 | DIQMTQSPSTLSASVGDRVTITC | 30 | WYQRKPGKAPKLLIY | 40 | GVPSRFSGSGSGTEYTLTISSLQPDD | 50 | FGGGTKLEIK | 60 |
| VK8 | DIQMTQSPSTLSASVGDRVTITC | 31 | WYQRKPGKAPKLLIY | 41 | GMPSRFSGSGSGTEYTLTISSLQPDD | 51 | FGGGTKLEIK | 61 |

2.2 Expression and Analysis of Recombinant Humanized Antibodies

The sequences of selected antibody were expressed in 293 cells in the form of human IgG1 by connecting the human IgG1 heavy chain constant region and the kappa light chain constant region, respectively. Seven days after the transfection, the recombinant humanized antibody was purified using KanCap A resin (Kaneca).

The purified antibody was quantitated by measuring at OD 280 nm and SDS-PAGE was performed. The purity and the aggregation of the antibody were analyzed by analyzing with 280 nm and 220 nm by HPLC using Sepax Zenix-C SEC-300 size exclusion column (Sepax Technologies) (FIGS. 2A to 2C)

2.3 Cell Binding and Antigen Binding Analysis of Recombinant Humanized Antibodies 2-3-1 Cell Binding Assay Each expressed 96 recombinant humanized antibody was poured and reacted in a test tube containing the same amount (1 ug) of CD66c-positive A549 non-small-cell lung cancer cell line at 4° C. for 30 minutes, washed with PBS, and treated with FITC-conjugated goat anti-Huma IgG (DiNona Inc, Korea) was added and incubated at 4° C. for 15 minutes. After washing with PBS, the cells were analyzed with a flow cytometer (Stratedigm, S1000EXi) and the results are shown below.

Among the 96 recombinant humanized antibody candidates, eight were firstly selected based on the degree of expression, the presence of aggregation, and the degree of cell binding (Table 9 and Table 10, FIGS. 3A to 3E). Tables 9 and 10 are the results of analysis of primary selected anti-CD66c humanized antibody and chimeric 8F5, and Table 10 shows the results of flow cytometer analysis.

TABLE 9

| No. | #71 | #86 | #93 | #43 | #51 | #45 | #41 | #74 |
|---|---|---|---|---|---|---|---|---|
| Protein ID | 3043 | 3058 | 2938 | 3007 | 3019 | 3010 | 3004 | 3046 |
| H & L조합 | Vk8 + VH6 | Vk8 + VH11 | Vk5 + VH7 | Vk7 + VH6 | Vk7 + VH10 | Vk7 + VH7 | Vk7 + VH5 | Vk8 + VH7 |
| Well | F11 | H2 | H9 | D7 | E3 | D9 | D5 | G2 |
| OD 280 nm | 3.54 | 3.86 | 3.32 | 4.01 | 4.03 | 3.5 | 3.56 | 3.54 |
| Volume (ml) | 0.25 | 0.25 | 0.25 | 0.25 | 0.25 | 0.25 | 0.25 | 0.25 |
| Conc. (mg/ml) | 2.52 | 2.71 | 2.36 | 2.85 | 2.86 | 2.49 | 2.53 | 2.52 |
| Yield(mg) | 0.66 | 0.71 | 0.61 | 0.74 | 0.74 | 0.65 | 0.66 | 0.66 |
| extinction coefficient | 102190 | 103680 | 102190 | 102190 | 102190 | 102190 | 102190 | 102190 |
| MW(Da) | 72750 | 72691 | 72616 | 72633 | 72521 | 72604 | 72669 | 7272 |

TABLE 10

| No. | Protein ID | H & L combination | % gated | Mean | % (% gated × mean) |
|---|---|---|---|---|---|
| Chimeric antibody | ** | ** | 73 | 619 | 100.0 |
| #71 | 3043 | Vk8 + VH6 | 69 | 686 | 104.8 |
| #86 | 3058 | Vk8 + VH11 | 72 | 645 | 102.8 |
| #93 | 2938 | Vk5 + VH7 | 71 | 611 | 96.0 |
| #43 | 3007 | Vk7 + VH6 | 71 | 565 | 88.8 |
| #51 | 3019 | Vk7 + VH10 | 70 | 561 | 86.9 |
| #45 | 3010 | Vk7 + VH7 | 70 | 554 | 85.8 |
| #41 | 3004 | Vk7 + VH5 | 71 | 541 | 85.0 |
| #74 | 3046 | Vk8 + VH7 | 71 | 523 | 82.2 |

Table 9 shows the degree of expression, the presence or absence of aggregation, and the degree of cell binding of 8 selected antibodies. Specifically, the expression levels and the molecular weights of the 8 selected antibodies were summarized. In addition, according to the results of flow cytometry in Table 10, it was confirmed that the eight recombinant humanized antibodies exhibited cell binding strengths of ±20% which showed very similar cell binding strength to chimeric antibodies. As a result, the 8 antibody being normally expressed and having few aggregations formed due to the instability of the protein itself, and the similar binding affinity to the target antigen-positive cells to the chimeric antibody were firstly selected from 96 humanized candidate antibodies As shown in FIG. 3, the actual cell binding profile was similar to that of chimeric antibody, and 8 kinds of humanized antibodies were determined by multiplying the antibody positivity (% gated) with the mean fluorescence (mean), and by the selecting the humanized antibodies within 20% compared with the chimeric antibody. In general, when the mouse antibody CDR region sequence is inserted into the framework region of the humanized antibody at the time of the production of the humanized antibody, the antibody binding affinity is sharply decreased due to the change of the original protein structure. In considering the general property of humanized antibody, very good humanized antibodies were be selected in the present invention.

2-3-2 Antigen Binding Assay

Among the eight selected recombinant humanized antibodies, five kinds of recombinant humanized antibodies exhibiting a high binding affinity as compared to that of the chimeric antibody were selected and analyzed for their binding affinity to CD66c antigen and similar CD66 antigens by ELISA, respectively.

TABLE 11

| Protein ID | HC & LC combination |
|---|---|
| 3043 | Vk8 + VH6 |
| 3058 | Vk8 + VH11 |
| 2938 | Vk5 + VH7 |
| 3007 | Vk7 + VH6 |
| 3019 | Vk7 + VH10 |

Antigen CD66c (CEACAM6; Sino Biological, Inc.) and CEACAM1 antigen (Sino Biological, Inc.) were coated on a 96-well plate at a rate of 100 ng per well and then blocked. The primary antibody was diluted 3-fold from 10 ug/ml and bound at 37° C. for 1 hour. The primary antibody was diluted three times from 10 ug/ml at initial concentration and was bound at 37° C. for 1 hour, and goat anti-Human Ig-HRP conjugate (Jackson ImmunoResearch) as a secondary antibody was diluted 1:10,000 and incubated at 37° C. for 30 minutes. The washing was carried out at three times between each step, and the TMB reaction was performed, stopped with 1N $H_2SO_4$ solution at the same amount of TMB solution (100 ul) and then OD value was measured at 450 nm.

As a result of the experiment, the binding affinities to CD66c antigen of the five kinds of recombinant humanized antibodies selected from among 96 kinds of recombinant humanized antibodies are shown in FIG. 4*a*, Table 12, FIG. 4*b* and Table 13. FIG. 4*a* and Table 12 show the binding capacity of the antibodies to CECACAM6 CD66c) antigen, and FIG. 4*b* and Table 13 are the results for the CEACAM1 (CD66a) antigen.

From the binding affinity of antibodies to the antigen in FIG. 4*a*, Table 12, FIG. 4*b* and Table 13, all antibodies to CECACAM6 showed a similar binding profile to the chimeric antibody to CEACAM6 and were divided into the groups that did not bind or bound weakly CEACAM1.

TABLE 12

| Antibody concentration (ng/ml) | chi 8F5 | hu 3043 | hu 3058 | hu 2938 | hu 3007 | hu 3019 |
|---|---|---|---|---|---|---|
| 10000.00 | 3.17 | 2.73 | 2.87 | 3.43 | 3.37 | 3.13 |
| 3333.33 | 3.41 | 2.95 | 3.18 | 3.27 | 3.24 | 3.26 |
| 1111.11 | 3.30 | 2.74 | 3.19 | 3.16 | 3.23 | 3.34 |
| 370.37 | 3.30 | 2.92 | 2.80 | 3.08 | 3.16 | 3.23 |
| 123.46 | 2.83 | 2.29 | 2.22 | 2.56 | 2.90 | 3.04 |
| 41.15 | 2.02 | 1.73 | 1.38 | 1.72 | 2.17 | 2.45 |
| 13.72 | 1.15 | 1.37 | 1.06 | 1.15 | 1.64 | 1.77 |
| 4.57 | 0.80 | 0.91 | 0.74 | 0.65 | 1.02 | 1.32 |
| 1.52 | 0.53 | 0.70 | 0.53 | 0.48 | 0.79 | 0.95 |
| 0.51 | 0.41 | 0.49 | 0.38 | 0.36 | 0.64 | 0.80 |
| 0.17 | 0.40 | 0.41 | 0.37 | 0.30 | 0.53 | 0.68 |

TABLE 13

| Antibody concentration (ng/ml) | chi 8F5 | hu 3043 | hu 3058 | hu 2938 | hu 3007 | hu 3019 |
|---|---|---|---|---|---|---|
| 10000.00 | 1.21 | 0.91 | 0.42 | 0.32 | 1.01 | 0.99 |
| 3333.33 | 1.24 | 1.22 | 0.31 | 0.27 | 1.15 | 1.07 |
| 1111.11 | 1.21 | 1.17 | 0.19 | 0.21 | 1.06 | 1.02 |
| 370.37 | 1.13 | 0.80 | 0.12 | 0.14 | 0.92 | 0.89 |
| 123.46 | 0.95 | 0.70 | 0.07 | 0.10 | 0.82 | 0.79 |
| 41.15 | 0.82 | 0.61 | 0.07 | 0.07 | 0.66 | 0.58 |
| 13.72 | 0.51 | 0.43 | 0.05 | 0.06 | 0.46 | 0.41 |
| 4.57 | 0.28 | 0.27 | 0.05 | 0.05 | 0.27 | 0.24 |
| 1.52 | 0.16 | 0.16 | 0.05 | 0.05 | 0.18 | 0.16 |
| 0.51 | 0.10 | 0.10 | 0.04 | 0.05 | 0.11 | 0.11 |
| 0.17 | 0.08 | 0.08 | 0.04 | 0.04 | 0.09 | 0.08 |

2.4 Stability Analysis of Recombinant Humanized Antibodies

The experiments were conducted to determine the stability of the antibodies by leaving the five recombinant humanized antibodies of Example 3.3 selected by the binding profile to antigen and cell under high temperature conditions.

The stability was determined by performing the binding experiments using 8-anilino-1-naphthalenesulfonic acid (ANS, Sigma). ANS is a compound that can detect the denaturation of proteins by measuring the change in fluorescence wavelength between the binding to and not binding to hydrophobic sites exposed when protein is denatured.

The recombinant humanized antibody was adjusted to a concentration of 0.2 mg/ml using PBS (phosphate buffered saline), and left at 50° C. for 4 hours under severe conditions. 0.2 μg/ml of ANS solution was mixed at 20 μl with 500 μl of the diluted solution of antibody to be analyzed dilution to be measured, and analyzed after 5 minutes later with a fluorescent reader at 360 nm excitation and 460 nm emission conditions. In addition, the ANS reagent reaction was also measured at a temperature of 70° C. for additional 30 minutes.

FIGS. 5*a* and 5*b* show the results of confirming the antibody stability of the five recombinant humanized antibodies shown in Table 11 under severe temperature conditions. That is, the reactivity of the ANS reagent was measured by fluorescence after leaving the antibody at 50° C. for 4 hours under the sever condition, and further left at 70° C. for 30 minutes. As shown in the results of the experiment of FIG. 5*a*, most 5 kinds antibodies showed little ANS response when the antibodies were left at the temperature of 50° C. for 4 hours, but the greatly increased fluorescence value of the antibodies when the antibodies were additional left at 70° C. for 30 minutes. Among them, the recombinant antibody having protein ID: 3058 exhibited the smallest increased fluorescence value, and thus showed the most stable property in the temperature change among the five recombinant humanized antibodies.

In order to measure the change rate of ANS reagent reactivity, ANS reagent reactivity was analyzed with a fluorescent reader in the same manner as above after leaving the antibodies for 4 hours at a refrigeration condition (4±2° C.) and a temperature of 62° C. The fluorescence value variability of the antibody against the ANS reagent can be determined by obtaining the difference between the fluorescence value measured at low temperature conditions (e.g., 4° C.) and the fluorescence value measured at high temperature conditions (e.g., 62° C.) and dividing with the fluorescence value measured at low temperature conditions.

[Mathematical Equation]

Fluorescence value variability=(fluorescence value measured at high temperature condition−fluorescence value measured at low temperature condition)/(fluorescence value measured at low temperature condition)

As shown in FIG. 5*b*, the reaction was allowed for 4 hours at a temperature of 62° C. which was somewhat increased from temperature (50° C.), and then the ANS reagent reactivity was confirmed. Five recombinant humanized antibodies and the chimeric antibodies showed little ANS response under refrigerated conditions, but increased with increasing temperature. However, Chimeric 8F5 antibody showed the reactivity of ANS reagent increased to 1,406% by keeping the temperature condition at 62° C. but the precipitates occurred to be unstable. However, the five humanized antibodies showed significantly lower variability of ANS reagent reactivity than chimeric antibodies, and no precipitates were produced. In particular, the humanized antibodies Protein ID 3019 and Protein ID 3058 had variability of ANS reagent reactivity of 114% and 133%, respectively, and thus were considered as most stable antibodies. The meaning of increased ANS reagent reactivity refers to the increased exposure of the hydrophobic amino acid placed inside the protein structure, which is responsible for the denaturation of the protein structure and the resulting protein aggregate, i.e., precipitate formation. The humanized antibody according to the present invention is considered to be stable antibody having the ANS reactivity variation of less than 200%. The ANS reactivity variation of less a change of less than 200% is considered to be very low, and over the value, a more significant change in protein structure is considered to be the observation of ANS reactivity. Accordingly, the humanized antibody according to the present invention has similar antigen binding and cell binding ability to chimeric antibody, and the increased physical stability of the antibody protein itself, such facts are a very excellent feature in the drugability for the therapeutic antibody.

2.5 CHO Cell Expression and Analysis of Recombinant Humanized Antibody

The five recombinant humanized antibodies selected in Example 2.3 were expressed in CHO cells used for expressing most therapeutic antibodies and analyzed. The light chain variable region DNA sequence and heavy chain variable region DNA sequence to construct the selected five recombinant humanized antibodies were performed by the codon optimization, synthesized, and ligated with the human IgG1 constant region gene by overlay PCR method. The product was cut with XhoI and EcoRI and ligated into the pcDNA3.4 vector (Life Technology). Table 11 shows the light chain and heavy chain combinations of humanized antibodies selected for CHO cell expression.

The DNA primer sequences used for PCR on the variable region and constant region gene are shown in Table 14 below.

TABLE 14

| Primer name | use | Target gene | sequences | SEQ ID NO |
|---|---|---|---|---|
| 8F01 | 1st frag forward | VH6, VH7, VH10, VH11 | ATTACTCGAGGCCACCATGAA | 64 |
| 8F02 | 1st frag reverse | VH6, VH10, VH11 | AGTTGAAGCGCTGCTCACAGTCA | 65 |
| 8F03 | 2nd frag forward | VH6, VH10, VH11 | GTGAGCAGCGCTTCAACTAAGGG | 66 |
| 3E04 | 2nd frag reverse | VH6, VH7, VH10, VH11 | AGTCGAATTCTCATTTCCCAGGAGAG | 67 |
| 8F04 | 1st frag reverse | VH7 | AGTTGAAGCAGAAGACACTGTCA | 68 |
| 8F05 | 2nd frag forward | VH7 | GTGTCTTCTGCTTCAACTAAGGG | 69 |

TABLE 14-continued

| Primer name | use | Target gene | sequences | SEQ ID NO |
|---|---|---|---|---|
| 3E01 | $1^{st}$ frag forward | Vk5, Vk7, Vk8 | ATTACTCGAGGCCACC<br>ATGAAGTGGG | 70 |
| 8F06 | $1^{st}$ frag reverse | Vk5, Vk7, Vk8 | AACAGTCCGCTTGATC<br>TCCAGCT | 71 |
| 3EL02(2) | $2^{nd}$ frag forward | Vk5, Vk7, Vk8 | GAGATCAAGCGGACTG<br>TTGCTGC | 72 |
| 3E08 | $2^{nd}$ frag reverse | Vk5, Vk7, Vk8 | ATTAGAATTCTCAGCA<br>CTCGCCGCGG | 73 |

The five (5) recombinant humanized antibodies were transiently transfected using the ExpiCHO (trademark) Expression System Kit (ThermoFisher, Cat. No. A29133), and the expressed antibodies were transfected with CD66c-positive A549 non-small lung cancer cell line and analyzed by flow cytometer, as shown in FIGS. 6*a* to 6*c*. All five recombinant humanized antibodies showed similar binding affinities to chimeric antibodies. The measured fluorescence value of the flow cytometer was divided by the antibody expression amount of the CHO culture medium to obtain the relative the binding affinity of antibody to the antibody expression amount, as shown in FIG. 6*d*. Therefore, it was confirmed that the recombinant humanized antibody was properly expressed in CHO cells. The binding affinity of the antibody to the cell surface was determined as 100%, and the relative change was shown in FIG. 6*d*.

<Example 3> CHO Cell Expression and Analysis of DNP002

DNP002, a humanized antibody against anti-CD66c was expressed and analyzed in CHO cells used to express most of the therapeutic. In order to test the difference in function according to the subtype of the DNP002 antibody, IgG1 type and IgG2 type antibodies were prepared.

After performing the codon optimization of DNA sequences of the light and heavy chain variable region for constructing humanized recombinant antibodies, they were synthesized and linked with constant region o human IgG1 or IgG2 by overlay PCR method, and XhoI and EcoRI gene fragment was cloned into pcDNA3.4 vector (Life Technology).

TABLE 15

| class-ification | Amino acid sequence | cDNA sequence |
|---|---|---|
| Constant region of IgG1 heavy chain | ASTKGPSVFPLAPSSK<br>STSGGTAALGCLVKD<br>YFPEPVTVSWNSGAL<br>TSGVHTFPAVLQSSGL<br>YSLSSVVTVPSSSLGT<br>QTYICNVNHKPSNTK<br>VDKKVEPKSCDKTHT<br>CPPCPAPELLGGPSVF<br>LFPPKPKDTLMISRTP<br>EVTCVVVDVSHEDPE<br>VKFNWYVDGVEVHN<br>AKTKPREEQYNSTYR<br>VVSVLTVLHQDWLN<br>GKEYKCKVSNKALPA<br>PIEKTISKAKGQPREP<br>QVYTLPPSRDELTKN<br>QVSLTCLVKGFYPSDI<br>AVEWESNGQPENNY<br>KTTPPVLDSDGSFFLY<br>SKLTVDKSRWQQGN<br>VFSCSVMHEALHNHY<br>TQKSLSLSPGK<br>(SEQ ID NO: 74) | GCTTCAACTAAGGGACCAAGCGTATTCCCACTTGCTCCAT<br>CTAGCAAGAGCACTAGCGGAGGAACAGCTGCTTTGGGGT<br>GTTTGGTAAAGGATTACTTTCCCGAACCTGTTACCGTGAG<br>CTGGAACAGCGGGGCTTTGACAAGTGGCGTTCATACATTT<br>CCTGCCGTTTTGCAAAGCAGCGGCTTGTATAGCTTGAGCT<br>CTGTTGTTACCGTTCCAAGCTCATCTCTGGGCACACAAAC<br>ATACATCTGCAACGTGAACCACAAGCCCTCAAACACCAA<br>GGTGGACAAGAAGGTGGAGCCAAAGTCTTGCGACAAGAC<br>CCACACCTGTCCACCTTGTCCAGCCCCTGAACTCCTGGGG<br>GGCCCTTCAGTTTTTCTCTTTCCTCCTAAACCTAAAGATAC<br>ACTCATGATCAGTCGGACCCCTGAAGTTACCTGTGTGGTG<br>GTCGATGTGTCTCATGAAGATCCTGAAGTCAAGTTTAACT<br>GGTATGTGGACGGCGTGGAGGTGCATAATGCCAAGACCA<br>AGCCTCGGGAGGAGCAATATAATTCTACCTATCGCGTCGT<br>CTCTGTCCTCACCGTCCTGCATCAGGACTGGCTGAATGGC<br>AAAGAGTATAAGTGCAAAGTCAGTAACAAAGCCCTCCCC<br>GCCCCCATAGAGAAAACCATTAGTAAAGCCAAAGGGCAG<br>CCCCGCGAGCCCCAGGTCTATACACTGCCCCCCAGTAGA<br>GACGAGCTGACAAAGAATCAGGTGTCTCTGACATGCCTG<br>GTGAAAGGCTTTTATCCCTCTGACATTGCCGTCGAGTGGG<br>AGTCTAATGGGCAGCCCGAGAATAATTATAAGACAACAC<br>CCCCCGTGCTGGACAGTGACGGCTCATTTTTCCTGTATTC<br>AAAACTGACAGTGGACAAAAGTCGGTGGCAGCAGGGGA<br>ATGTGTTTTCATGCAGTGTCATGCACGAGGCCCTCCACAA<br>TCACTATACCCAGAAATCTCTGAGTCTCTCTCCTGGGAAA<br>TGA (SEQ ID NO: 75) |
| Constant region of IgG2 heavy chain | ASTKGPSVFPLAPCSR<br>STSESTAALGCLVKD<br>YFPEPVTVSWNSGAL<br>TSGVHTFPAVLQSSGL<br>YSLSSVVTVPSSNFGT<br>QTYTCNVDHKPSNTK<br>VDKTVERKCCVECPP<br>CPAPPVAGPSVFLFPP<br>KPKDTLMISRTPEVTC | GCTTCCACCAAGGGCCCATCCGTGTTCCCTCTGGCCCCAT<br>GTTCTAGGTCTACATCTGAGAGCACCGCCGCCCTCGGCTG<br>TCTGGTGAAGGATTATTTCCCCGAGCCCGTGACCGTGTCT<br>TGGAACAGCGGAGCCCTGACTAGCGGAGTGCACACCTTC<br>CCAGCTGTGCTGCAGAGCTCCGGCCTGTACAGCCTCTCTT<br>CTGTGGTGACCGTGCCCTCTAGCAACTTCGGAACACAGA<br>CCTACACATGTAACGTGGATCACAAGCCTTCCAACACCA<br>AGGTGGATAAGACCGTGGAGAGAAAGTGCTGTGTGGAGT<br>GCCCTCCATGTCCTGCCCCACCTGTGGCTGGACCTTCTGT |

TABLE 15-continued

| classification | Amino acid sequence | cDNA sequence |
|---|---|---|
| | VVVDVSHEDPEVQFN WYVDGVEVHNAKTK PREEQFNSTFRVVSVL TVVHQDWLNGKEYK CKVSNKGLPAPIEKTI SKTKGQPREPQVYTL PPSREEMTKNQVSLT CLVKGFYPSDIAVEW ESNGQPENNYKTTPP MLDSDGSFFLYSKLT VDKSRWQQGNVFSCS VMHEALHNHYTQKS LSLSPGK (SEQ ID NO: 76) | GTTTCTGTTCCCTCCAAAGCCAAAGGATACCCTGATGATC AGCAGAACTCCTGAGGTGACCTGTGTGGTGGTGGACGTG AGCCACGAGGATCCTGAGGTGCAGTTTAACTGGTACGTG GATGGCGTGGAGGTGCATAACGCTAAGACAAAGCCTAGG GAGGAGCAGTTTAACAGCACCTTCAGAGTGGTGAGCGTG CTGACCGTGGTGCACCAGGATTGGCTGAACGGCAAGGAG TATAAGTGTAAGGTGTCTAACAAGGGCCTGCCAGCCCCT ATTGAGAAGACCATCAGTAAGACCAAGGGACAGCCTAGG GAGCCTCAGGTGTACACCCTGCCTCCTTCCAGAGAGGAG ATGACAAAGAACCAGGTGAGCCTGACCTGTCTGGTGAAG GGCTTCTACCCTAGCGATATCGCCGTGGAGTGGGAGAGC AACGGCCAGCCTGAGAACAACTACAAGACCACCCCACCT ATGCTGGACAGCGATGGCTCTTTCTTCCTGTACTCTAAGC TGACCGTGGACAAGAGCAGATGGCAGCAGGGCAACGTGT TTTCTTGTTCTGTGATGCACGAGGCCCTGCACAACCACTA CACCCAGAAGTCTCTGTCTCTGTCTCCAGGCAAGTGA (SEQ ID NO: 77) |
| Constant region of light chain | RTVAAPSVFIFPPSDE QLKSGTASVVCLLNN FYPREAKVQWKVDN ALQSGNSQESVTEQD SKDSTYSLSSTLTLSK ADYEKHKVYACEVT HQGLSSPVTKSFNRGE C (SEQ ID NO: 78) | CGGACTGTTGCTGCTCCATCTGTTTTTATATTTCCTCCCAG CGACGAGCAGCTGAAAAGCGGCACTGCCTCTGTGGTGTG TCTGCTGAATAATTTTTACCCCCGGGAAGCCAAAGTCCAG TGGAAGGTGGATAATGCCCTCCAGTCTGGGAACAGTCAG GAAAGTGTGACAGAACAGGATAGTAAGGACTCTACTTAT AGCCTCTCTTCTACACTGACTCTGTCAAAGGCCGACTATG AGAAGCATAAAGTGTATGCCTGCGAGGTGACACATCAGG GCCTGAGTTCACCCGTGACAAAATCTTTTAACCGCGGCGA GTGCTGA (SEQ ID NO: 79) |

To prepare afucosylated DNP002 humanized antibody, when the DNP002 IgG1 type antibody was expressed, 2F-PF (2F-Peracetyl-Fucose; Merck, Cat #: 344827) was added to the culture medium at 50 uM and cultured, and then purified using Mabselect sure Protein A column (GE Healthcare Lifescience, Cat #:11003494). The purified antibody was dialyzed with phosphate buffered saline, and the absorbance at 280 nm was divided by the absorbance coefficient of 1.4 and converted into a concentration unit of "mg/mL", and then, it was used for the subsequent experiment.

Afucosylation was evaluated by relatively comparing the reactivity of Biotinylated *Lens culinaris* agglutinin (Vector laboratories, Cat #:B-1045) having a binding property to fucose. Fucose-conjugated IgG1 DNP002 reacted with Biotinylated *Lens culinaris* agglutinin and were used for TMB color development by SA-HRP (Jackson immunoresearch, Cat #:016-030-084). However, afucosylated DNP002 had relatively little color development (Table 16).

TABLE 16

| Antibody concentration (ng/ml) | DNP002 humanized antibody | afucosylated DNP002 humanized antibody |
|---|---|---|
| 10000 | 1.452 | 0.229 |
| 3333 | 1.254 | 0.210 |
| 1111 | 0.993 | 0.164 |
| 370 | 0.283 | 0.115 |
| 123 | 0.116 | 0.076 |
| 41 | 0.080 | 0.083 |
| 14 | 0.095 | 0.059 |
| 5 | 0.094 | 0.070 |

<Example 4> Investigation of Reactivity of DNP002 Antibody to MDSC

The reactivity of DNP002 antibody against MDSC was evaluated by flow cytometric analysis.

Specifically, after preparing blood from stomach cancer patients, DNP002 with bound with APC and the antibodies (anti-HLA-DR-FITC, CD11b-PE, CD33-PE antibodies) against the labeled antigens of MDSC with different fluorescence together were added to 100 uL of whole blood and reacted at 4° C. for 20 minutes. The product was added with 5 ml of red blood cell (RBC) lysis buffer of 1×RBC Lysis Buffer (ThermoFisher, Cat #:00-4333-57), reacted at room temperature for 30 minutes, centrifuged to remove the decomposed RBC, washed again with PBS, and performed by flow cytometry. The staining intensity was measured as a log of fluorescence intensity and expressed in units of tens.

In the analysis of the results, after only monocytes and granulocyte regions except lymphocyte were designated according to the cell size in the dot plot, the groups with no or low HLA-DR expression were selected, and the groups being positive for CD11b and CD33 were selected from that groups and designated as MDSC. The positive rate of DNP002 in the designated MDSC group was confirmed (FIG. 7).

Specifically, from left to right direction in the upper graphs in FIG. 7, 1) gated only monocytes and granulocytes in FSC and SSC dot plots with excluding lymphocytes. (FSC: forward scatter, a variable indicating the size of cells to be analyzed, SSC: side scatter, a variable indicating the granularity of the cells to be analyzed and the degree of granule existing in the cells), 2) gated HLA-DR Low or (−) groups, and 3) MDSC being positive to CD11b and CD33 among the 1st and 2nd groups. DNP002 positive MDSCs are 90.9% (upper right site in the right dot plot of FIG. 7), and DNP002 negative MDSCs are 4.4% (upper left site in the right dot plot of FIG. 7). MDSC is divided into subtypes of a monocytic MDCS and a granulocytic MDSC. The granulocytic MDSC expresses CD66b, but the monocytic MDCS does not express CD66b, so whether or not CD66b is expressed can be usefully used for discriminating MDSC subtypes.

FIG. 7 is a result of proving the method of defining MDSC (excluding lymphocytes, HLA-DR low/(−), CD11b+, CD33+) and the reactivity of DNP002 (anti-CD66c) specific to MDSC. Because DNP002 binds to MDSC, DNP002 can be used as a method for specifying MDSC (FIG. 7), and DNP002 can cause ADCC effects to remove MDSC (FIG. 8). In the following test results, the MDSC bound with DNP002 was 90.9%.

FIG. 8 shows a phenomenon in which CD66b-positive granulocytic MDSCs were killed by DNP002 treatment and descried in their ratio. In FIG. 8, the upper dot plot (control group) represents a sample before treatment with DNP002, and the bottom dot plot (DNP002) is the result of decreased MDSC after treatment with DNP002. CD66b is a marker that can differentiate between monocytic MDSC and granulocytic MDSC. In the following test results, most of the MDSCs were CD66b-positive granulocytic MDSCs, and granulocytic MDSCs were effectively killed by DNP002.

As a result of analyzing the blood of 19 stomach cancer patients, the positive rate of DNP002 on MDSC in all PBMCs was 34.3~76.7%, and the average positive rate was 55.1%. Table 17 below is an analysis result of the reactivity of DNP002 antibody to MDSC with samples of 19 stomach cancer patients.

TABLE 17

| Blood # | $DNP002^{+}$MDSC of total PBMC (%) | |
|---|---|---|
| GC patient #1 | 49.8 | 55.1 |
| GC patient #2 | 50.5 | |
| GC patient #3 | 68.6 | |
| GC patient #4 | 61.8 | |
| GC patient #5 | 48.8 | |
| GC patient #6 | 70.5 | |
| GC patient #7 | 45.6 | |
| GC patient #8 | 36.0 | |
| GC patient #9 | 51.4 | |
| GC patient #10 | 34.3 | |
| GC patient #11 | 49.8 | |
| GC patient #12 | 53.5 | |
| GC patient #13 | 63.7 | |
| GC patient #14 | 72.0 | |
| GC patient #15 | 43.5 | |
| GC patient #16 | 67.4 | |
| GC patient #17 | 76.7 | |
| GC patient #18 | 42.5 | |
| GC patient #19 | 60.4 | |

<Example 5> Lysis Effect of DNP002 on MDSC 5.1. Lysis Effect of DNP002 on MDSC in Whole Blood In order to check the MDSC killing effect by DNP002, erythrocyte lysis buffer of 1×RBC Lysis Buffer (ThermoFisher, Cat #:00-4333-57) was added to the blood of 5 stomach cancer patients to dissolve red blood cells, and then the product was poured $1\times10^5$ per a well of 12-well plate. DNP002 antibody was added to each well at a concentration of 10 ug/mL and incubated in an incubator at 37° C. for one day. After incubation, the cells were washed with PBS, and reacted with antibodies (anti-HLA-DR, CD11b, CD33 antibodies) against the MDSC-labeled antigens with different fluorescence at 4° C. for 20 minutes. After washing with PBS, the flow cytometry was performed. The staining intensity was measured as a log of fluorescence intensity and expressed in units of tens.

As a result of the above experiment, FIG. 8 shows a representative result in which the DNP002 antibody effectively induces apoptosis of MDSC in the blood, and the MDSC ratio is significantly reduced compared to pre-treatment with the DNP002 antibody. FIG. 9 is a diagram illustrating the same test as in FIG. 8 for the blood samples of five (5) stomach cancer patients. The open bar means the ratio of MDSC before DNP002 treatment, and the closed bar means the relative ratio of MDSC after DNP002 treatment. After DNP002 treatment, it can be seen that the MDSC ratio has been significantly reduced in all 5 patient samples.

5.2. Lysis Effect of DNP002 on MDSC in PBMC

In order to more clearly clarify the MDSC-targeted killing ability of the DNP002 antibody, MDSC was only obtained with excluding mature neutrophils, and the MDSC killing effect of the DNP002 antibody was tested without the effect of neutrophils.

Specifically, only the PBMC layer containing MDSC was separated from the blood of two stomach cancer patients using Ficoll-Paque PLUS (Ge healthcare, Cat #:17-1440-02) solution. The density gradient separation of blood cells through the Ficoll solution effectively excludes mature neutrophils, so that MDSC killing effects can be analyzed more accurately. The prepared PBMC were dispensed at $1\times10^5$ per well into a 12 well plate, and DNP002 antibody was added to each well at a concentration of 10 μg/mL, followed by incubation at 37° C. for 48 hours. At this time, the MDSC killing ability was compared using Nivolumab (Bristol-Myers Squibb) of an antibody against PD-1, as a control. After culture, the cells were washed with PBS, and the increase or decrease of the MDSC group was analyzed through flow cytometry (FIG. 10).

As a result of the flow cytometry, the group treated with DNP002 showed an average of about 49% apoptosis compared to the group with no treatment of DNP002. On the other hand, Nivolumab used as a control showed only about 24% MDSC killing effect. The MDSC killing effect was the same in both MDSCs isolated from two patients. Therefore, this experiment confirms that the effect of killing MDSC by the DNP002 antibody is significant.

The lysis effect of MDSC by DNP002 was confirmed for whole blood (Example 5.1) and PBMC (peripheral blood mononuclear cells; Example 5.2), respectively. In whole blood and PBMC, NK cells of the patient who can induce ADCC are included, and can lyse CEACAM6-positive cells with ADCC via DNP002. However, in whole blood, neutrophils positive for the CEACAM6 target antigen and MDSC are mixed, and it is difficult to say that only MDSs are selectively lysed. In order to clarify the selective lysis of MDSC by DNP002, an additional experiment was performed on PBMCs in which neutrophils are removed by layer separation with centrifugation (Example 5.2). Accordingly, it was confirmed that the MDSC lysis by DNP002 was evident.

<Example 6> Lysis Effect of Different Antibody Isotypes on MDSC

In order to test the ability of the DNP002 antibody to kill the MDSC target, three types of DNP002 antibodies were prepared. The antibodies differ in the affinity to FcrRIII (CD16) expressed on NK cells depending on the isotypes of antibodies, and antibody-dependent cell-mediated cytotoxicity (ADCC) increases in proportional to the affinity. The IgG2 isotype had a very low affinity to FcrRIII and did not have ADCC efficacy, whereas the IgG1 isotype had high affinity for FcrRIII and had excellent ADCC efficacy. It has been reported that the ADCC efficacy of an antibody depends not only on the isotype but also on the sugar chain structure linked to the 297th asparagine of the antibody. In particular, when there is no fucose in the sugar chain, ADCC efficacy increases (Shitara K., et al, J Immunol Methods. 2005 Nov. 30; 306(1-2) IgG subclass-independent improvement of antibody-dependent cellular cytotoxicity by fucose removal from Asn297-linked oligosaccharides).

In vitro tests were performed to test the ability to kill MDSC targets depending on the isotype and the afucosylation of the DNP002 antibody. RBC lysis buffer of 1×RBC Lysis Buffer (ThermoFisher, Cat #:00-4333-57) was added to the blood of five stomach cancer patients to lyse RBC, and then the product was poured at $1\times10^5$ per well into a 12-well plate. Three kinds of antibodies such as DNP002 IgG1 type, DNP002 IgG2 type, and aflucosylated IgG1 type were added to each well at a concentration of 10 ug/mL and incubated in an incubator at 37° C. for one day. After incubation, the cells were washed with PBS, and reacted with antibodies (anti-HLA-DR, CD11b, CD33 antibodies) against the MDSC-labeled antigens with different fluorescence at 4° C. for 20 minutes. After washing with PBS, the flow cytometry was performed. The staining intensity was measured as a log of fluorescence intensity and expressed in units of tens.

It was observed that the MDSC killing effect was increased in the order of IgG2, IgG1, and afucosylated IgG1 type in all five stomach cancer patients as test subjects (FIGS. 11*a* and 11*b*). The difference in MDSC killing effect according to the isotype and the afucosylation degree (the fucose content is less than 10%) is considered by the difference in the affinity of the antibodies to FcrRIII, and the killing effect of MDSC can be understood as the ADCC effect by NK cells.

As shown in FIG. 11*a*, it is a representative result confirming the DNP002 formulation type capable of effectively removing MDSC. Compared to the upper part (control), a large portion of MDSC remained in DNP002 IgG2, but the MDSC ratio was significantly reduced in DNP002 IgG1. This test confirmed that the killing effect of MDSC by DNP002 IgG1 was significant high, but that by DNP002 IgG2 was not significant. Since the ADCC effect of the IgG2 isotype was absent or very low compared to the IgG1 isotype, the MDSC killing effect by DNP002 IgG1 was inferred by ADCC.

As shown in FIG. 11*b*, the same test as in FIG. 9 is tested and plotted in blood samples of 5 stomach cancer patients, and the horizontal axis of the graph represents each of the 5 stomach cancer patients (P #1, P #2, P #3, P #4, P #5). The MDSC killing effects were observed in the order of Control, IgG2, IgG1, and IgG1-afucosylated. The IgG2 isotype has no or insignificant MDSC killing effect, because it does not have ADCC function, but the MDSC killing effect is excellent in IgG1 having ADCC function and IgG1-afucosylated having enhanced ADCC function by defucosylation.

<Example 7> Cancer Cell Killing Effect by Combined Use of DNP002 and Natural Killer Cells In vitro tests were performed to test the combined effect of the DNP002 antibody and natural killer (NK) cells. After separating PBMC from three normal blood using Ficoll-Paque PLUS (Ge healthcare, Cat #:17-1440-02) solution, only CD56-positive natural killer cells were isolated by using CD56 micro bead (Miltenyi Biotec, Cat #:130-050-401). In FIGS. 12*a* and 12*b*, the horizontal axis represents three blood donors, which are the origins of the natural killer cells, respectively.

The stomach cancer cell line A549 and the pancreatic cancer cell line AsPC-1 which were positive for CEACAM6 of a target antigen of DNP002, were dispensed in a 96-well plate at $1\times10^4$ per well, dispensed with the previously isolated natural killer cells at $2\times10^5$ per well, treated with DNP002 antibody at 10 μg/mL, and then was incubated at 37° C. for 6 hours.

As a result of measuring cell viability using the EZ-cytox enhanced cell viability kit (Daeil Lab), it was confirmed that the apoptosis effect by the combination of DNP002 antibody and natural killer cells in both cancer cell lines increased compared to single treatment (FIG. 12*a* and FIG. 12*b*).

This indicates that the cancer cell killing ability of DNP002 was significantly amplified by the combination with natural killing cells. Through this, it is indicated that combination treatment with NK cells or NK cell therapeutic agents can be excellent for effective removal of CEACAM6-positive MDSCs as well as CEACAM6-positive cancer cells.

The selective lysis of MDSC by DNP002 in Example 5.2 and the combined effect with NK cells or NK cell therapeutic agents in Example 7 confirm that both CEACAM6-positive cancer cells and CEACAM6-positive MDSCs can be eliminated as the targets. Although Example 5.2 and Example 7 showed ADCC for different target cells as MDSC and cancer cells, respectively, in the case of cancer patients in which two types of cells are actually increased together, DNP002 can simultaneously remove both types of targets, and can be used in combination with NK cell therapeutic agent, in order to double the efficacy of simultaneous removal of cancer cells and MDSCs targets.

<Example 8> Detection of MDSC in Cancer Microenvironment of CEACAM6-Negative Patient Since CEACAM6 antigen is expressed not only in cancer cells but also in MDSC, it is possible to detect not only cancer cells but also MDSC using the DNP002 antibody. To test this, MDSC but not cancer cells were detected in cancer patient tissues with positive or negative CEACAM6 antigens, by immunohistochemistry (Immunohistochemistry).

Immunohistochemical staining was performed in the following manner. The tissue was deparaffinized in xylene for 10 minutes at 3 times, 100% alcohol for 10 minutes at 2 times, 80% alcohol for 5 minutes, and 70% alcohol for 3 minutes, and then washed with 3rd distilled water. Then, Peroxidase blocking was carried out by immersing in 0.03% $H_2O_2$ for 10 minutes at room temperature, and washed with 3rd distilled water Immediately, the slide was put in 1× citrate buffer (Citrate buffer, pH 6.0), heated in a boiling tap water for 20 minutes, cool it slowly, wash it with 3rd distilled water, and washed it once again with 1×PBS. The monoclonal antibody of DNP002, 8F5 antibody was reacted on the region of tissue at room temperature for 90±5 minutes at 150 ul (10 ug/ml) per slide. After the reaction, the slide was washed with 1×PBS for 5 minutes each at 4 times. The secondary antibody was reacted with 100 ul per slide for 20 minutes at room temperature, and after the reaction, washed 4 times with 1×PBST for 5 minutes each. DAB Chromogen developed 100 ul per slide at room temperature for 3 minutes and the slide was washed with tap water for 10 minutes. Mayer's Hematoxylin was counter-stained at room temperature for 3 minutes at 100 ul per slide and washed under running tap water for 10 minutes. After dehydration, the slide was mounted.

As results of CEACAM6 immunostaining on lung adenocarcinoma which was CEACAM6 positive in cancer cells, and lung squamous cell carcinoma, urinary bladder cancer, and melanoma malignancy which were CEACAM6 negative in cancer cells themselves, it was confirmed that there was CEACAM6-positive MDSC in the non-tumor site of the cancer tissue (FIG. 13). This indicates that, regardless of the expression of CEACAM6 antigen in cancer tissues or cancer cells themselves, MDSCs infiltrated around cancer tissues can be used as a target for diagnosis and treatment.

Regardless of the degree of CEACAM6 on the cell surface of cancer cells, MDSC tended to increase in cancer patients, which could detect and confirm MDSCs infiltrating the tumor microenvironment as in Example 8. This indicates that MDSC can be used as a target for diagnosis and treatment purposes regardless of the positivity of CEACAM6 on cancer cells, when considered together with the result of Example 5.2 showing the selective lysis of MDSC. The presence or absence of CEACAM6 expression on the cell surface of cancer cells may differ depending on the cancer type, but regardless of this, MDSC is increased in most cancer types. Accordingly, it indicates that DNP002 can be used for diagnostic and therapeutic purposes in a most cancers by targeting MDSC.

The invention claimed is:

1. An immune-enhancing agent comprising an antibody or an antigen-binding fragment thereof specifically binding to CD66c (Cluster of Differentiation 66c) which is expressed in a myeloid-derived suppressor cell (MDSC), wherein the antibody or antigen-binding fragment thereof comprises the following complementarity determining regions (CDRs):

CDR-H1 comprising an amino acid sequence of SEQ ID NO: 1 or SEQ ID NO: 9,

CDR-H2 comprising an amino acid sequence of SEQ ID NO: 2 or SEQ ID NO: 10,

CDR-H3 comprising an amino acid sequence of SEQ ID NO: 3,

CDR-L1 comprising an amino acid sequence of SEQ ID NO: 4, SEQ ID NO: 11 or SEQ ID NO: 12, CDR-L2 comprising an amino acid sequence of SEQ ID NO: 5 and CDR-L3 comprising an amino acid sequence of SEQ ID NO: 6 or SEQ ID NO: 13, on the proviso that the antibody comprising CDRs consisting of amino acid sequences of SEQ ID NOs: 1, 2, 3, 4, 5, and 6 is not included.

2. The immune-enhancing agent of claim 1, wherein the immune-enhancing agent removes or reduces an immunosuppressive activity of MDSC by regulating activity, production or cell death of MDSC or inducing cell death of MDSC.

3. The immune-enhancing agent of claim 1, wherein the immune-enhancing agent regulates an immunosuppressive activity of MDSC on an activity of T cell, NK cell, or regulatory T cell.

4. The immune-enhancing agent of claim 1, wherein the antibody comprises IgG1, IgG2, IgG3 or IgG4 Fc domain.

5. The immune-enhancing agent of claim 1, wherein the antibody is afucosylated antibody.

6. The immune-enhancing agent of claim 1, wherein the heavy chain variable region of the antibody comprises at least one selected from the group consisting of framework sequence (V-FR1) including the amino acid sequence of SEQ ID NOs: 22, 23, 24, 25, 26 or 27, framework sequence (V-FR2) including the amino acid sequence of SEQ ID NOs: 32, 33, 34, 35, 36 or 37, framework sequence (V-FR3) including the amino acid sequence of SEQ ID NOs: 42, 43, 44, 45, 46 or 47, and framework sequence (V-FR4) including the amino acid sequence of SEQ ID NOs: 52, 53, 54, 55, 56 or 57, or wherein the light chain variable region of the antibody comprises at least one selected from the group consisting of framework sequence (L-FR1) including the amino acid sequence of SEQ ID NOs: 28, 29, 30 or 31, framework sequence (L-FR2) including the amino acid sequence of SEQ ID NOs: 38, 39, 40 or 41, framework sequence (L-FR3) including the amino acid sequence of SEQ ID NOs: 48, 49, 50, or 51, and framework sequence (L-FR1) including the amino acid sequence of SEQ ID NOs: 58, 59, 60 or 61.

7. The immune-enhancing agent of claim 1, wherein the antibody comprises a heavy chain variable region including the amino acid sequence of SEQ ID NOs: 7, 14, 15, 16, 17 or 18, and a light chain variable region including the amino acid sequence of SEQ ID NOs: 8, 19, 20, or 21.

8. The immune-enhancing agent of claim 1, wherein the antibody has the fluorescence variability against the ANS reagent which is less than 200% at 62° C.

9. The immune-enhancing agent of claim 1, wherein the antigen-binding fragment is scFv, (scFv)2, Fab, Fab' or $F(ab')_2$ of anti-CD66c antibody.

10. A method for prevention or treatment of a MDSC-related disease, comprising administering the immune-enhancing agent according to claim 1 to a subject in need of.

11. The method of claim 10, wherein the MDSC-related diseases represent HLA-DR Low/(−), CD11b+, and CD33+ phenotypes except for lymphocytes, and the number of CD66c-positive MDSCs is increased compared to that of normal cells.

12. The method of claim 10, regulating a suppressive activity of MDSC on activity of T cell, natural killer cell (NK cell), or regulatory T cell.

13. The method of claim 10, wherein the MDSC-related diseases are cancer or inflammatory diseases.

14. The method of claim 10, wherein the MDSC-related diseases are *Trypanosoma cruzi, Listeria monocytogenes, Leishmania major*, helminths, *Candida albicans*, or *Porphyromonas gingivalis* infection, toxoplasmosis, or polymicrobic sepsis.

15. The method of claim 10, wherein the MDSC-related diseases are stomach cancer, breast cancer, lung cancer, colon cancer, liver cancer, gallbladder cancer, kidney cancer, pancreatic cancer, thyroid cancer, prostate cancer, ovarian cancer, cervical cancer, bladder cancer, acute myelogenous leukemia, acute lymphoblastic leukemia, acute monocytic leukemia, or Hodgkin's lymphoma, or non-Hodgkin's lymphoma.

16. The method of claim 15, inhibiting growth of cancer cells or induction of cancer metastasis.

17. The method of claim 10, wherein the antibody is an IgG1 type antibody that recognizes CD66c and CD66b expressed in MDSC.

18. The method of claim 10, wherein the immune-enhancing agent is administered in combination of a NK cell or NK cell-derived cell therapy agent.

19. A method for diagnosis of MDSC-related diseases, comprising detecting Cluster of Differentiation 66c (CD66c) expressed in a myeloid-derived suppressor cell (MDSC), with an antibody or an antigen-binding fragment thereof specifically binding to Cluster of Differentiation 66c (CD66c) which is expressed in a myeloid-derived suppressor cell (MDSC), wherein the antibody or antigen-binding fragment thereof comprises the following complementarity determining regions (CDRs):

CDR-H1 comprising an amino acid sequence of SEQ ID NO: 1 or SEQ ID NO: 9,

CDR-H2 comprising an amino acid sequence of SEQ ID NO: 2 or SEQ ID NO: 10,

CDR-H3 comprising an amino acid sequence of SEQ ID NO: 3,

CDR-L1 comprising an amino acid sequence of SEQ ID NO: 4, SEQ ID NO: 11 or SEQ ID NO: 12, CDR-L2 comprising an amino acid sequence of SEQ ID NO: 5 and CDR-L3 comprising an amino acid sequence of SEQ ID NO: 6 or SEQ ID NO: 13, on the proviso that the antibody comprising CDRs consisting of amino acid sequences of SEQ ID NOs: 1, 2, 3, 4, 5, and 6 is not included.

20. The method of claim 19, wherein a diagnostic sample is a biological sample of a subject.

21. The method of claim 19, wherein the MDSC-related diseases represent HLA-DR Low/(−), CD11b+, and CD33+ phenotypes except for lymphocytes, and the number of CD66c-positive MDSCs is increased compared to that of normal cells.

22. The method of claim 19, wherein the MDSC-related diseases are stomach cancer, breast cancer, lung cancer, colon cancer, liver cancer, gallbladder cancer, kidney cancer, pancreatic cancer, thyroid cancer, prostate cancer, ovarian cancer, cervical cancer, bladder cancer, acute myelogenous leukemia, acute lymphoblastic leukemia, acute monocytic leukemia, or Hodgkin's lymphoma, or non-Hodgkin's lymphoma.

* * * * *

```
                         SEQUENCE LISTING


<160> NUMBER OF SEQ ID NOS: 79

<210> SEQ ID NO 1
<211> LENGTH: 12
<212> TYPE: PRT
<213> ORGANISM: Artificial Sequence
<220> FEATURE:
<223> OTHER INFORMATION: Synthetic_CDR-H1 of mouse or chimeric
      anti-CD66c antibody

<400> SEQUENCE: 1

Ala Ser Gly Tyr Ser Phe Thr Asp Tyr Thr Met Asn
1               5                   10


<210> SEQ ID NO 2
<211> LENGTH: 17
<212> TYPE: PRT
<213> ORGANISM: Artificial Sequence
<220> FEATURE:
<223> OTHER INFORMATION: Synthetic_CDR-H2 of mouse or chimeric
      anti-CD66c antibody

<400> SEQUENCE: 2

Leu Ile Asn Pro Phe His Gly Gly Thr Val Ser Asn Gln Arg Phe Lys
1               5                   10                  15

Val


<210> SEQ ID NO 3
<211> LENGTH: 14
<212> TYPE: PRT
<213> ORGANISM: Artificial Sequence
<220> FEATURE:
<223> OTHER INFORMATION: Synthetic_CDR-H3 of mouse or chimeric
      anti-CD66c antibody

<400> SEQUENCE: 3

Val Arg Gly Asp Pro Val Arg His Tyr Tyr Ala Leu Ala Tyr
1               5                   10


<210> SEQ ID NO 4
<211> LENGTH: 11
<212> TYPE: PRT
<213> ORGANISM: Artificial Sequence
<220> FEATURE:
<223> OTHER INFORMATION: Synthetic_CDR-L1 of mouse or chimeric
      anti-CD66c antibody

<400> SEQUENCE: 4

Gly Ala Ser Glu Asn Val Tyr Gly Thr Leu Asn
1               5                   10


<210> SEQ ID NO 5
<211> LENGTH: 7
<212> TYPE: PRT
```

-continued

```
<213> ORGANISM: Artificial Sequence
<220> FEATURE:
<223> OTHER INFORMATION: Synthetic_CDR-L2 of mouse or chimeric
      anti-CD66c antibody

<400> SEQUENCE: 5

Gly Ala Thr Asn Leu Ala Asp
1               5


<210> SEQ ID NO 6
<211> LENGTH: 15
<212> TYPE: PRT
<213> ORGANISM: Artificial Sequence
<220> FEATURE:
<223> OTHER INFORMATION: Synthetic_CDR-L3 of mouse or chimeric
      anti-CD66c antibody

<400> SEQUENCE: 6

Val Ala Thr Tyr Tyr Cys Gln Asn Val Leu Ser Ala Pro Tyr Thr
1               5                   10                  15


<210> SEQ ID NO 7
<211> LENGTH: 121
<212> TYPE: PRT
<213> ORGANISM: Artificial Sequence
<220> FEATURE:
<223> OTHER INFORMATION: Synthetic_Heavy chain variable region of mouse
      or chimeric anti-CD66c antibody

<400> SEQUENCE: 7

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ser His Gly Lys Asn Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Ser Asn Thr Ala Tyr
65                  70                  75                  80

Met Glu Leu Leu Ser Leu Thr Ser Asp Asp Ser Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Ser Val Thr Val Ser Ser
        115                 120


<210> SEQ ID NO 8
<211> LENGTH: 107
<212> TYPE: PRT
<213> ORGANISM: Artificial Sequence
<220> FEATURE:
<223> OTHER INFORMATION: Synthetic_Light chain variable region of mouse
      or chimeric anti-CD66c antibody

<400> SEQUENCE: 8

Asp Ile Gln Met Thr Gln Ser Pro Ala Ser Leu Ser Ala Ser Val Gly
1               5                   10                  15

Glu Thr Val Thr Ile Thr Cys Gly Ala Ser Glu Asn Val Tyr Gly Thr
            20                  25                  30

Leu Asn Trp Tyr Gln Arg Lys Gln Gly Lys Ser Pro Gln Leu Leu Ile
        35                  40                  45
```

-continued

Tyr Gly Ala Thr Asn Leu Ala Asp Gly Met Ser Ser Arg Phe Ser Gly
    50                  55                  60

Ser Gly Ser Gly Arg Gln Tyr Ser Leu Lys Ile Ser Ser Leu His Pro
65                  70                  75                  80

Asp Asp Val Ala Thr Tyr Tyr Cys Gln Asn Val Leu Ser Ala Pro Tyr
                85                  90                  95

Thr Phe Gly Gly Gly Thr Lys Leu Glu Ile Ile
            100                 105

<210> SEQ ID NO 9
<211> LENGTH: 12
<212> TYPE: PRT
<213> ORGANISM: Artificial Sequence
<220> FEATURE:
<223> OTHER INFORMATION: Synthetic_CDR-H1 of humanized anti-CD66c antibody

<400> SEQUENCE: 9

Ala Ser Gly Tyr Ser Phe Thr Asp Tyr Thr Met His
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic_CDR-H2 of humanized anti-CD66c antibody

<400> SEQUENCE: 10

Leu Ile Asn Pro Phe Gly Gly Ser Thr Ser Tyr Ala Gln Lys Phe Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: Synthetic_CDR-L1 of humanized anti-CD66c antibody

<400> SEQUENCE: 11

Gly Ala Ser Glu Asn Val Tyr Gly Thr Leu Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic_CDR-L1 of humanized anti-CD66c antibody

<400> SEQUENCE: 12

Arg Ala Ser Glu Asn Val Tyr Gly Thr Leu Asn
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic_CDR-L3 of humanized anti-CD66c antibody

<400> SEQUENCE: 13

```
Phe Ala Thr Tyr Tyr Cys Gln Asn Val Leu Ser Ala Pro Tyr Thr
1               5                   10                  15
```

<210> SEQ ID NO 14
<211> LENGTH: 128
<212> TYPE: PRT
<213> ORGANISM: Artificial Sequence
<220> FEATURE:
<223> OTHER INFORMATION: Synthetic_Heavy chain variable region of humanized anti-CD66c antibody (8F5-human-VH5)

<400> SEQUENCE: 14

```
Phe His Met Ala Asn Val His Gln Val Gln Leu Val Gln Ser Gly Ala
1               5                   10                  15

Glu Val Lys Lys Pro Gly Ala Ser Val Lys Ile Ser Cys Lys Ala Ser
            20                  25                  30

Gly Tyr Ser Phe Thr Asp Tyr Thr Met Asn Trp Val Arg Gln Ala His
        35                  40                  45

Gly Gln Asn Leu Glu Trp Ile Gly Leu Ile Asn Pro Phe His Gly Gly
    50                  55                  60

Thr Val Ser Asn Gln Arg Phe Lys Val Lys Ala Thr Leu Thr Val Asp
65                  70                  75                  80

Val Ser Thr Asn Thr Ala Tyr Met Glu Leu Ser Arg Leu Arg Ser Asp
                85                  90                  95

Asp Thr Ala Val Tyr Tyr Cys Val Arg Gly Asp Pro Val Arg His Tyr
            100                 105                 110

Tyr Ala Leu Ala Tyr Trp Gly Gln Gly Thr Leu Val Thr Val Ser Ser
        115                 120                 125
```

<210> SEQ ID NO 15
<211> LENGTH: 121
<212> TYPE: PRT
<213> ORGANISM: Artificial Sequence
<220> FEATURE:
<223> OTHER INFORMATION: Synthetic_Heavy chain variable region of humanized anti-CD66c antibody (8F5-human-VH6)

<400> SEQUENCE: 15

```
Gln Val Gln Leu Val Gln Ser Gly Ala Glu Val Lys Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Lys Gln Ala Pro Gly Gln Asn Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120
```

<210> SEQ ID NO 16
<211> LENGTH: 121
<212> TYPE: PRT

<213> ORGANISM: Artificial Sequence
<220> FEATURE:
<223> OTHER INFORMATION: Synthetic_Heavy chain variable region of humanized anti-CD66c antibody (8F5-human-VH7)

<400> SEQUENCE: 16

```
Gln Val Gln Leu Val Gln Ser Gly Ala Glu Val Lys Lys Pro Gly Ala
1               5                   10                  15

Ser Met Lys Ile Ser Cys Lys Ala Ser Gly Tyr Ser Phe Thr Asp Tyr
            20                  25                  30

Thr Met Asn Trp Val Arg Gln Ala Pro Gly Gln Gly Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Leu Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120
```

<210> SEQ ID NO 17
<211> LENGTH: 121
<212> TYPE: PRT
<213> ORGANISM: Artificial Sequence
<220> FEATURE:
<223> OTHER INFORMATION: Synthetic_Heavy chain variable region of humanized anti-CD66c antibody (8F5-human-VH10)

<400> SEQUENCE: 17

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Thr Met Asn Trp Val Lys Gln Ala Pro Gly Gln Asn Leu Glu Trp Ile
        35                  40                  45

Gly Leu Ile Asn Pro Phe His Gly Gly Thr Val Ser Asn Gln Arg Phe
    50                  55                  60

Lys Val Lys Ala Thr Met Thr Val Asp Val Ser Thr Asn Thr Ala Tyr
65                  70                  75                  80

Met Glu Leu Ser Arg Leu Arg Ser Asp Asp Thr Ala Val Tyr Tyr Cys
                85                  90                  95

Val Arg Gly Asp Pro Val Arg His Tyr Tyr Ala Leu Ala Tyr Trp Gly
            100                 105                 110

Gln Gly Thr Leu Val Thr Val Ser Ser
        115                 120
```

<210> SEQ ID NO 18
<211> LENGTH: 121
<212> TYPE: PRT
<213> ORGANISM: Artificial Sequence
<220> FEATURE:
<223> OTHER INFORMATION: Synthetic_Heavy chain variable region of humanized anti-CD66c antibody (8F5-human-VH11)

<400> SEQUENCE: 18

```
Gln Val Gln Leu Val Gln Ser Gly Ala Glu Val Lys Lys Pro Gly Ala
1               5                   10                  15
```

Ser Val Lys Ile Ser Cys Lys Ala Ser Gly Tyr Ser Phe Thr Asp Tyr
20 25 30

Thr Met His Trp Val Lys Gln Ala Pro Gly Gln Asn Leu Glu Trp Ile
35 40 45

Gly Leu Ile Asn Pro Phe Gly Gly Ser Thr Ser Tyr Ala Gln Lys Phe
50 55 60

Lys Gly Arg Val Thr Met Thr Arg Asp Thr Ser Thr Asn Thr Ala Tyr
65 70 75 80

Met Glu Leu Ser Arg Leu Arg Ser Asp Asp Thr Ala Val Tyr Tyr Cys
85 90 95

Val Arg Gly Asp Pro Val Arg His Tyr Tyr Ala Leu Ala Tyr Trp Gly
100 105 110

Gln Gly Thr Leu Val Thr Val Ser Ser
115 120

<210> SEQ ID NO 19
<211> LENGTH: 107
<212> TYPE: PRT
<213> ORGANISM: Artificial Sequence
<220> FEATURE:
<223> OTHER INFORMATION: Synthetic_Light chain variable region of humanized anti-CD66c antibody (8F5-human-VK5)

<400> SEQUENCE: 19

Asp Ile Gln Met Thr Gln Ser Pro Ser Thr Leu Ser Ala Ser Val Gly
1 5 10 15

Asp Arg Val Thr Ile Thr Cys Gly Ala Ser Glu Asn Val Tyr Gly Thr
20 25 30

Leu Ala Trp Tyr Gln Arg Lys Pro Gly Lys Ala Pro Lys Leu Leu Ile
35 40 45

Tyr Gly Ala Thr Asn Leu Ala Asp Gly Val Pro Ser Arg Phe Ser Gly
50 55 60

Ser Gly Ser Gly Arg Glu Tyr Thr Leu Thr Ile Ser Ser Leu Gln Pro
65 70 75 80

Asp Asp Phe Ala Thr Tyr Tyr Cys Gln Asn Val Leu Ser Ala Pro Tyr
85 90 95

Thr Phe Gly Gly Gly Thr Lys Leu Glu Ile Lys
100 105

<210> SEQ ID NO 20
<211> LENGTH: 107
<212> TYPE: PRT
<213> ORGANISM: Artificial Sequence
<220> FEATURE:
<223> OTHER INFORMATION: Synthetic_Light chain variable region of humanized anti-CD66c antibody (8F5-human-VK7)

<400> SEQUENCE: 20

Asp Ile Gln Met Thr Gln Ser Pro Ser Thr Leu Ser Ala Ser Val Gly
1 5 10 15

Asp Arg Val Thr Ile Thr Cys Gly Ala Ser Glu Asn Val Tyr Gly Thr
20 25 30

Leu Asn Trp Tyr Gln Arg Lys Pro Gly Lys Ala Pro Lys Leu Leu Ile
35 40 45

Tyr Gly Ala Thr Asn Leu Ala Asp Gly Val Pro Ser Arg Phe Ser Gly
50 55 60

Ser Gly Ser Gly Thr Glu Tyr Thr Leu Thr Ile Ser Ser Leu Gln Pro
65 70 75 80

```
Asp Asp Phe Ala Thr Tyr Tyr Cys Gln Asn Val Leu Ser Ala Pro Tyr
                85                  90                  95

Thr Phe Gly Gly Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic_Light chain variable region of humanized anti-CD66c antibody (8F5-human-VK8)

<400> SEQUENCE: 21

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Asn Val Tyr Gly Thr
            20                  25                  30

Leu Asn Trp Tyr Gln Arg Lys Pro Gly Lys Ala Pro Lys Leu Leu Ile
        35                  40                  45

Tyr Gly Ala Thr Asn Leu Ala Asp Gly Met Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Asp Asp Phe Ala Thr Tyr Tyr Cys Gln Asn Val Leu Ser Ala Pro Tyr
                85                  90                  95

Thr Phe Gly Gly Gly Thr Lys Leu Glu Ile Lys
            100                 105
```

<210> SEQ ID NO 22
<211> LENGTH: 23
<212> TYPE: PRT
<213> ORGANISM: Artificial Sequence
<220> FEATURE:
<223> OTHER INFORMATION: Synthetic_Framework1 in Heavy chain variable region of chimeric anti-CD66c antibody

<400> SEQUENCE: 22

```
Glu Val Gln Leu Gln Gln Ser Gly Pro Glu Leu Val Lys Pro Gly Ala
1               5                   10                  15

Ser Met Lys Ile Ser Cys Lys
            20
```

<210> SEQ ID NO 23
<211> LENGTH: 23
<212> TYPE: PRT
<213> ORGANISM: Artificial Sequence
<220> FEATURE:
<223> OTHER INFORMATION: Synthetic_Framework1 in Heavy chain variable region of humanized anti-CD66c antibody (8F5-human-VH5)

<400> SEQUENCE: 23

```
Gln Val Gln Leu Val Gln Ser Gly Ala Glu Val Lys Lys Pro Gly Ala
1               5                   10                  15

Ser Val Lys Ile Ser Cys Lys
            20
```

<210> SEQ ID NO 24
<211> LENGTH: 23
<212> TYPE: PRT
<213> ORGANISM: Artificial Sequence
<220> FEATURE:

<223> OTHER INFORMATION: Synthetic_Framework1 in Heavy chain variable
      region of humanized anti-CD66c antibody (8F5-human-VH6)

<400> SEQUENCE: 24

Gln Val Gln Leu Val Gln Ser Gly Ala Glu Val Lys Lys Pro Gly Ala
1               5                   10                  15

Ser Met Lys Ile Ser Cys Lys
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic_Framework1 in Heavy chain variable
      region of humanized anti-CD66c antibody (8F5-human-VH7)

<400> SEQUENCE: 25

Gln Val Gln Leu Val Gln Ser Gly Ala Glu Val Lys Lys Pro Gly Ala
1               5                   10                  15

Ser Met Lys Ile Ser Cys Lys
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic_Framework1 in Heavy chain variable
      region of humanized anti-CD66c antibody (8F5-human-VH10)

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys
            20

<210> SEQ ID NO 27
<211> LENGTH: 23
<212> TYPE: PRT
<213> ORGANISM: Artificial Sequence
<220> FEATURE:
<223> OTHER INFORMATION: Synthetic_Framework1 in Heavy chain variable
      region of humanized anti-CD66c antibody (8F5-human-VH11)

<400> SEQUENCE: 27

Gln Val Gln Leu Val Gln Ser Gly Ala Glu Val Lys Lys Pro Gly Ala
1               5                   10                  15

Ser Val Lys Ile Ser Cys Lys
            20

<210> SEQ ID NO 28
<211> LENGTH: 23
<212> TYPE: PRT
<213> ORGANISM: Artificial Sequence
<220> FEATURE:
<223> OTHER INFORMATION: Synthetic_Framework1 in Light chain variable
      region of chimeric anti-CD66c antibody

<400> SEQUENCE: 28

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 29
<211> LENGTH: 23
<212> TYPE: PRT
<213> ORGANISM: Artificial Sequence
<220> FEATURE:
<223> OTHER INFORMATION: Synthetic_Framework1 in Light chain variable
region of humanized anti-CD66c antibody (8F5-human-VK5)

<400> SEQUENCE: 29

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 30
<211> LENGTH: 23
<212> TYPE: PRT
<213> ORGANISM: Artificial Sequence
<220> FEATURE:
<223> OTHER INFORMATION: Synthetic_Framework1 in Light chain variable
region of humanized anti-CD66c antibody (8F5-human-VK7)

<400> SEQUENCE: 30

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 31
<211> LENGTH: 23
<212> TYPE: PRT
<213> ORGANISM: Artificial Sequence
<220> FEATURE:
<223> OTHER INFORMATION: Synthetic_Framework1 in Light chain variable
region of humanized anti-CD66c antibody (8F5-human-VK8)

<400> SEQUENCE: 31

```
Asp Ile Gln Met Thr Gln Ser Pro Ser Thr Leu Ser Ala Ser Val Gly
1               5                   10                  15

Asp Arg Val Thr Ile Thr Cys
            20
```

<210> SEQ ID NO 32
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of chimeric anti-CD66c antibody

<400> SEQUENCE: 32

```
Trp Val Lys Gln Ser His Gly Lys Asn Leu Glu Trp Ile Gly
1               5                   10
```

<210> SEQ ID NO 33
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of humanized anti-CD66c antibody (8F5-human-VH5)

<400> SEQUENCE: 33

```
Trp Val Arg Gln Ala His Gly Gln Asn Leu Glu Trp Ile Gly
1               5                   10
```

<210> SEQ ID NO 34
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of humanized anti-CD66c antibody (8F5-human-VH6)

<400> SEQUENCE: 34

Trp Val Lys Gln Ala Pro Gly Gln Asn Leu Glu Trp Ile Gly
1 5 10

<210> SEQ ID NO 35
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of humanized anti-CD66c antibody (8F5-human-VH7)

<400> SEQUENCE: 35

Trp Val Arg Gln Ala Pro Gly Gln Gly Leu Glu Trp Ile Gly
1 5 10

<210> SEQ ID NO 36
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of humanized anti-CD66c antibody (8F5-human-VH10)

<400> SEQUENCE: 36

Trp Val Lys Gln Ala Pro Gly Gln Asn Leu Glu Trp Ile Gly
1 5 10

<210> SEQ ID NO 37
<211> LENGTH: 14
<212> TYPE: PRT
<213> ORGANISM: Artificial Sequence
<220> FEATURE:
<223> OTHER INFORMATION: Synthetic_Framework2 in Heavy chain variable
region of humanized anti-CD66c antibody (8F5-human-VH11)

<400> SEQUENCE: 37

Trp Val Lys Gln Ala Pro Gly Gln Asn Leu Glu Trp Ile Gly
1 5 10

<210> SEQ ID NO 38
<211> LENGTH: 15
<212> TYPE: PRT
<213> ORGANISM: Artificial Sequence
<220> FEATURE:
<223> OTHER INFORMATION: Synthetic_Framework2 in Light chain variable
region of chimeric anti-CD66c antibody

<400> SEQUENCE: 38

Trp Tyr Gln Arg Lys Gln Gly Lys Ser Pro Gln Leu Leu Ile Tyr
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic_Framework2 in Light chain variable
region of humanized anti-CD66c antibody (8F5-human-VK5)

<400> SEQUENCE: 39

Trp Tyr Gln Arg Lys Pro Gly Lys Ala Pro Lys Leu Leu Ile Tyr
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic_Framework2 in Light chain variable region of humanized anti-CD66c antibody (8F5-human-VK6)

<400> SEQUENCE: 40

Trp Tyr Gln Arg Lys Pro Gly Lys Ala Pro Lys Leu Leu Ile Tyr
1 5 10 15

<210> SEQ ID NO 41
<211> LENGTH: 15
<212> TYPE: PRT
<213> ORGANISM: Artificial Sequence
<220> FEATURE:
<223> OTHER INFORMATION: Synthetic_Framework2 in Light chain variable region of humanized anti-CD66c antibody (8F5-human-VK8)

<400> SEQUENCE: 41

Trp Tyr Gln Arg Lys Pro Gly Lys Ala Pro Lys Leu Leu Ile Tyr
1 5 10 15

<210> SEQ ID NO 42
<211> LENGTH: 38
<212> TYPE: PRT
<213> ORGANISM: Artificial Sequence
<220> FEATURE:
<223> OTHER INFORMATION: Synthetic_Framework3 in Heavy chain variable region of chimeric anti-CD66c antibody

<400> SEQUENCE: 42

Asn Gln Arg Phe Lys Val Lys Ala Thr Leu Thr Val Asp Val Ser Ser
1 5 10 15

Asn Thr Ala Tyr Met Glu Leu Leu Ser Leu Thr Ser Asp Asp Ser Ala
20 25 30

Val Tyr Tyr Cys Val Arg
35

<210> SEQ ID NO 43
<211> LENGTH: 38
<212> TYPE: PRT
<213> ORGANISM: Artificial Sequence
<220> FEATURE:
<223> OTHER INFORMATION: Synthetic_Framework3 in Heavy chain variable region of humanized anti-CD66c antibody (8F5-human-VH5)

<400> SEQUENCE: 43

Asn Gln Arg Phe Lys Val Lys Ala Thr Leu Thr Val Asp Val Ser Thr
1 5 10 15

Asn Thr Ala Tyr Met Glu Leu Ser Arg Leu Arg Ser Asp Asp Thr Ala
20 25 30

Val Tyr Tyr Cys Val Arg
35

<210> SEQ ID NO 44
<211> LENGTH: 38
<212> TYPE: PRT
<213> ORGANISM: Artificial Sequence
<220> FEATURE:

-continued

<223> OTHER INFORMATION: Synthetic_Framework3 in Heavy chain variable region of humanized anti-CD66c antibody (8F5-human-VH6)

<400> SEQUENCE: 44

```
Asn Gln Arg Phe Lys Val Lys Ala Thr Leu Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35
```

<210> SEQ ID NO 45
<211> LENGTH: 38
<212> TYPE: PRT
<213> ORGANISM: Artificial Sequence
<220> FEATURE:
<223> OTHER INFORMATION: Synthetic_Framework3 in Heavy chain variable region of humanized anti-CD66c antibody (8F5-human-VH7)

<400> SEQUENCE: 45

```
Asn Gln Arg Phe Lys Val Lys Ala Thr Leu Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35
```

<210> SEQ ID NO 46
<211> LENGTH: 38
<212> TYPE: PRT
<213> ORGANISM: Artificial Sequence
<220> FEATURE:
<223> OTHER INFORMATION: Synthetic_Framework3 in Heavy chain variable region of humanized anti-CD66c antibody (8F5-human-VH10)

<400> SEQUENCE: 46

```
Asn Gln Arg Phe Lys Val Lys Ala Thr Met Thr Val Asp Val Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35
```

<210> SEQ ID NO 47
<211> LENGTH: 38
<212> TYPE: PRT
<213> ORGANISM: Artificial Sequence
<220> FEATURE:
<223> OTHER INFORMATION: Synthetic_Framework3 in Heavy chain variable region of humanized anti-CD66c antibody (8F5-human-VH11)

<400> SEQUENCE: 47

```
Ala Gln Lys Phe Lys Gly Arg Val Thr Met Thr Arg Asp Thr Ser Thr
1               5                   10                  15

Asn Thr Ala Tyr Met Glu Leu Ser Arg Leu Arg Ser Asp Asp Thr Ala
            20                  25                  30

Val Tyr Tyr Cys Val Arg
        35
```

<210> SEQ ID NO 48
<211> LENGTH: 26
<212> TYPE: PRT
<213> ORGANISM: Artificial Sequence
<220> FEATURE:
<223> OTHER INFORMATION: Synthetic_Framework3 in Light chain variable region of chimeric anti-CD66c antibody

<400> SEQUENCE: 48

Gly Met Ser Ser Arg Phe Ser Gly Ser Gly Ser Gly Arg Gln Tyr Ser
1 5 10 15

Leu Lys Ile Ser Ser Leu His Pro Asp Asp
20 25

<210> SEQ ID NO 49
<211> LENGTH: 26
<212> TYPE: PRT
<213> ORGANISM: Artificial Sequence
<220> FEATURE:
<223> OTHER INFORMATION: Synthetic_Framework3 in Light chain variable region of humanized anti-CD66c antibody (8F5-human-VK5)

<400> SEQUENCE: 49

Gly Val Pro Ser Arg Phe Ser Gly Ser Gly Ser Gly Arg Gln Tyr Ser
1 5 10 15

Leu Lys Ile Ser Ser Leu His Pro Asp Asp
20 25

<210> SEQ ID NO 50
<211> LENGTH: 26
<212> TYPE: PRT
<213> ORGANISM: Artificial Sequence
<220> FEATURE:
<223> OTHER INFORMATION: Synthetic_Framework3 in Light chain variable region of humanized anti-CD66c antibody (8F5-human-VK7)

<400> SEQUENCE: 50

Gly Val Pro Ser Arg Phe Ser Gly Ser Gly Ser Gly Thr Glu Tyr Thr
1 5 10 15

Leu Thr Ile Ser Ser Leu Gln Pro Asp Asp
20 25

<210> SEQ ID NO 51
<211> LENGTH: 26
<212> TYPE: PRT
<213> ORGANISM: Artificial Sequence
<220> FEATURE:
<223> OTHER INFORMATION: Synthetic_Framework3 in Light chain variable region of humanized anti-CD66c antibody (8F5-human-VK8)

<400> SEQUENCE: 51

Gly Met Pro Ser Arg Phe Ser Gly Ser Gly Ser Gly Thr Glu Tyr Thr
1 5 10 15

Leu Thr Ile Ser Ser Leu Gln Pro Asp Asp
20 25

<210> SEQ ID NO 52
<211> LENGTH: 11
<212> TYPE: PRT
<213> ORGANISM: Artificial Sequence
<220> FEATURE:
<223> OTHER INFORMATION: Synthetic_Framework4 in Light chain variable region of chimeric anti-CD66c antibody

<400> SEQUENCE: 52

Trp Gly Gln Gly Thr Ser Val Thr Val Ser Ser
1 5 10

<210> SEQ ID NO 53

<211> LENGTH: 11
<212> TYPE: PRT
<213> ORGANISM: Artificial Sequence
<220> FEATURE:
<223> OTHER INFORMATION: Synthetic_Framework4 in Heavy chain variable
region of humanized anti-CD66c antibody (8F5-human-VH5)

<400> SEQUENCE: 53

Trp Gly Gln Gly Thr Leu Val Thr Val Ser Ser
1 5 10

<210> SEQ ID NO 54
<211> LENGTH: 11
<212> TYPE: PRT
<213> ORGANISM: Artificial Sequence
<220> FEATURE:
<223> OTHER INFORMATION: Synthetic_Framework4 in Heavy chain variable
region of humanized anti-CD66c antibody (8F5-human-VH6)

<400> SEQUENCE: 54

Trp Gly Gln Gly Thr Leu Val Thr Val Ser Ser
1 5 10

<210> SEQ ID NO 55
<211> LENGTH: 11
<212> TYPE: PRT
<213> ORGANISM: Artificial Sequence
<220> FEATURE:
<223> OTHER INFORMATION: Synthetic_Framework 4 in Heavy chain variable
region of humanized anti-CD66c antibody (8F5-human-VH7)

<400> SEQUENCE: 55

Trp Gly Gln Gly Thr Leu Val Thr Val Ser Ser
1 5 10

<210> SEQ ID NO 56
<211> LENGTH: 11
<212> TYPE: PRT
<213> ORGANISM: Artificial Sequence
<220> FEATURE:
<223> OTHER INFORMATION: Synthetic_Framework4 in Heavy chain variable
region of humanized anti-CD66c antibody (8F5-human-VH10)

<400> SEQUENCE: 56

Trp Gly Gln Gly Thr Leu Val Thr Val Ser Ser
1 5 10

<210> SEQ ID NO 57
<211> LENGTH: 11
<212> TYPE: PRT
<213> ORGANISM: Artificial Sequence
<220> FEATURE:
<223> OTHER INFORMATION: Synthetic_Framework4 in Heavy chain variable
region of humanized anti-CD66c antibody (8F5-human-VH11)

<400> SEQUENCE: 57

Trp Gly Gln Gly Thr Leu Val Thr Val Ser Ser
1 5 10

<210> SEQ ID NO 58
<211> LENGTH: 10
<212> TYPE: PRT
<213> ORGANISM: Artificial Sequence
<220> FEATURE:
<223> OTHER INFORMATION: Synthetic_Framework4 in Light chain variable
region of chimeric anti-CD66c antibody

<400> SEQUENCE: 58

-continued

Phe Gly Gly Gly Thr Lys Leu Glu Ile Ile
1 5 10

<210> SEQ ID NO 59
<211> LENGTH: 10
<212> TYPE: PRT
<213> ORGANISM: Artificial Sequence
<220> FEATURE:
<223> OTHER INFORMATION: Synthetic_Framework4 in Light chain variable region of humanized anti-CD66c antibody (8F5-human-VK5)

<400> SEQUENCE: 59

Phe Gly Gly Gly Thr Lys Leu Glu Ile Lys
1 5 10

<210> SEQ ID NO 60
<211> LENGTH: 10
<212> TYPE: PRT
<213> ORGANISM: Artificial Sequence
<220> FEATURE:
<223> OTHER INFORMATION: Synthetic_Framework4 in Light chain variable region of humanized anti-CD66c antibody (8F5-human-VK7)

<400> SEQUENCE: 60

Phe Gly Gly Gly Thr Lys Leu Glu Ile Lys
1 5 10

<210> SEQ ID NO 61
<211> LENGTH: 10
<212> TYPE: PRT
<213> ORGANISM: Artificial Sequence
<220> FEATURE:
<223> OTHER INFORMATION: Synthetic_Framework4 in Light chain variable region of humanized anti-CD66c antibody (8F5-human-VK8)

<400> SEQUENCE: 61

Phe Gly Gly Gly Thr Lys Leu Glu Ile Lys
1 5 10

<210> SEQ ID NO 62
<211> LENGTH: 363
<212> TYPE: DNA
<213> ORGANISM: Artificial Sequence
<220> FEATURE:
<223> OTHER INFORMATION: Synthetic_Polynucleotide encoding heavy chain variable region of chimeric anti-CD66c antibody

<400> SEQUENCE: 62
gaggtccagc tgcaacagtc tggacctgaa ctggtgaagc ctggagcttc aatgaagata 60
tcctgcaagg cttctggtta ctcattcact gactacacca tgaactgggt gaagcagagc 120
catggaaaga accttgagtg gattggactt attaatcctt tccatggtgg tactgtctcc 180
aaccagaggt tcaaggtcaa ggccacatta actgtagaca agtcatccaa cacagcctac 240
atggagctcc tcagtctgac atctgacgac tctgcggtct attactgtgt aagaggtgac 300
ccggtccgcc attactatgc tttggcctac tggggtcagg gaacctcagt caccgtctcc 360
tca 363

<210> SEQ ID NO 63
<211> LENGTH: 217
<212> TYPE: DNA
<213> ORGANISM: Artificial Sequence
<220> FEATURE:
<223> OTHER INFORMATION: Synthetic_Polynucleotide encoding light chain variable region of chimeric anti-CD66c antibody

<400> SEQUENCE: 63
gacatccaga tgactcagtc tccagcttca ctgtctgcat ctgtgggaga aactgtcacc 60
atcacatgtg gagcaagtga gaatgtttac ggtactttaa attggtatca gcggaaacag 120
ggaaaatctc ctcagctcct gatctatggt gcaaccaact tggcagatgg catgtcatcg 180
aggttcagtg gcagtggttc tggtagacag tattctc 217

<210> SEQ ID NO 64
<211> LENGTH: 21
<212> TYPE: DNA
<213> ORGANISM: Artificial Sequence
<220> FEATURE:
<223> OTHER INFORMATION: Synthetic_8F01 Primer of 1st frag forward

<400> SEQUENCE: 64
attactcgag gccaccatga a 21

<210> SEQ ID NO 65
<211> LENGTH: 23
<212> TYPE: DNA
<213> ORGANISM: Artificial Sequence
<220> FEATURE:
<223> OTHER INFORMATION: Synthetic_8F02 Primer of 1st frag reverse

<400> SEQUENCE: 65
agttgaagcg ctgctcacag tca 23

<210> SEQ ID NO 66
<211> LENGTH: 23
<212> TYPE: DNA
<213> ORGANISM: Artificial Sequence
<220> FEATURE:
<223> OTHER INFORMATION: Synthetic_8F03 Primer of 2nd frag forward

<400> SEQUENCE: 66
gtgagcagcg cttcaactaa ggg 23

<210> SEQ ID NO 67
<211> LENGTH: 26
<212> TYPE: DNA
<213> ORGANISM: Artificial Sequence
<220> FEATURE:
<223> OTHER INFORMATION: Synthetic_3E04 Primer of 2nd frag reverse

<400> SEQUENCE: 67
agtcgaattc tcatttccca ggagag 26

<210> SEQ ID NO 68
<211> LENGTH: 23
<212> TYPE: DNA
<213> ORGANISM: Artificial Sequence
<220> FEATURE:
<223> OTHER INFORMATION: Synthetic_8F04 Primer of 1st frag reverse

<400> SEQUENCE: 68
agttgaagca gaagacactg tca 23

<210> SEQ ID NO 69
<211> LENGTH: 23
<212> TYPE: DNA
<213> ORGANISM: Artificial Sequence
<220> FEATURE:
<223> OTHER INFORMATION: Synthetic_8F05 Primer of 1st frag forward

<400> SEQUENCE: 69
gtgtcttctg cttcaactaa ggg 23

<210> SEQ ID NO 70
<211> LENGTH: 26
<212> TYPE: DNA
<213> ORGANISM: Artificial Sequence
<220> FEATURE:
<223> OTHER INFORMATION: Synthetic_3E01 Primer of 1st frag forward

<400> SEQUENCE: 70
attactcgag gccaccatga agtggg 26

<210> SEQ ID NO 71
<211> LENGTH: 23
<212> TYPE: DNA
<213> ORGANISM: Artificial Sequence
<220> FEATURE:
<223> OTHER INFORMATION: Synthetic_8F06 Primer of 1st frag reverse

<400> SEQUENCE: 71
aacagtccgc ttgatctcca gct 23

<210> SEQ ID NO 72
<211> LENGTH: 23
<212> TYPE: DNA
<213> ORGANISM: Artificial Sequence
<220> FEATURE:
<223> OTHER INFORMATION: Synthetic_3EL02(2) Primer of 2nd frag forward

<400> SEQUENCE: 72
gagatcaagc ggactgttgc tgc 23

<210> SEQ ID NO 73
<211> LENGTH: 26
<212> TYPE: DNA
<213> ORGANISM: Artificial Sequence
<220> FEATURE:
<223> OTHER INFORMATION: Synthetic_3E08 Primer of 2nd frag reverse

<400> SEQUENCE: 73
attagaattc tcagcactcg ccgcgg 26

<210> SEQ ID NO 74
<211> LENGTH: 330
<212> TYPE: PRT
<213> ORGANISM: Artificial Sequence
<220> FEATURE:
<223> OTHER INFORMATION: Synthetic_Heavy chain constant region of IgG1

<400> SEQUENCE: 74

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

-continued

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 75
<211> LENGTH: 993
<212> TYPE: DNA
<213> ORGANISM: Artificial Sequence
<220> FEATURE:
<223> OTHER INFORMATION: Synthetic_DNA sequence of Heavy chain constant region of IgG1

<400> SEQUENCE: 75

```
gcttcaacta agggaccaag cgtattccca cttgctccat ctagcaagag cactagcgga      60

ggaacagctg ctttggggtg tttggtaaag gattactttc ccgaacctgt taccgtgagc     120

tggaacagcg gggctttgac aagtggcgtt catacatttc ctgccgtttt gcaaagcagc     180

ggcttgtata gcttgagctc tgttgttacc gttccaagct catctctggg cacacaaaca     240

tacatctgca acgtgaacca caagccctca aacaccaagg tggacaagaa ggtggagcca     300

aagtcttgcg acaagaccca cacctgtcca ccttgtccag cccctgaact cctgggggggc    360

ccttcagttt ttctctttcc tcctaaacct aaagatacac tcatgatcag tcggacccct     420

gaagttacct gtgtggtggt cgatgtgtct catgaagatc ctgaagtcaa gtttaactgg     480

tatgtggacg gcgtggaggt gcataatgcc aagaccaagc ctcgggagga gcaatataat     540

tctacctatc gcgtcgtctc tgtcctcacc gtcctgcatc aggactggct gaatggcaaa     600

gagtataagt gcaaagtcag taacaaagcc ctccccgccc ccatagagaa aaccattagt     660

aaagccaaag ggcagccccg cgagccccag gtctatacac tgccccccag tagagacgag     720
```

```
ctgacaaaga atcaggtgtc tctgacatgc ctggtgaaag gcttttatcc ctctgacatt    780

gccgtcgagt gggagtctaa tgggcagccc gagaataatt ataagacaac acccccccgtg   840

ctggacagtg acggctcatt tttcctgtat tcaaaactga cagtggacaa aagtcggtgg    900

cagcagggga atgtgttttc atgcagtgtc atgcacgagg ccctccacaa tcactatacc    960

cagaaatctc tgagtctctc tcctgggaaa tga                                 993


<210> SEQ ID NO 76
<211> LENGTH: 326
<212> TYPE: PRT
<213> ORGANISM: Artificial Sequence
<220> FEATURE:
<223> OTHER INFORMATION: Synthetic_Heavy chain constant region of IgG2

<400> SEQUENCE: 76

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
```

305 310 315 320

Ser Leu Ser Pro Gly Lys
325

<210> SEQ ID NO 77
<211> LENGTH: 981
<212> TYPE: DNA
<213> ORGANISM: Artificial Sequence
<220> FEATURE:
<223> OTHER INFORMATION: Synthetic_DNA sequence of Heavy chain constant region of IgG2

<400> SEQUENCE: 77
gcttccacca agggcccatc cgtgttccct ctggccccat gttctaggtc tacatctgag 60
agcaccgccg ccctcggctg tctggtgaag gattatttcc ccgagcccgt gaccgtgtct 120
tggaacagcg gagccctgac tagcggagtg cacaccttcc cagctgtgct gcagagctcc 180
ggcctgtaca gcctctcttc tgtggtgacc gtgccctcta gcaacttcgg aacacagacc 240
tacacatgta acgtggatca caagccttcc aacaccaagg tggataagac cgtggagaga 300
aagtgctgtg tggagtgccc tccatgtcct gccccacctg tggctggacc ttctgtgttt 360
ctgttccctc caaagccaaa ggataccctg atgatcagca gaactcctga ggtgacctgt 420
gtggtggtgg acgtgagcca cgaggatcct gaggtgcagt ttaactggta cgtggatggc 480
gtggaggtgc ataacgctaa gacaaagcct agggaggagc agtttaacag caccttcaga 540
gtggtgagcg tgctgaccgt ggtgcaccag gattggctga acggcaagga gtataagtgt 600
aaggtgtcta acaagggcct gccagcccct attgagaaga ccatcagtaa gaccaaggga 660
cagcctaggg agcctcaggt gtacaccctg cctccttcca gagaggagat gacaaagaac 720
caggtgagcc tgacctgtct ggtgaagggc ttctacccta gcgatatcgc cgtggagtgg 780
gagagcaacg gccagcctga gaacaactac aagaccaccc cacctatgct ggacagcgat 840
ggctctttct tcctgtactc taagctgacc gtggacaaga gcagatggca gcagggcaac 900
gtgttttctt gttctgtgat gcacgaggcc ctgcacaacc actacaccca gaagtctctg 960
tctctgtctc caggcaagtg a 981

<210> SEQ ID NO 78
<211> LENGTH: 107
<212> TYPE: PRT
<213> ORGANISM: Artificial Sequence
<220> FEATURE:
<223> OTHER INFORMATION: Synthetic_Light chain constant region

<400> SEQUENCE: 78

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys

-continued

```
            100                 105


<210> SEQ ID NO 79
<211> LENGTH: 324
<212> TYPE: DNA
<213> ORGANISM: Artificial Sequence
<220> FEATURE:
<223> OTHER INFORMATION: Synthetic_DNA sequence of Light chain constant
      region

<400> SEQUENCE: 79

cggactgttg ctgctccatc tgtttttata tttcctccca gcgacgagca gctgaaaagc     60

ggcactgcct ctgtggtgtg tctgctgaat aatttttacc cccgggaagc caaagtccag    120

tggaaggtgg ataatgccct ccagtctggg aacagtcagg aaagtgtgac agaacaggat    180

agtaaggact ctacttatag cctctcttct acactgactc tgtcaaaggc cgactatgag    240

aagcataaag tgtatgcctg cgaggtgaca catcagggcc tgagttcacc cgtgacaaaa    300

tcttttaacc gcggcgagtg ctga                                           324
```